(12) United States Patent
Aurrecoechea et al.

(10) Patent No.: US 8,129,396 B2
(45) Date of Patent: Mar. 6, 2012

(54) 2-[1H-BENZIMIDAZOL-2(3H)-YLIDENE]-2-(PYRIMIDIN-2-YL)ACETAMIDES AND 2-[BENZOTHIAZOL-2(3H)-YLIDENE]-2-(PYRIMIDIN-2-YL)ACETAMIDES AS KINASE INHIBITORS

(75) Inventors: Natalia Aurrecoechea, Oakland, CA (US); Paul P. Beroza, Belmont, CA (US); Komath V. Damodaran, Cupertino, CA (US); Karen Y. Pontius, Aromas, CA (US); Louise Robinson, San Carlos, CA (US); Reyna J. Simon, Los Gatos, CA (US); Truong Vu, San Martin, CA (US); Kevin T. Weber, Carmel, IN (US)

(73) Assignee: Telik, Inc., Palo Alto, CA (US)

( * ) Notice: Subject to any disclaimer, the term of this patent is extended or adjusted under 35 U.S.C. 154(b) by 43 days.

(21) Appl. No.: 12/567,060

(22) Filed: Sep. 25, 2009

(65) Prior Publication Data

US 2010/0081653 A1     Apr. 1, 2010

Related U.S. Application Data

(60) Provisional application No. 61/100,869, filed on Sep. 29, 2008.

(51) Int. Cl.
C07D 239/42 (2006.01)
C07D 401/04 (2006.01)
C07D 239/02 (2006.01)

(52) U.S. Cl. .................... 514/256; 544/335

(58) Field of Classification Search ............... 544/335; 514/256
See application file for complete search history.

(56) References Cited

FOREIGN PATENT DOCUMENTS

EP       1 110 957 A1    6/2001
WO   WO 2006/120557 A1  11/2006
WO   WO 2007/009524 A1   1/2007

OTHER PUBLICATIONS

Voskoglou-Nomikos et al., Clinical Cancer Research, vol. 9, 4227-4239.*
ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*
Voskoglou-Nmikos et al., Clinical Cancer Research, vol. 9, 4227-4239, 2003.*
Barnikow, G. et al., "Zur Kentnis der Hugershoff-Reaktion. VI) Die Umsetzung von Acetyl-malonsäure-äthylesterthioaniliden und anderen Thion-Thiol-tautomerenVerbindungen mit Brom", *J. Prakt. Chemie* 1966, 5(5-6), 262-268.
Carvajal, R.D. et al., "Aurora Kinases: New Targets for Cancer Therapy", *Clin. Cancer Res.* 2006, 12, 6869-6875.
Ellis, L.M. and D.J. Hicklin., "VEGF-targeted therapy: mechanisms of anti-tumour activity", *Nature Rev. Cancer* 2008, 8, 579-591 [Published online Jul. 3, 2008].
Ferrara, N. and R.S. Kerbel, "Angiogenesis as a therapeutic target", *Nature* 2005, 438, 967-974.
Gaillard, P. et al., Design and Synthesis of the First Generation of Novel Potent, Selective and in Vivo Active (Benzothiazol-2-yl)acetonitrile Inhibitors of the c-Jun N-Terminal Kinase, *J. Med. Chem.* 2005, 48, 4596-4607.
Mortlock, A. et al., "Progress in the Development of Selective Inhibitors of Aurora Kinases", *Curr. Topics Med. Chem.* 2005, 5, 199-213.
Myrianthopoulos, V. et al., "An Integrated Computational Approach to the Phenomenon of Potent and Selective Inhibition of Aurora Kinases B and C by a Series of 7-Substituted Indirubins", *J. Med. Chem.* 2007, 50(17), 4027-4037 [Published online Aug. 1, 2007].
Shaikh, A.R. et al., "Three-dimensional quantitative structure-activity relationship (3 D-QSAR) and docking studies on (benzothioazole-2-yl)acetonitrile derivatives as c-Jun N-terminal kinase-3 (JNK-3) inhibitors", *Bioorg. Med. Chem. Lett.* 2006, 16(22), 5917-5925.

* cited by examiner

*Primary Examiner* — Rebecca Anderson
(74) *Attorney, Agent, or Firm* — Foley & Lardner LLP

(57) ABSTRACT

2-[1H-benzimidazol-2(3H)-ylidene]-2-(pyrimidin-2-yl)acetamides and 2-[benzothiazol-2(3H)-ylidene]-2-(pyrimidin-2-yl)acetamides and their salts are kinase inhibitors, useful in the treatment of cancer.

21 Claims, No Drawings

2-[1H-BENZIMIDAZOL-2(3H)-YLIDENE]-2-(PYRIMIDIN-2-YL)ACETAMIDES AND 2-[BENZOTHIAZOL-2(3H)-YLIDENE]-2-(PYRIMIDIN-2-YL)ACETAMIDES AS KINASE INHIBITORS

CROSS-REFERENCE TO RELATED APPLICATION

This application claims the benefit under 35 USC 119(e) of U.S. Provisional Patent Application No. 61/100,869, filed 29 Sep. 2008, entitled "2-[1H-benzimidazol-2(3H)-ylidene]- and 2-[benzothiazol-2(3H)-ylidene]-2-(pyrimidin-2-yl)acetamides as kinase inhibitors", the entire disclosure of which is incorporated into this application by reference.

BACKGROUND OF THE INVENTION

1. Field of the Invention

This invention relates to 2-[1H-benzimidazol-2(3H)-ylidene]-2-(pyrimidin-2-yl)acetamides and 2-[benzothiazol-2(3H)-ylidene]-2-(pyrimidin-2-yl)acetamides, their salts, pharmaceutical compositions containing them, and their use as kinase inhibitors and in the treatment of cancer.

2. Description of the Related Art

As discussed by Mortlock et al., "Progress in the Development of Selective Inhibitors of Aurora Kinases", *Curr. Topics Med. Chem.* 2005, 5, 199-213, and Carvajal et al., "Aurora Kinases: New Targets for Cancer Therapy", *Clin. Cancer Res.* 2006, 12, 6869-6875, the Aurora family of kinases are involved in the regulation of mitosis. Two of the three human Aurora kinases, Aurora A and Aurora B, are frequently overexpressed in human tumors, while the Aurora A gene itself is amplified in many tumors. There has thus been considerable interest in the development of inhibitors of Aurora kinases as anticancer compounds for the treatment of both solid malignancies (e.g., colorectal, lung, breast, pancreatic, and bladder cancer) and hematological malignancies (e.g., acute lymphocytic leukemia (ALL), chronic myelogenous leukemia (CML), Hodgkin's and non-Hodgkin's lymphomas, and myelodysplastic syndrome (MDS)). A number of compounds have reached clinical trials, including Vertex and Merck's VX-680/MK-0457, which reached Phase II clinical studies but has now been discontinued and replaced in development by a later compound, VX-689 (MK-5108); Astex's AT9283; Astra Zeneca's AZD-1152; Entremed's ENMD-2076 and ENMD-981693; Millennium's MLN-8054 and MLN-8237; Nerviano's PHA-739358; Rigel's R763; Sunesis's SNS-314; and others.

As discussed by Ferrera and Kerbel, "Angiogenesis as a therapeutic target", *Nature* 2005, 438, 967-974, and more recently by Ellis and Hicklin, "VEGF-targeted therapy: mechanisms of anti-tumour activity", *Nature Rev. Cancer* 2008, 8, 579-591, the inhibition of angiogenesis by the targeting of VEGF-A and its receptors is considered to be a highly promising strategy for cancer treatment. Two inhibitors of VEGFR2 kinase; sunitinib (Pfizer's Sutent®) and sorafenib (Bayer/Onyx's Nexavar®) are already approved in the US for the treatment of kidney cancer, while sunitinib is also approved for the treatment of gastro-intestinal cancer. A number of other VEGFR2 kinase-inhibiting compounds are in advanced development, among them GSK's pazopanib, Novartis's vatalinib, Pfizer's axitinib, Astra Zeneca's vandetanib, and others, for both solid (e.g. breast, ovarian, lung, and colorectal) and hematological malignancies. Also, bevacizumab (Genentech's Avastin), although not a VEGFR2 kinase inhibitor but an anti-VEGF antibody, is seeing use in brain cancer, suggesting that VEGFR2 kinase inhibitors may also find use in it, as in all other solid tumors.

Many of these compounds, whether the Aurora kinase inhibitors or the VEGFR inhibitors mentioned in the above paragraphs, are not specific inhibitors of the named kinases, but rather are selective inhibitors of the named kinases, also acting on other kinases. For example, sorafenib and sunitinib also have significant activity against Raf kinase and other kinases, and Cyclacel's CYC116 has been reported to inhibit Aurora kinases A, B, and C, VEGFR2 kinase, and Flt3 with $IC_{50}$s all below 100 nM.

It would be desirable to develop compounds that are potent inhibitors of Aurora kinase, also inhibiting VEGFR2 kinase, as anticancer agents.

The disclosures of the documents referred to in this application are incorporated into this application by reference.

SUMMARY OF THE INVENTION

In a first aspect, this invention is compounds of formula A:

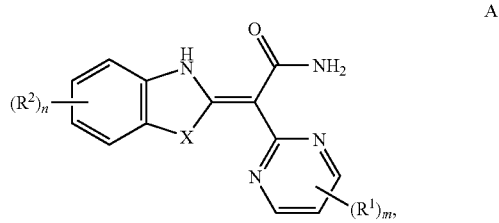

and their salts,
where:
X is NH or S;
m is 0, 1, 2, or 3;
n is 0, 1, 2, 3, or 4;
$R^1$ is alkyl, substituted alkyl, heteroalkyl, substituted heteroalkyl, aryl, substituted aryl, heteroaryl, substituted heteroaryl, aralkyl, substituted aralkyl, heteroaralkyl, substituted heteroaralkyl, halo, nitro, or cyano, or is —OR, —SR, —C(O)R, —OC(O)R, —C(O)OR, —NR$_2$, —SO$_2$OR, —OSO$_2$R, —SO$_2$NR$_2$, —NR$^3$SO$_2$R, —CONR$_2$, —NR$^3$COR, and —NR$^3$C(O)OR, where each R independently is hydrogen, alkyl, substituted alkyl, heteroalkyl, substituted heteroalkyl, aryl, substituted aryl, heteroaryl, substituted heteroaryl, aralkyl, substituted aralkyl, heteroaralkyl, or substituted heteroaralkyl, and $R^3$ is hydrogen or $C_1$-$C_3$ alkyl; and $R^2$ is alkyl, substituted alkyl, heteroalkyl, substituted heteroalkyl, aryl, substituted aryl, heteroaryl, substituted heteroaryl, aralkyl, substituted aralkyl, heteroaralkyl, substituted heteroaralkyl, halo, nitro, or cyano, or is —OR, —SR, —C(O)R, —OC(O)R, —C(O)OR, —NR$_2$, —SO$_2$OR, —OSO$_2$R, —SO$_2$NR$_2$, —NR$^3$SO$_2$R, —CONR$_2$, —NR$^3$COR, and —NR$^3$C(O)OR, where each R independently is hydrogen, alkyl, substituted alkyl, heteroalkyl, substituted heteroalkyl, aryl, substituted aryl, heteroaryl, substituted heteroaryl, aralkyl, substituted aralkyl, heteroaralkyl, or substituted heteroaralkyl, and $R^3$ is hydrogen or $C_1$-$C_3$ alkyl.

In second through sixth aspects, this invention is compounds of the first aspect of this invention for use as kinase inhibitors, especially as inhibitors of Aurora kinase (notably Aurora kinases A and B) and optionally VEGFR2 kinase, pharmaceutical compositions containing the compounds of the first aspect of this invention, use of the compounds of the first aspect of this invention as kinase inhibitors and for the manufacture of medicaments, and methods of treatment using the compounds of the first aspect of this invention.

In a seventh aspect, this invention is methods of making the compounds of the first aspect of this invention.

Preferred embodiments of this invention are characterized by the specification including the examples.

DETAILED DESCRIPTION OF THE INVENTION

Definitions

"Alkyl" means a monovalent group derived from a saturated or unsaturated (but not aromatically unsaturated) $C_1$-$C_{10}$ hydrocarbon that may be linear, branched, or cyclic, by removal of one hydrogen atom from a carbon atom. Examples are methyl, ethyl, propyl, 1-propenyl, isopropyl, butyl, isobutyl, sec-butyl, tert-butyl, pentyl, hexyl, cyclopentyl, cyclopenten-1-yl, cyclopropylmethyl, cyclohexyl, and cyclohexylmethyl. Saturated alkyls (including cycloalkyls) and $C_1$-$C_6$ alkyls ("lower alkyls"), especially $C_1$-$C_3$ alkyls, are exemplary. Note that the definition of "alkyl" in this application is broader than the conventional definition and includes groups more commonly referred to as "cycloalkyl", "cycloalkylalkyl", "alkenyl", and "alkynyl".

A "substituted alkyl" is an alkyl substituted with up to three halogen atoms and/or up to three substituents selected from nitro, cyano, —OR, —SR, —COR, —OC(O)R, —C(O)OR, —NR$_2$, —SO$_2$OR, —OSO$_2$R, —SO$_2$NR$_2$, —NRSO$_2$R, —CONR$_2$, —NRCOR, and —NRC(O)OR, where each R independently is hydrogen, optionally R'-substituted alkyl, optionally R'-substituted heteroalkyl, optionally R'-substituted aryl, optionally R'-substituted heteroaryl, optionally R'-substituted aralkyl, or optionally R'-substituted heteroaralkyl and each R' independently is 1 to 3 substituents selected from halo, nitro, cyano, hydroxy, mercapto, amino, cycloamino, $C_{1-3}$ alkyl, $C_{1-3}$ alkyloxy, or —C(O)O—$C_{1-3}$ alkyl (preferably, 1 to 3 substituents selected from halo, nitro, cyano, hydroxy, mercapto, amino, cycloamino, $C_{1-3}$ alkyl, or $C_{1-3}$ alkyloxy), or two R groups together form a 4- to 6-member optionally R'-substituted alkanediyl or optionally R'-substituted heteroalkanediyl (especially where the nitrogen and the two R groups of —NR$_2$ form a cycloamino group). Thus, for example, substituted alkyl groups include such groups as trifluoromethyl, 3-chloropropyl, and 2-(morpholin-4-yl)ethyl.

"Heteroalkyl" means alkyl in which 1 to 3 of the carbon atoms are replaced by O, S, SO$_2$, or NR (where R is H or $C_{1-3}$ alkyl optionally substituted with halogen or hydroxy), including linear groups such as 3-oxapentyl; monocyclic rings containing 5 or 6 ring atoms such as 2-tetrahydrofuranyl, 2-pyrrolidinyl, 3-piperidinyl, 2-piperazinyl, 4-methyl-1-piperazinyl, 4-dihydropyranyl, and 3-morpholinyl; and groups such as tetrahydrofuran-2-ylmethyl and piperidin-3-ylethyl. Heteroalkyl groups also include those where a ring nitrogen is oxidized to form an N-oxide. "Substituted heteroalkyl" means heteroalkyl substituted in the manner described above for substituted alkyl. A "cycloamino" group is a cyclic heteroalkyl of 5 to 7 ring atoms containing a nitrogen ring atom by which the group is bonded to the remainder of the molecule of which it forms a part and optionally containing a further ring heteroatom selected from O, S, SO$_2$, and NR (where R is H or $C_{1-3}$ alkyl optionally substituted with halogen, hydroxy, or 1 or 2 phenyl groups). 4-Methyl-1-piperazinyl, 4-(2-hydroxyethyl)-1-piperazinyl, 4-(diphenylmethyl)-1-piperazinyl, and 4-morpholinyl are examples of cycloamino groups. Compounds of this invention also include compounds where any —NR$_2$ group present is replaced by a cycloamino group.

"Aryl" means a monovalent group derived from an aromatic hydrocarbon containing 6 to 14 ring carbon atoms by removal of one hydrogen atom from a carbon atom, which is monocyclic (e.g., phenyl), condensed polycyclic, for example, condensed bicyclic (e.g., naphthyl), or linked polycyclic, for example, linked bicyclic (e.g., biphenylyl). A preferred aryl is phenyl.

"Substituted aryl" means aryl substituted with up to three substituents selected from halo, nitro, cyano, —OR, $C_{1-3}$ alkyl or $C_{1-3}$ alkyloxy (each optionally substituted with halo or —NR$_2$), —SR, —COR, —OC(O)R, —C(O)OR, —NR$_2$, —SO$_2$OR, —OSO$_2$R, —SO$_2$NR$_2$, —NRSO$_2$R, —CONR$_2$, —NRCOR, and —NRC(O)OR, where each R independently is hydrogen, optionally R'-substituted alkyl, optionally R'-substituted heteroalkyl, optionally R'-substituted aryl, optionally R'-substituted heteroaryl, optionally R'-substituted aralkyl, or optionally R'-substituted heteroaralkyl (preferably, hydrogen or optionally R'-substituted alkyl) and each R' independently is 1 to 3 substituents selected from halo, nitro, cyano, hydroxy, mercapto, amino, cycloamino, $C_{1-3}$ alkyl, $C_{1-3}$ alkyloxy, or —C(O)Oalkyl (preferably, halo, nitro, cyano, hydroxy, mercapto, amino, cycloamino, $C_{1-3}$ alkyl, or $C_{1-3}$ alkyloxy), or two R groups together form a 4- to 6-member optionally R'-substituted alkanediyl or optionally R'-substituted heteroalkanediyl (especially where the nitrogen and the two R groups of —NR$_2$ form a cycloamino group). Two adjacent substituents may also form a methylenedioxy or ethylenedioxy group. Substituted aryl groups include aryl groups substituted with up to three substituents selected from the group consisting of halo, nitro, cyano, hydroxy, mercapto, amino, optionally halo-substituted $C_{1-3}$ alkyl, and optionally halo-substituted $C_{1-3}$ alkyloxy, for example, phenyl substituted in this way. Preferred substituted aryls are substituted phenyls.

"Aralkyl" means alkyl substituted with aryl, such as benzyl and phenethyl. A preferred aralkyl is benzyl. "Substituted aralkyl" means aralkyl in which one or both of the aryl and the alkyl are substituted in the manner described above for substituted aryl and substituted alkyl. Preferred substituted aralkyls are substituted benzyls.

"Halogen" or "halo" means F, Cl, Br, I; particularly F or Cl.

"Heteroaryl" means an aromatic monovalent group derived from a cyclic hydrocarbon containing 5 to 14 ring atoms in which 1 to 4 (preferably 1 to 3) of the ring carbon atoms are replaced by O, S, N, or NR (where R is H or $C_{1-3}$ alkyl), preferably O, S, or NR, by removal of one hydrogen atom from a ring carbon atom; including monocyclic groups containing 5 or 6 ring atoms such as furanyl, thienyl, pyrrolyl, oxazolyl, imidazolyl, pyridinyl, pyrazinyl, pyridazinyl, pyrimidinyl, and the like, and bicyclic groups such as benzothiazolyl, purinyl, and benzimidazolyl. Monocyclic rings are preferred. Heteroaryl groups also include those where a ring nitrogen is oxidized to form an N-oxide. "Substituted heteroaryl" means heteroaryl substituted in the manner described above for substituted aryl.

"Heteroaralkyl" means alkyl substituted with heteroaryl, such as 2-thienylmethyl. "Substituted heteroaralkyl" means heteroaralkyl substituted in the manner described above for substituted aralkyl.

"Elaborated" refers to the conversion of a reactive substituent to another typically more complex substituent, such as the conversion of an amine to an amide or sulfonamide, a carboxy group to an ester or amide, a hydroxy to an ester, and conversion of an amide or sulfonamide with one or more hydrogen atoms on the nitrogen to one where one or more of those hydrogen atoms is replaced by an optionally substituted alkyl, heteroalkyl, aryl, heteroaryl, aralkyl, or heteroaralkyl group. "Protected" has its conventional meaning in organic synthesis, namely the temporary conversion of a reactive substituent to a substituent that is non-reactive under the conditions of the reaction(s) proposed to be carried out; such as the protection of an amine as a carbamate.

A "solubility-enhancing group" is a group that enhances the solubility in water of the compound over a compound that is not so substituted, for example, hydroxy and salt-forming groups such as carboxy and non-amide amino groups, especially non-amide amino groups that are capable of forming acid addition salts; or is a group containing one or more of these groups as functional subgroups, such as lower alkyl substituted with hydroxy. Preferred solubility-enhancing groups include —NR'$_2$ (where each R' independently is hydrogen or C$_1$-C$_3$ alkyl, or where —NR'$_2$ together is cycloamino) or a nitrogen-containing heteroaryl; lower alkyl substituted with —NR'$_2$ (where each R' independently is hydrogen or C$_1$-C$_3$ alkyl, or where —NR'$_2$ together is cycloamino) or with a nitrogen-containing heteroaryl; and groups of the formula —OR, —SR, —C(O)R, —OC(O)R, —C(O)OR, —NR$_2$, —SO$_2$R, —OSO$_2$R, —SO$_2$NR$_2$, —NR$^3$SO$_2$R, —CONR$_2$, —NR$^3$COR, and —NR$^3$C(O)OR, where R is lower alkyl substituted with —NR'$_2$ (where each R' independently is H or C$_1$-C$_3$ alkyl, or where —NR'$_2$ together is cycloamino) or with a nitrogen-containing heteroaryl, and R$^3$ is hydrogen or C$_1$-C$_3$ alkyl.

"Salts" are described in the section entitled "Compounds of this invention".

A "therapeutically effective amount" means that amount which, when administered to a human for treating a cancer, is sufficient to effect treatment for the cancer. "Treating" or "treatment" of a cancer in a human includes one or more of:
(1) limiting/inhibiting growth of the cancer, i.e., limiting/arresting its development,
(2) reducing/preventing spread of the cancer, i.e. reducing/preventing metastases,
(3) relieving the cancer, i.e., causing regression of the cancer,
(4) reducing/preventing recurrence of the cancer, and
(5) palliating symptoms of the cancer.

"Combination therapy" means the administration of a compound of the first aspect of this invention and another anticancer therapy during the course of cancer chemotherapy. Such combination therapy may involve the administration of the compound of the first aspect of this invention before, during, and/or after the administration of the another anticancer therapy. The administration of the compound of the first aspect of this invention may be separated in time from the administration of the another anticancer therapy by up to several weeks, and may precede it or follow it, but more commonly the administration of the compound of the first aspect of this invention will accompany at least one aspect of the another anticancer therapy (such as the administration of one dose of a chemotherapeutic agent, molecular targeted therapy agent, biologic therapy agent, or radiation therapy) within up to 48 hours, and most commonly within less than 24 hours.

"Comprising" or "containing" and their grammatical variants are words of inclusion and not of limitation and mean to specify the presence of stated components, groups, steps, and the like but not to exclude the presence or addition of other components, groups, steps, and the like. Thus "comprising" does not mean "consisting of", "consisting substantially of", or "consisting only of"; and, for example, a formulation "comprising" a compound must contain that compound but also may contain other active ingredients and/or excipients.

Compounds of this Invention

Salts (for example, pharmaceutically acceptable salts) of the compounds of formula A are included in the present invention and are useful in the compositions, methods, and uses described in this application. Such salts are preferably formed with pharmaceutically acceptable acids. See, for example, Stahl and Wermuth, eds., "Handbook of Pharmaceutically Acceptable Salts", (2002), Verlag Helvetica Chimica Acta, Zürich, Switzerland, for an extensive discussion of pharmaceutical salts, their selection, preparation, and use. Unless the context requires otherwise, reference to any compound of this invention is a reference both to the compound and to its salts.

These salts include salts that may be formed when acidic protons present are capable of reacting with inorganic or organic bases. Typically the parent compound is treated with an excess of an alkaline reagent, such as hydroxide, carbonate or alkoxide, containing an appropriate cation. Cations such as Na$^+$, K$^+$, Ca$^{2+}$, Mg$^{2+}$ and NH$_4^+$ are examples of cations present in pharmaceutically acceptable salts. Suitable inorganic bases, therefore, include calcium hydroxide, potassium hydroxide, sodium carbonate and sodium hydroxide. Salts may also be prepared using organic bases, such as salts of primary, secondary and tertiary amines, substituted amines including naturally-occurring substituted amines, and cyclic amines including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like.

If a compound of the first aspect of this invention contains a basic group, such as an amino group, it may be prepared as an acid addition salt. Acid addition salts of the compounds are prepared in a standard manner in a suitable solvent from the parent compound and an excess of an acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, 4-toluenesulfonic acid, hexanoic acid, heptanoic acid, cyclopentanepropionic acid, lactic acid, 2-(4-hydroxybenzoyl) benzoic acid, 1,2-ethanedisulfonic acid, 2-hydroxyethanesulfonic acid, benzenesulfonic acid, 4-chlorobenzenesulfonic acid, 2-naphthalenesulfonic acid, camphorsulfonic acid, 4-methylbicyclo[2.2.2.]oct-2-ene-1-carboxylic acid, glucoheptonic acid, gluconic acid, 4,4'-methylenebis(3-hydroxy-2-naphthoic)acid, 3-phenylpropionic acid, trimethylacetic acid, tert-butylacetic acid, laurylsulfuric acid, glucuronic acid, glutamic acid, 3-hydroxy-2-naphthoic acid, stearic acid, muconic acid and the like.

Compounds of this invention include those compounds of formula A where one or more of the following is true:
1.a X is S; or
1.b X is NH;
2. m is at least 1, preferably 1 or 2;
3. the R$^1$ group (when m is 1) or an R$^1$ group is a group on the 4-position (i.e. adjacent to one of the two nitrogen atoms on the pyrimidine ring: may be referred to as the 6-position if m is 2 or 3 and another substituent has naming priority), such as 4-methyl, 4-methoxy, or 4-trifluoromethyl (preferred);

4. when m is 2, the other $R^1$ group is at the 5- or 6-position, especially the 6-position (defined when the first $R^1$ group is at the 4-position); typically a group that is either small (e.g. methyl, methoxy, carboxyl, or $C_1$-$C_3$ alkoxycarbonyl), or a group that enhances a physicochemical property of the molecule, such as a solubility-enhancing group;

5. n is at least 1, preferably 1 or 2;

6. the $R^2$ group (when n is 1) or an $R^2$ group (when n is at least 2) is a group that enhances a physicochemical property of the molecule, such as a solubility-enhancing group.

Generally, a compound having a greater number of these features is preferred over a compound having a lesser number of these features; in particular, addition of one of these features to a compound having less than all the features will generally result in a compound that is preferred over the compound without that feature.

Tautomerism and Naming

The compounds of this invention are named and shown in this application as 2-[1H-benzimidazol-2(3H)-ylidene]-2-(pyrimidin-2-yl)acetamides and 2-[benzothiazol-2(3H)-ylidene]-2-(pyrimidin-2-yl)acetamides, i.e. compounds having an exocyclic double bond between the benzimidazole/benzothiazole section and the 2-(pyrimidin-2-yl)acetamide section of the molecule. However, as will be obvious to a person having ordinary skill in the art, the compounds are tautomeric and may also be named and shown as having the double bond within the imidazole/thiazole ring and the exocyclic bond to the 2-(pyrimidin-2-yl)acetamide being single. Also, because there is no inherent chiral preference at the 2-carbon of the acetamide when the exocyclic bond becomes single, and because the 2-(pyrimidin-2-yl)acetamide section of the molecule may rotate relative to the benzimidazole/benzothiazole section when the exocyclic bond is single, the E and Z isomers when the exocyclic bond is double also become tautomeric. Additional keto-enol tautomerism at the amide, and within the pyrimidine ring, is also possible. Further, there is additional symmetry within the benzimidazole such that the 4- and 7-positions, and the 5- and 6-positions, on the benzimidazole are equivalent. Thus the compounds may adopt a wide variety of at least potentially interchangeable conformations, and the illustration or naming of a compound in this specification and claims in a particular conformation is not intended to be limited to that conformation but is intended to include all conformations applicable to that compound.

For parallelism, each of the compounds of formula A is named in this specification and claims as a derivative of 2-[1H-benzimidazol-2(3H)-ylidene]-2-(pyrimidin-2-yl)acetamide or 2-[benzothiazol-2(3H)-ylidene]-2-(pyrimidin-2-yl)acetamide rather than by following the priority rules of IUPAC naming conventions. Thus, for example, compound 39A, the compound of the formula

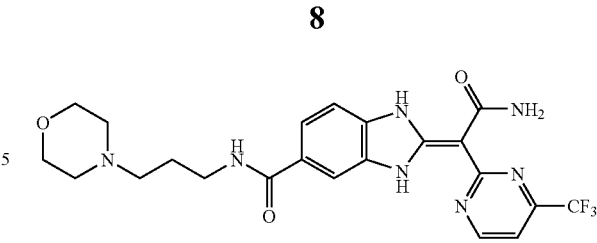

is named 2-(5-{[3-(4-morpholinyl)propyl]aminocarbonyl}-1H-benzimidazol-2 (3H)-ylidene)-2-(4-trifluoromethylpyrimidin-2-yl)acetamide, and compound 40A, the compound of the formula

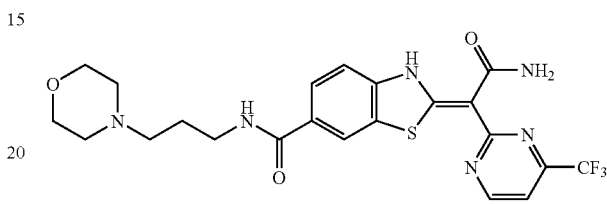

is named 2-(6-{[3-(4-morpholinyl)propyl]aminocarbonyl}-benzothiazol-2(3H)-ylidene)-2-(4-trifluoromethylpyrimidin-2-yl)acetamide.

Compounds of this invention include each of the compounds described in the specification and claims of this application as filed, including in the Examples and the compound table below, such as any one of compounds 1A to 146A, especially any one of compounds 39A to 41A, 60A, 75A, 77A, 81A, 82A, 83A, 95A, 100A, 101A, 117A, 138A, 139A, and 142A to 146A, and their salts; particularly any one of compounds 41A, 75A, 83A, 139A, 142A, 143A, and 145A, and their salts. Compositions and methods, etc., of this invention include compositions and methods, etc., where the compound is one of those mentioned in the preceding sentence.

Preparation of the Compounds

In each of the Reaction Schemes shown below in the discussion of the general synthetic methods, no substituents are shown on the benzene ring of either the benzimidazole/benzothiazole or on the pyrimidine, but it will be apparent that substituents (either the final substituents on the desired compound, or precursors to those final substituents to be modified after formation of the compound core) may be present, as discussed later in the specification and as illustrated by the examples.

A first general synthetic method, applicable to both the benzothiazole- and benzimidazole-based compounds, involves the formation of 2-[1H-benzimidazol-2(3H)-ylidene]acetonitrile or 2-[benzothiazol-2(3H)-ylidene]acetonitrile, followed by coupling with a pyrimidine and hydrolysis of the nitrile to the amide (in either order), and is illustrated in Reaction Scheme 1 below.

Reaction Scheme 1

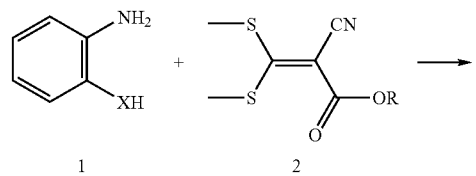

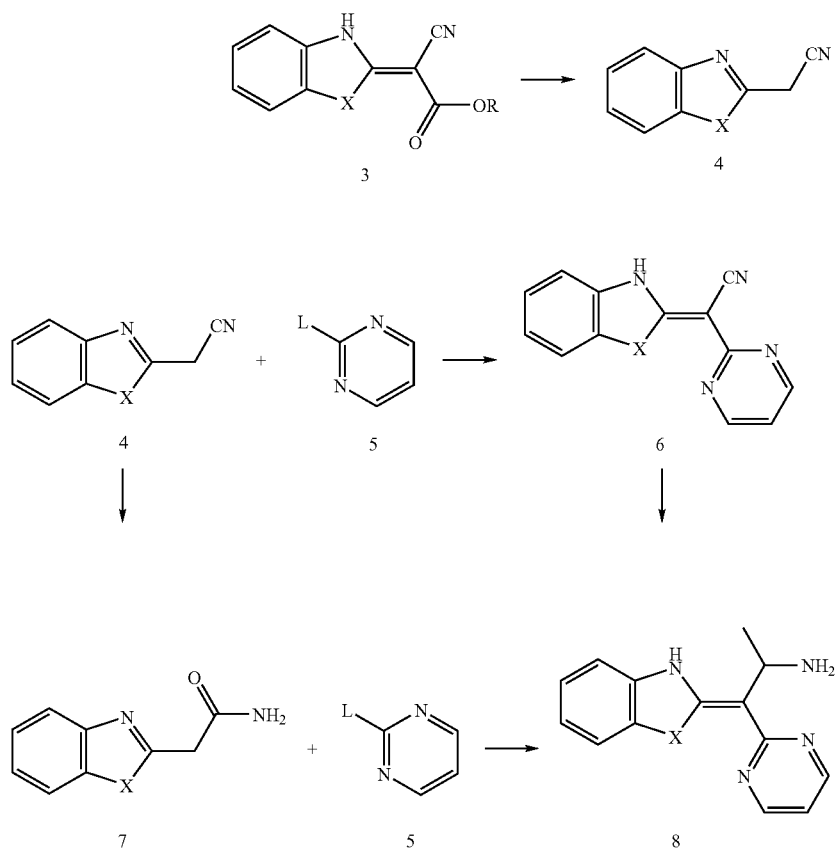

In the first part of the synthesis, in the first step, a benzene-1,2-diamine (1, X=NH) or 2-aminothiophenol (1, X=S) is coupled with a 2-(alkoxycarbonyl)-3,3-bis(methylthio)acrylonitrile 2, such as the ethyl or tert-butyl ester, to give the 2-cyano-2-[1H-benzimidazol-2(3H)-ylidene]acetate or 2-cyano-2-[benzothiazol-2(3H)-ylidene]acetate 3. The reaction is carried out in an alkanol, e.g. ethanol, optionally in the presence of an amine base, such as 4-dimethylaminopyridine, under heating. In the second step, the alkoxycarbonyl group is removed by hydrolysis, for example basic hydrolysis to remove an ethoxycarbonyl group or acidic hydrolysis to remove the preferred tert-butoxycarbonyl group, giving the 2-[1H-benzimidazol-2-yl]acetonitrile or 2-[benzothiazol-2-yl]acetonitrile 4.

2-(Ethoxycarbonyl)-3,3-bis(methylthio)acrylonitrile is commercially available and its preparation described in the literature; the tert-butyl analog may readily be prepared by the same method.

In the second part of the synthesis, the 2-[1H-benzimidazol-2-yl]acetonitrile or 2-[benzothiazol-2-yl]acetonitrile 4 is either coupled with a pyrimidine and then hydrolyzed to the amide, or hydrolyzed and then coupled. If compound 4 is a 2-[1H-benzimidazol-2-yl]acetonitrile, one of the benzimidazole nitrogen atoms may be protected with an amine-protecting group, such as with tert-butoxycarbonyl, preventing N-alkylation. In the coupling/hydrolysis route, compound 4 is then coupled with a pyrimidine 5 [L is a leaving group such as Cl, methylsulfonyl, or methylthio] in the presence of a strong base, such as sodium hydride or lithium hexamethyldisilazane, in an aprotic polar solvent, such as tetrahydrofuran, to give a 2-[1H-benzimidazol-2(3H)-ylidene]-2-(pyrimidin-2-yl)-acetonitrile or 2-[benzothiazol-2(3H)-ylidene]-2-(pyrimidin-2-yl)acetonitrile 6. Compound 6 is then hydrolyzed with concentrated sulfuric acid to give the final 2-[1H-benzimidazol-2(3H)-ylidene]-2-(pyrimidin-2-yl)acetamide or 2-[benzothiazol-2(3H)-ylidene]-2-(pyrimidin-2-yl)acetamide 8. In the hydrolysis/coupling route, the steps of the preceding sentence are reversed: the nitrile of compound 4 is hydrolyzed to the amide, giving compound 7, and compound 7 is then coupled with the pyrimidine 5 to give compound 8.

A second general synthetic method, also applicable to both the benzothiazole- and benzimidazole-based compounds, involves the formation of a 2-[1H-benzimidazol-2(3H)-ylidene]-2-(pyrimidin-2-yl)acetonitrile or 2-[benzothiazol-2(3H)-ylidene]-2-(pyrimidin-2-yl)acetonitrile, followed by hydrolysis of the nitrile to the amide, and is illustrated in Reaction Scheme 2 below.

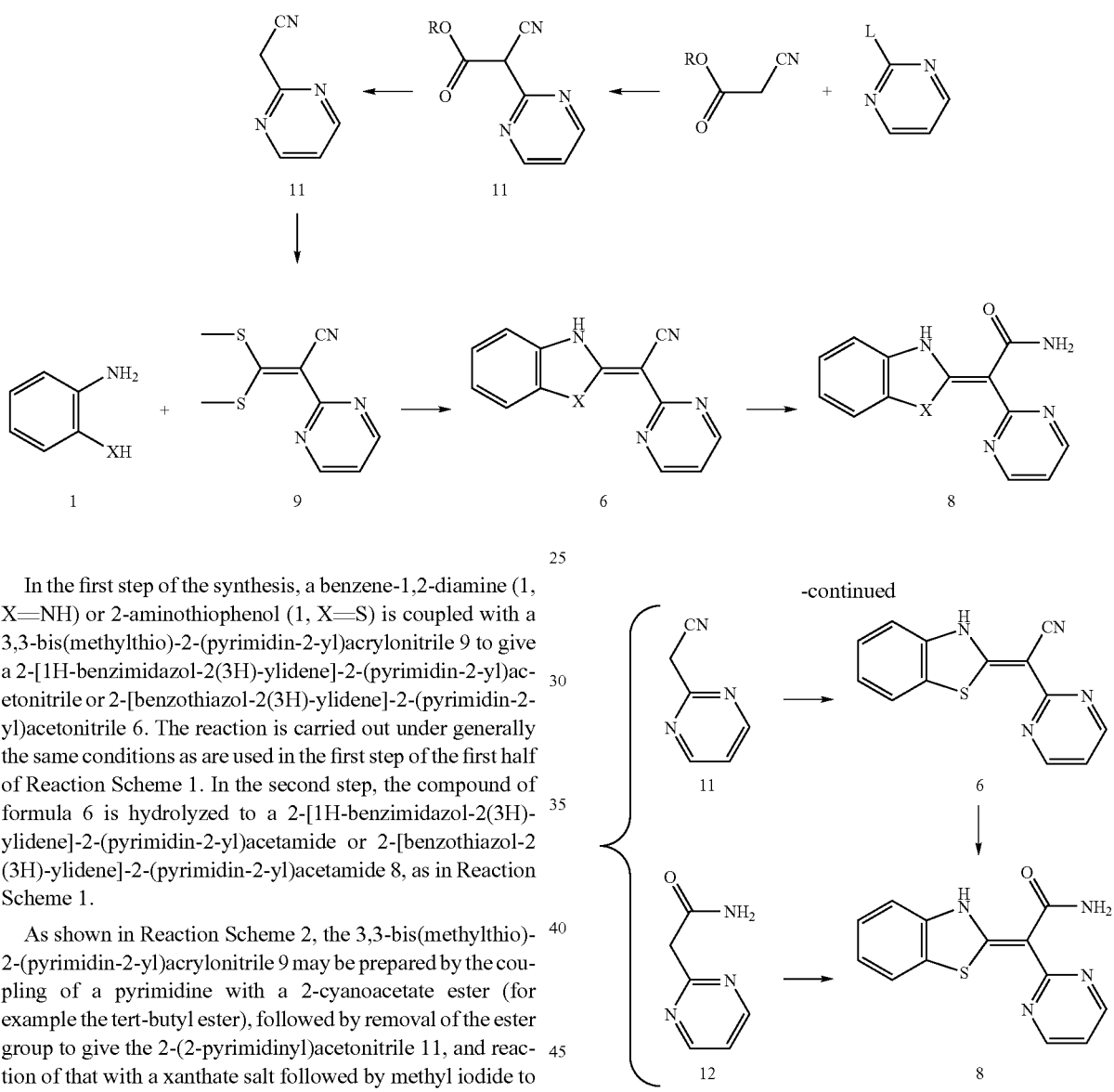

In the first step of the synthesis, a benzene-1,2-diamine (1, X=NH) or 2-aminothiophenol (1, X=S) is coupled with a 3,3-bis(methylthio)-2-(pyrimidin-2-yl)acrylonitrile 9 to give a 2-[1H-benzimidazol-2(3H)-ylidene]-2-(pyrimidin-2-yl)acetonitrile or 2-[benzothiazol-2(3H)-ylidene]-2-(pyrimidin-2-yl)acetonitrile 6. The reaction is carried out under generally the same conditions as are used in the first step of the first half of Reaction Scheme 1. In the second step, the compound of formula 6 is hydrolyzed to a 2-[1H-benzimidazol-2(3H)-ylidene]-2-(pyrimidin-2-yl)acetamide or 2-[benzothiazol-2(3H)-ylidene]-2-(pyrimidin-2-yl)acetamide 8, as in Reaction Scheme 1.

As shown in Reaction Scheme 2, the 3,3-bis(methylthio)-2-(pyrimidin-2-yl)acrylonitrile 9 may be prepared by the coupling of a pyrimidine with a 2-cyanoacetate ester (for example the tert-butyl ester), followed by removal of the ester group to give the 2-(2-pyrimidinyl)acetonitrile 11, and reaction of that with a xanthate salt followed by methyl iodide to give the dithioketal. The preparation of 3,3-bis(methylthio)-2-(4-trifluoromethylpyrimidin-2-yl)acrylonitrile is given in Preparative Example 4.

A third general synthetic method, applicable to the benzothiazole-based compounds, involves the coupling of a 2-(pyrimidin-2-yl)acetonitrile or 2-(pyrimidin-2-yl)acetamide with a 2-chloro-benzothiazole, followed by hydrolysis of the nitrile if necessary, as shown in Reaction Scheme 3.

Reaction Scheme 3

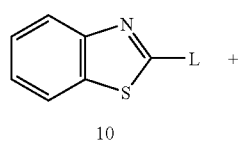

In this synthesis, the benzothiazole 10 [L is a leaving group] is coupled with a 2-(pyrimidin-2-yl)acetonitrile 11 or 2-(pyrimidin-2-yl)acetamide 12 in the presence of a strong base, such as sodium hydride, in an aprotic polar solvent, such as tetrahydrofuran, to give a 2-[benzothiazol-2(3H)-ylidene]-2-(pyrimidin-2-yl)acetonitrile 6 or 2-[benzothiazol-2(3H)-ylidene]-2-(pyrimidin-2-yl)acetamide 8. If the compound of formula 6 has been prepared, it is then hydrolyzed to a compound of formula 8, as in Reaction Scheme 1.

A fourth general synthetic method, also applicable to the benzothiazole-based compounds, also involves coupling of a 2-(pyrimidin-2-yl)acetonitrile or 2-(pyrimidin-2-yl)acetamide, here with a phenyl isothiocyanate, typically formed from an aniline, followed by ring closure and hydrolysis of the nitrile if necessary, as shown in Reaction Scheme 4. This method is particularly attractive for compounds with complex sidechains on the benzene ring of the benzothiazole because the preparation of substituted anilines is well known.

Reaction Scheme 4

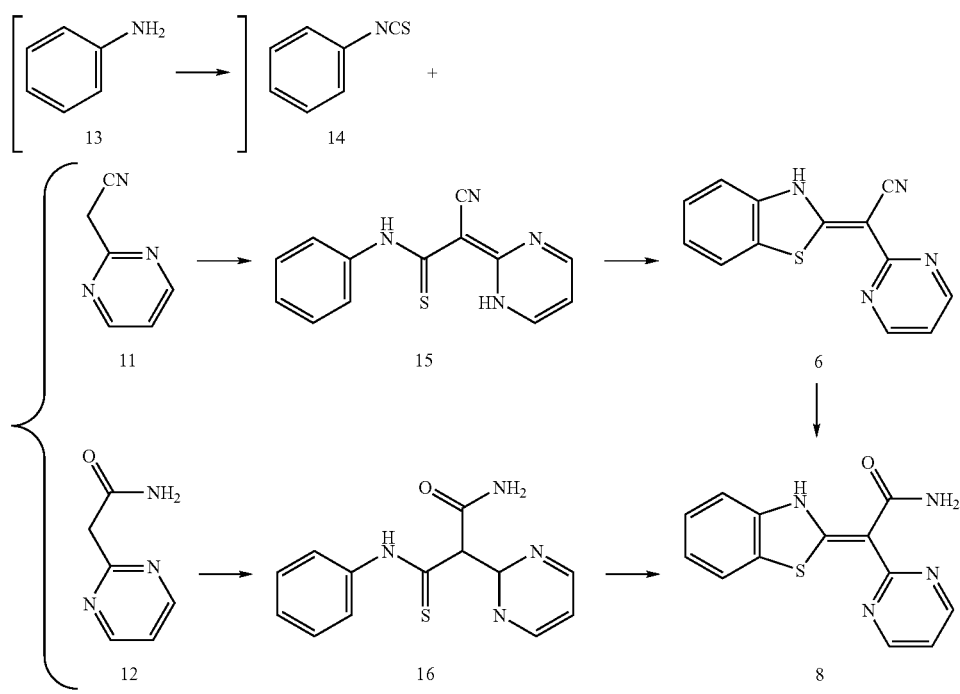

In the first step of the synthesis, the phenyl isothiocyanate 14 (which may be readily prepared by reaction of an aniline with thiophosgene) is coupled with a 2-(pyrimidin-2-yl)acetonitrile 11 or 2-(pyrimidin-2-yl)acetamide 12 in the presence of a base to give a 3-(phenylamino)-2-(pyrimidin-2(1H)-ylidene)-3-thioxo-propionitrile 15 or 3-(phenylamino)-2-(pyrimidin-2-yl)-3-thioxopropanamide 16. In the second step, ring closure of the compound of formula 15 or 16 is achieved by reaction with an agent such as bromine/acetic acid or potassium ferricyanide, to give a 2-[benzothiazol-2(3H)-ylidene]-2-(pyrimidin-2-yl)acetonitrile 6 or 2-[benzothiazol-2(3H)-ylidene]-2-(pyrimidin-2-yl)acetamide 8. If the compound of formula 6 has been prepared, it is then hydrolyzed to a compound of formula 8, as in Reaction Scheme 1.

A fifth general synthetic method, also applicable to the benzothiazole-based compounds, involves the formation of a 2-[benzothiazol-2(3H)-ylidene]malononitrile, followed by conversion of one of the nitrile groups to an imidate and then to an amidine. The amidine is reacted with a β-diketone or equivalent to form the pyrimidine ring, and the other nitrile hydrolyzed to the corresponding carboxamide; or the amidine-nitrile may be hydrolyzed and then reacted with the β-diketone or equivalent, as shown in Reaction Scheme 5. This method is particularly attractive for forming compounds where the substituted pyrimidine is not available as a starting material.

Reaction Scheme 5

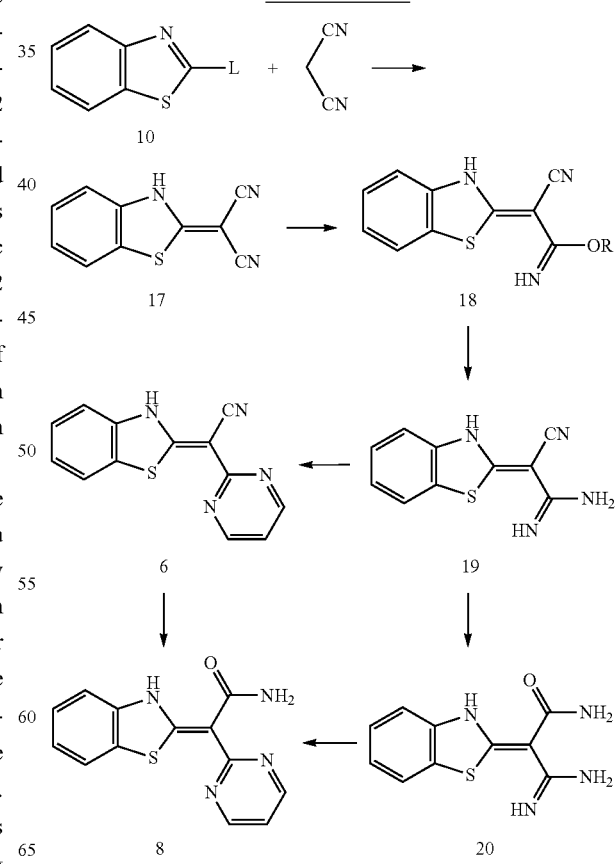

In the first step, the benzothiazole 10 [L is a leaving group, as in Reaction Scheme 4] reacts with malononitrile in the presence of a strong base, such as sodium ethoxide in ethanol, to give the 2-[benzothiazol-2(3H)-ylidene]malononitrile 17. Reaction of this nitrile in suspension in a polar solvent with gaseous hydrogen chloride gives the 2-[benzothiazol-2(3H)-ylidene]-2-cyanoacetimidate 18, and reaction of the imidate with ammonia gives the corresponding 2-[benzothiazol-2 (3H)-ylidene]-2-cyanoacetamidine 19. Compound 19 is then reacted with a β-diketone or equivalent, such as 2,4-pentanedione or ethyl 3-oxo-4,4,4-trifluorobutyrate, to form the pyrimidine ring [substituents not shown] of the compound of formula 6, in the presence of a base such as sodium ethoxide in an aprotic solvent under strong (e.g. microwave) heating. Finally, the compound of formula 6 is hydrolyzed to a compound of formula 8, as in Reaction Scheme 1. If the order is reversed, so that the hydrolysis is performed before the coupling, the hydrolysis proceeds as in Reaction Scheme 1, and the coupling may take place under milder conditions.

Compounds of formula A may be converted to salts by reaction with the appropriate acids, using techniques well known to a person of ordinary skill in the art for the formation of acid addition salts. The acid used, and the reaction conditions, may be chosen to give salts that are pharmaceutically acceptable and that have a form convenient for isolation and formulation, such as a solid form (for example, amorphous or crystalline).

Compounds for a Use, Compositions, and Uses

The second aspect of this invention is the compounds of the first aspect of this invention for use as kinase inhibitors, especially as an inhibitor of Aurora kinase and optionally VEGFR2 kinase, particularly for the treatment of cancer. The third aspect of this invention is pharmaceutical compositions comprising a compound of the first aspect of this invention and optionally a pharmaceutically acceptable excipient. The fourth aspect of this invention is the use of the compounds of the first aspect of this invention as kinase inhibitors; and the fifth aspect of this invention is the use of the compounds in the manufacture of medicaments for kinase inhibition, especially for the treatment of cancer.

The compounds of the first aspect of this invention may be administered by any route suitable to the subject being treated and the nature of the subject's condition. Routes of administration include administration by injection, including intravenous, intraperitoneal, intramuscular, and subcutaneous injection, by transmucosal or transdermal delivery, through topical applications, nasal spray, suppository and the like or may be administered orally. Formulations may optionally be liposomal formulations, emulsions, formulations designed to administer the drug across mucosal membranes or transdermal formulations. Suitable formulations for each of these methods of administration may be found, for example, in *Remington: The Science and Practice of Pharmacy*, 20th ed., A. Gennaro, ed., Lippincott Williams & Wilkins, Philadelphia, Pa., U.S.A. Typical formulations will be either oral or solutions for intravenous infusion. Typical dosage forms will be tablets or capsules for oral administration, solutions for intravenous infusion, and lyophilized powders for reconstitution as solutions for intravenous infusion.

Depending on the intended mode of administration, the pharmaceutical compositions may be in the form of solid, semi-solid or liquid dosage forms, preferably in unit dosage form suitable for single administration of a precise dosage. In addition to an effective amount of the active compound(s), the compositions may contain suitable pharmaceutically-acceptable excipients, including adjuvants which facilitate processing of the active compounds into preparations which can be used pharmaceutically. "Pharmaceutically acceptable excipient" refers to an excipient or mixture of excipients which does not interfere with the effectiveness of the biological activity of the active compound(s) and which is not toxic or otherwise undesirable to the subject to which it is administered.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in water or an aqueous excipient, such as, for example, water, saline, aqueous dextrose, and the like, to form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

For oral administration, the composition will generally take the form of a tablet or capsule, or it may be an aqueous or nonaqueous solution, suspension or syrup. Tablets and capsules are preferred oral administration forms. Tablets and capsules for oral use will generally include one or more commonly used excipients such as lactose and corn starch. Lubricating agents, such as magnesium stearate, are also typically added. When liquid suspensions are used, the active agent may be combined with emulsifying and suspending excipients. If desired, flavoring, coloring and/or sweetening agents may be added as well. Other optional excipients for incorporation into an oral formulation include preservatives, suspending agents, thickening agents, and the like.

Injectable formulations can be prepared in conventional forms, either as liquid solutions or suspensions, solid forms suitable for solubilization or suspension in liquid prior to injection, or as emulsions or liposomal formulations. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media.

The pharmaceutical compositions of this invention may also be formulated in lyophilized form for parenteral administration. Lyophilized formulations may be reconstituted by addition of water or other aqueous medium and then further diluted with a suitable diluent prior to use. The liquid formulation is generally a buffered, isotonic, aqueous solution. Examples of suitable diluents are isotonic saline solution, 5% dextrose in water, and buffered sodium or ammonium acetate solution. Pharmaceutically acceptable solid or liquid excipients may be added to enhance or stabilize the composition, or to facilitate preparation of the composition.

Typically, a pharmaceutical composition of the present invention is packaged in a container with a label, or instructions, or both, indicating use of the pharmaceutical composition in the treatment of cancer.

The pharmaceutical composition may additionally contain one or more other pharmacologically active agents in addition to a compound of this invention. These additional active agents will typically be useful in treating cancer, or for enhancing the treatment of cancer by compounds of this invention.

Methods of Using the Compounds

The compounds of the first aspect of this invention have activity against human cancer cell lines, as demonstrated in the in vitro and in vivo Examples below, and are therefore considered to be useful as human cancer chemotherapeutic agents, for the treatment of human cancers.

Thus, the sixth aspect of this invention includes methods of treating cancer in humans by administering a therapeutically effective amount of a compound of the first aspect of this invention, or a pharmaceutical composition of the third aspect of this invention, to the human. Optionally, the methods further comprise treating the human with another anticancer therapy, such as a therapy already conventional for the cancer being treated.

Cancers that are particularly treatable by the method of this invention are cancers with sensitivity to Aurora kinase inhibitors and also to inhibitors of angiogenesis (such as to VEGFR2 kinase inhibitors), and especially those cancers that overexpress one or more Aurora kinases. Such cancers include those mentioned in the "Background of the Invention" section above and the documents cited therein. Cancers particularly treatable by the method of this invention include solid malignancies such as colorectal, lung, breast, ovarian, pancreatic, bladder, brain, gastrointestinal, and kidney cancers, and hematological malignancies, such as leukemias, especially ALL and CML, lymphomas, and myelodysplastic syndrome.

The amount of the compound of the first aspect of this invention that is administered to the human (either alone or, more usually, in a composition of the third aspect of this invention) should be a therapeutically effective amount when used alone or when used in conjunction with the another anticancer therapy (if the compound of the first aspect of this invention is administered in conjunction with another anticancer therapy); and similarly the amount of the another anticancer therapy that is administered to the human (if the compound of the first aspect of this invention is administered in conjunction with another anticancer therapy) should be a therapeutically effective amount when used in conjunction with the compound of the first aspect of this invention. However, the therapeutically effective amount of either the compound of the first aspect of this invention and the amount of the another anticancer therapy when administered in combination cancer chemotherapy may each be less than the amount which would be therapeutically effective if delivered to the human alone. It is common in cancer therapy, though, to use the maximum tolerated dose of the or each therapy, with a reduction only because of common toxicity of the therapies used or potentiation of the toxicity of one therapy by another.

The compounds of the first aspect of this invention, or pharmaceutical compositions of the third aspect of this invention, are thus used to treat cancer in humans requiring such treatment, by administering a therapeutically effective amount of the chosen compound or composition. Therapeutically effective amounts of compounds of the invention are in the range of 10-10,000 mg/m$^2$, for example, 30-3000 mg/m$^2$ or 100-1000 mg/m$^2$. Dosing may be at 1-35 day intervals; for example, about 500-1000 mg/m$^2$ at 1-5 week intervals, especially at 1, 2, 3, or 4 week intervals, or at higher frequencies including as frequently as once/day for several (e.g. 5 or 7) days, with the dosing repeated every 2, 3, or 4 weeks, or constant infusion for a period of 6-72 hours, also with the dosing repeated every 2, 3, or 4 weeks. Suitable dosages and dose frequencies will be readily determinable by a person of ordinary skill in the art having regard to that skill and this disclosure. No unacceptable toxicological effects are expected when compounds of the invention are administered in accordance with the present invention.

A person of ordinary skill in the art of cancer therapy will be able to ascertain a therapeutically effective amount of the compound of the first aspect of this invention and a therapeutically effective amount of another anticancer therapy (if the compound of the first aspect of this invention is administered as a part of a chemotherapeutic combination) for a given cancer and stage of disease without undue experimentation and in reliance upon personal knowledge and the disclosure of this application.

EXAMPLES

The following examples illustrate the preparation of compounds of this invention, and their activity in predictive in vitro and in vivo anticancer assays.

Preparative and Synthetic Examples

The compounds of this invention are prepared by conventional methods of organic chemistry. See, for example, Larock, "Comprehensive Organic Transformations", Wiley-VCH, New York, N.Y., U.S.A. In some cases, protective groups may be introduced and later removed. Suitable protective groups are described in Greene et al. "Protective Groups in Organic Synthesis", 2nd ed., 1991, John Wiley and Sons, New York, N.Y., U.S.A. The compounds of this invention can be synthesized, generally following the synthetic schemes illustrated earlier in this application, as shown in the following examples or by modifying the exemplified syntheses by means known to those of ordinary skill in the art. Preparative examples refer to the preparation of intermediates useful in the synthesis of compounds of this invention; synthesis examples refer to the synthesis of compounds of this invention. Compound numbers refer to the table immediately following these examples.

Preparative Example 1

Preparation of
N-ethyl-3-(4-morpholinyl)propan-1-amine, a
sidechain intermediate for compound 41A 3-(4-Morpholinyl)propan-1-amine (35.0 g, 243 mmol) was dissolved in tetrahydrofuran (THF, 250 mL), di-tert-butyl dicarbonate (58.0 g, 266 mmol) and N,N-diisopropylethylamine (DIPEA, 84 mL, 484 mmol) were added, and the solution was stirred overnight. The solvent was removed and the residue partitioned between ethyl acetate (EA) and 1.2M hydrochloric acid (300 mL). The pH was raised to 7 with saturated aqueous sodium bicarbonate and the layers separated. The aqueous layer was extracted twice with EA (150 mL each), and the EA layers were combined, washed with brine, and dried over magnesium sulfate. The solvent was removed, giving tert-butyl 3-(4-morpholinyl)propylcarbamate (39 g). Tent-butyl 3-(4-morpholinyl)propylcarbamate (3.5 g, 14.3 mmol) was dissolved in THF (30 mL), and sodium hydride (60% dispersion in mineral oil, 1.03 g, 25.8 mmol) was added in portions. After stirring for 5 min, ethyl iodide (13.4 g, 86.0 mmol) was added and the mixture was heated to 60° C. for 7 hr then stirred at room temperature overnight. Water (5 mL) was added and the solvent removed. The residue was dissolved in EA, and the solution was washed with brine, dried over magnesium sulfate, and the solvent removed to give crude tert-butyl ethyl[3-(4-morpholinyl)propyl]carbamate (2.5 g). Purification by silica gel chromatography eluting with 92:8 dichloromethane/methanol (DCM/MeOH) gave purified tert-butyl ethyl[3-(4-morpholinyl)propyl]carbamate (1.4 g). Purified tert-butyl ethyl[3-(4-morpholinyl)propyl]carbamate (350 mg, 1.3 mmol) was dissolved in 4.0M hydrogen chloride in dioxane (5 mL, 20 mmol) and stirred for 45 min. Water was added and the solution made basic with 2M aqueous sodium hydroxide. The product was extracted into EA, and the EA extract washed with brine and dried over magnesium sulfate. Removal of the EA gave N-ethyl-3-(4-morpholinyl)propan-1-amine (50 mg).

Preparative Example 2

Preparation of 4-trifluoromethyl-2-methylthio-6-(pyridin-2-yl)-pyrimidine, an intermediate to compound 11A by Reaction Scheme 1

To a solution of 4,4,4-trifluoro-1-(pyridin-2-yl)butane-1,3-dione (1.0 g, 4.6 mmol) in ethanol (10 mL) was added 2-methyl-2-thiopseudourea sulfate (0.64 g, 4.6 mmol), followed by sodium ethoxide (3.0 mL of 21 wt. % solution in ethanol, 9 mmol). The mixture was heated at reflux for 9 h, then cooled to room temperature and extracted with EA. The EA was washed with water and the solvent removed under reduced pressure. The crude product was purified by column chromatography, eluting with 49:1 chloroform/MeOH, to give 4-trifluoromethyl-2-methylthio-6-(pyridin-2-yl)pyrimidine (0.21 g, 17% yield) as an off-white solid.

Preparative Example 3

Preparation of (2-chloro-4-trifluoromethylpyrimidin-5-yl)-(4-methylpiperazin-1-yl)methanone, an intermediate to compound 130A by Reaction Scheme 1

N-Methylpiperazine (0.11 mL, 1 mmol) was added to a solution of 2-chloro-4-trifluoromethyl-pyrimidine-5-carbonyl chloride (0.24 g, 1 mmol) in DCM (4 mL) at 0° C. The mixture was stirred at that temperature for 1 hr, and the solvent was then removed under vacuum to give (2-chloro-4-trifluoromethylpyrimidin-5-yl)(4-methylpiperazin-1-yl)methanone as a solid.

Other 2-chloro-substituted pyrimidines, intermediates to compounds 131A to 136A, were similarly prepared.

Preparative Example 4

Preparation of 3,3-bis(methylthio)-2-[(4-trifluoromethylpyrimidin-2-yl)acrylonitrile, an intermediate in Reaction Scheme 2 tert-Butyl 2-cyano-2-[4-trifluoromethylpyrimidin-2 (1H)-ylidene]acetate. tert-Butyl 2-cyanoacetate (97.45 g, 690 mmol) was dissolved in anhydrous THF (1 L), and cooled on an ice-bath for 90 min with stirring under nitrogen. A 1M solution of lithium hexamethyldisilazane in THF (690 mL, 690 mmol) was added dropwise. The mixture was stirred for an additional 1 hr, then 2-chloro-4-trifluoromethylpyrimidin (105 g, 590 mmol) was added dropwise. The mixture was then heated to 50° C. for 3 hr with stirring under nitrogen, allowed to cool, and the solvent removed under reduced pressure. Hydrochloric acid (1N) was added to the residue to achieve a pH of 1-2. The precipitated solids were collected by filtration and dried under vacuum to give tert-butyl 2-cyano-2-[4-trifluoromethylpyrimidin-2(1H)-ylidene]acetate (135 g, 82% yield) as a bright yellow solid, >98% pure by LC/MS. tert-Butyl 2-cyano-2-[4-trifluoromethylpyrimidin-2(1H)-ylidene]acetate (48 g; 166 mmol) was suspended in 4M hydrogen chloride in dioxane (415 mL, 1.66 mol) and the mixture stirred at room temperature for 6 hr, then concentrated under reduced pressure to give 2-(4-trifluoromethylpyrimidin-2-yl)acetonitrile (31 g, 100% yield) as an orange oil, >98% pure by LC/MS. To a stirred solution of 2-(4-trifluoromethylpyrimidin-2-yl)acetonitrile (31.0 g; 166 mmol) in absolute ethanol (800 mL) was added potassium O-ethylxanthate (26.6 g; 166 mmol) followed by potassium carbonate (45.8 g; 332 mmol). The mixture was heated to 100° C. for 3 hr, cooled to room temperature, iodomethane (47.1 g; 332 mmol) added dropwise, and 1N hydrochloric acid (2 L) added. The resulting mixture was extracted with DCM (1.5 L), and the DCM layer was washed twice with brine (1 L each). The solvent was removed under reduced pressure to give 3,3-bis(methylthio)-2-(4-trifluoromethylpyrimidin-2-yl)acrylonitrile (36 g, 75% yield) as a light brown solid, >95% pure by LC/MS.

Preparative Example 5

Preparation of 4-[(1H-imidazol-1-yl)methyl]benzene-1,2-diamine, and intermediate to compound 90A by Reaction Scheme 1 or 2

Potassium carbonate (1.18 g, 8.54 mmol) was added to a stirred solution of 4-(bromomethyl)-2-fluoro-1-nitrobenzene (2.0 g, 8.55 mmol) and imidazole (584 mg, 8.58 mmol) in acetonitrile (40 mL), the mixture stirred at room temperature for 3.5 h, the solvent removed under reduced pressure, and the residue partitioned between water and EA. The aqueous layer was extracted three times with EA, then the combined EA layers were extracted three times with 1M hydrochloric acid. The pH of the combined aqueous layers was adjusted to 8 with 5M aqueous sodium hydroxide, and the resulting milky solution was extracted three times with EA. The EA layers were combined, washed with brine, and dried over magnesium sulfate. Filtration and concentration gave 1-(3-fluoro-4-nitrobenzyl)-1H-imidazole (914 mg), which contained about 15% of a bis-alkylated imidazole byproduct. 1-(3-Fluoro-4-nitrobenzyl)-1H-imidazole (914 mg) was treated with an ethanolic ammonia solution (2M $NH_3$, 55 mL) in a sealed tube heated to 80° C. for 2 days. After cooling, the solvent was removed to give 5-[(1H-imidazol-1-yl)methyl]-2-nitrobenzeneamine (1.0 g) as an orange solid. 5-[(1H-Imidazol-1-yl)methyl]-2-nitrobenzeneamine (1.0 g, 4.77 mmol) was dissolved in a 10% solution of dimethylformamide in ethanol (44 mL), and 10% palladium on carbon (130 mg, 0.12 mmol) was added. The solution was degassed and stirred under a hydrogen atmosphere using a balloon for 1 day. Following degassing, the solution was diluted with MeOH and filtered through diatomaceous earth, giving 4-[(1H-imidazol-1-yl)methyl]benzene-1,2-diamine (1.08 g) as a brown oil.

Preparative Example 6

Preparation of N-(3,4-diaminophenyl)-2-(1H-imidazol-1-yl)acetamide, an intermediate to compound 86A by Reaction Scheme 1 or 2

To a solution of 1H-imidazole-1-ylacetic acid (284 mg, 2.25 mmol) and 2-nitrobenzene-1,4-diamine (324 mg, 2.12 mmol) in acetonitrile (20 mL) was added 3-diethoxyphosphoryloxy-1,2,3-benzotriazin-4(3H)-one (DEPBT, 632 mg, 2.11 mmol) and triethylamine (600 µL, 4.4 mmol). The mixture was stirred for 4 d at room temperature. The red precipitate was collected by filtration and washed with acetonitrile to give N-(4-amino-3-nitrophenyl)-2-(1H-imidazol-1-yl)acetamide (430 mg, 88% yield), 98% pure. A solution of N-(4-amino-3-nitrophenyl)-2-(1H-imidazol-1-yl)acetamide (430 mg, 1.65 mmol) in ethanol (20 mL) was hydrogenated at atmospheric pressure with 10% palladium on carbon (100 mg, 0.09 mmol) at room temperature overnight. The mixture was filtered, giving a blue solution. Removal of the solvent under reduced pressure gave N-(3,4-diaminophenyl)-2-(1H-imidazol-1-yl)acetamide (413 mg) as a blue semi-solid.

Preparative Example 7

Preparation of
N-(3,4-diaminophenyl)-2-(diethylamino)acetamide,
an intermediate to compound 75A by Reaction
Scheme 1 or 2

2-Nitrobenzene-1,4-diamine (1.55 g, 10.1 mmol), N,N-diethylglycine sodium salt (1.61 g, 10.6 mmol) and DEPBT (3.02 g, 10.0 mmol) were suspended in acetonitrile (75 mL). Triethylamine (2.8 mL, 20.0 mmol) was added and the solution stirred overnight at room temperature. The brown precipitate which was formed was filtered and discarded. The filtrate was concentrated and the residue partitioned between EA and saturated aqueous sodium bicarbonate. The organic phase was washed with water and then with brine, dried over sodium sulfate, and the solvent removed under reduced pressure. The residue was dissolved in ethanol (50 mL) and hydrogenated at atmospheric pressure with 10% palladium on charcoal (1.0 g, 0.9 mmol) at room temperature overnight. Filtration and concentration under reduced pressure gave N-(3,4-diaminophenyl)-2-(diethylamino)acetamide as a light brown semi-solid, which solidified and turned blue on standing.

Preparative Example 8

Preparation of 4-(pyridin-3-yl)-benzene-1,2-diamine,
an intermediate to compound 107A by Reaction
Scheme 1 or 2

4-Amino-3-nitrophenylboronic acid pinacol ester (1.60 g, 6.06 mmol), 3-bromopyridine (1.10 g, 6.96 mmol), cesium carbonate (3.33 g, 10.22 mmol) and 1,1'-bis(diphenylphosphino)ferrocene-palladium(II) dichloride DCM complex (491 mg, 0.60 mmol) were suspended in dimethylformamide (20 mL). The solution was degassed by vacuum several times and placed in an argon atmosphere. It was then heated to 65° C. for 6 hr. After cooling, EA (100 mL) and water (40 mL) were added. When additional water (50 mL) was added to the organic layer, a precipitate was formed in the separatory funnel. The biphasic solution was filtered, and the filtrate was transferred to the separatory funnel and separated. The organic phase was washed twice with water (50 mL each), then with brine, and then dried with sodium sulfate and concentrated under reduced pressure to give 2-nitro-4-(pyridin-3-yl)benzenamine (1.18 g). 2-Nitro-4-(pyridin-3-yl)benzenamine (700 mg, 3.26 mmol) in 1:1 ethanol/EA (40 mL) was hydrogenated at atmospheric pressure with 10% palladium on carbon (90 mg, 0.08 mmol) at room temperature for 2 days. Filtration and concentration under reduced pressure gave 4-(pyridin-3-yl)-benzene-1,2-diamine (621 mg).

Preparative Example 9

Preparation of N-(3,4-diaminophenyl)-2-(diethylamino)-N-ethylacetamide, an intermediate to compound 139A by Reaction Scheme 1 or 2

A solution of 2-nitrobenzene-1,4-diamine (2.00 g; 13.1 mmol), di-tert-butyl dicarbonate (3.14 g, 14.4 mmol), and DIPEA (2.6 mL; 14.9 mmol) in dioxane (40 mL) was heated at reflux for 40 min, then allowed to cool to room temperature. The mixture was concentrated under reduced pressure and taken up in EA (100 mL). The EA solution was washed with water and the aqueous phase extracted with EA. The combined organic layers were washed with saturated aqueous sodium bicarbonate and brine, dried over magnesium sulfate, and concentrated under reduced pressure to give tert-butyl 3-amino-4-nitrophenylcarbamate in quantitative yield as a brown solid. To a stirred solution of tert-butyl 3-amino-4-nitrophenylcarbamate (2.74 g; 10.8 mmol) in anhydrous THF (50 mL) was added sodium hydride (0.868 g of a 60 wt % dispersion in oil, 21.7 mmol) in portions over 10 min. The mixture was stirred for a further 5 min at room temperature and then iodoethane (950 µL; 11.9 mmol) was added. The solution was stirred for 20 hr, water (1 mL) was added, and the solution concentrated under reduced pressure. The residue was partitioned between EA and water and the phases separated. The aqueous phase was extracted twice with EA and the combined organic phases washed with water, saturated aqueous sodium bicarbonate and brine. The organic solution was dried over magnesium sulfate and concentrated under reduced pressure to give a mixture of mono- and di-ethylated products (2.18 g). This was purified by silica gel column chromatography eluting with 1:4 EA/hexanes to give tert-butyl 4-amino-3-nitrophenyl(ethyl)carbamate (0.534 g) as an orange solid. A solution of tert-butyl 4-amino-3-nitrophenyl(ethyl)carbamate (0.514 g; 1.83 mmol) in 4M hydrogen chloride in dioxane (10 mL) was stirred at ambient temperature for 3 hr. The solvent was removed under reduced pressure and the residue dissolved in water. The pH was adjusted to 10 with 1M aqueous sodium hydroxide and the aqueous phase was extracted three times with EA. The combined organic extracts were washed with brine, dried over magnesium sulfate, and concentrated under reduced pressure to give $N^1$-ethyl-3-nitrobenzene-1,4-diamine (0.311 g) as a purple solid. $N^1$-Ethyl-3-nitrobenzene-1,4-diamine (0.208 g; 1.38 mmol) was dissolved in acetonitrile (10 mL) and N,N-diethylglycine sodium salt (0.192 g; 1.25 mmol) and DEPBT (0.375 g; 1.25 mmol) were added, followed by triethylamine (577 µL; 4.14 mmol). The mixture was stirred at room temperature for 8 hr; and then further quantities of N,N-diethylglycine sodium salt (0.192 g; 1.25 mmol), DEPBT (0.375 g; 1.25 mmol), and triethylamine (577 µL; 4.14 mmol) were added and stirring continued for 63 hr. Solids were removed by filtration and the filtrate concentrated under reduced pressure. Water was added to the residue and the pH was adjusted to 10 with saturated aqueous sodium bicarbonate. This solution was extracted three times with EA, and the organic extracts combined, washed with water and brine, dried over magnesium sulfate, and concentrated under reduced pressure to give N-(4-amino-3-nitrophenyl)-2-(diethylamino)-N-ethylacetamide (0.303 g) as a brown oil. A solution of N-(4-amino-3-nitrophenyl)-2-(diethylamino)-N-ethylacetamide (0.092 g; 0.31 mmol) in ethanol (5 mL) was hydrogenated at atmospheric pressure with 10% palladium on carbon (11 mg) at room temperature for 22 hr. The mixture was filtered through diatomaceous earth, washing with ethanol, and the filtrate was concentrated under reduced pressure to give N-(3,4-diaminophenyl)-2-(diethylamino)-N-ethylacetamide in quantitative yield as a brown oil.

Preparative Example 10

Preparation of 4-(4-methylpiperazin-1-yl)benzene-1,2-diamine, an intermediate to compound 119A by Reaction Scheme 1 or 2

A solution of 5-fluoro-2-nitrobenzenamine (3.0 g, 18.1 mmol), triethylamine (5.0 mL, 36.3 mmol), and 1-methylpiperazine (2.0 mL, 18.1 mmol) in dioxane (25 mL) was heated at reflux for 18 hr. After cooling to room temperature, the mixture was concentrated under reduced pressure and the residue dissolved in DCM (100 mL). This solution was washed with saturated aqueous sodium bicarbonate followed by brine, then dried over magnesium sulfate and concentrated under reduced pressure to give 5-(4-methylpiperazin-1-yl)-2-nitrobenzenamine (3.25 g) as a dark brown solid. A solution of 5-(4-methylpiperazin-1-yl)-2-nitrobenzenamine (3.25 g; 13.7 mmol) in absolute ethanol (40 mL) was hydrogenated at atmospheric pressure with 10% palladium on carbon (0.30 g; 2.7 mmol) at room temperature for 17 hr. The mixture was filtered through diatomaceous earth and concentrated under reduced pressure to give 4-(4-methylpiperazin-1-yl)benzene-1,2-diamine (2.36 g).

Preparative Example 11

Preparation of 4-[2-(1H-imidazol-1-yl)ethoxy]benzenamine, an intermediate to compound 117A by Reaction Scheme 4

1-(Hydroxyethyl)imidazole (5.30 g; 47.3 mmol) was dissolved in anhydrous THF (50 mL) and cooled in an ice-bath. Sodium hydride (2.08 g of a 60 wt % dispersion in oil, 52.0 mmol) was added in portions over 10 min. The ice-bath was removed, and the mixture was stirred at room temperature for 20 min. A solution of 1-fluoro-4-nitrobenzene (5.0 mL, 47.2 mmol) in anhydrous THF (10 mL) was added over 5 min and the mixture stirred for a further 1.5 hr. Water (a few mL) was cautiously added and the mixture concentrated under reduced pressure. The residue was partitioned between EA (75 mL) and water (75 mL), and the phases separated. The aqueous phase was extracted twice with EA and the combined organic layers extracted three times with 1N hydrochloric acid. The pH of these acidic extracts was then adjusted to 7 with 5N aqueous sodium hydroxide and the resulting milky solution extracted three times with EA. The combined organic extracts were washed with water and brine, then dried over magnesium sulfate and concentrated under reduced pressure to give 1-(2-(4-nitrophenoxy)-ethyl)-1H-imidazole (5.46 g) as a brown oil. A solution of 1-(2-(4-nitrophenoxy)ethyl)-1H-imidazole (5.46 g; 2.34 mmol) in ethanol (60 mL) was hydrogenated at atmospheric pressure with 10% palladium on carbon (0.40 g) at room temperature for 20 hr. The mixture was filtered through diatomaceous earth and then concentrated under reduced pressure to give 4-[2-(1H-imidazol-1-yl)ethoxy]benzenamine (4.56 g) as a white solid.

4-[3-(4-methylpiperazin-1-yl)propoxy]benzenamine was similarly prepared using 1-(3-hydroxypropyl)-4-methylpiperazine; 4-[2-(4-methylpiperazin-1-yl)ethoxy]benzenamine was similarly prepared using 1-(2-hydroxyethyl)-4-methylpiperazine; 4-[2-(4-morpholin-1-yl)ethoxy]benzenamine was similarly prepared using 4-(2-hydroxyethyl)morpholine; and 4-[2-(dimethylamino)ethoxy]benzenamine was similarly prepared using 2-(dimethylamino)ethanol. Other anilines with oxygen-linked sidechains may be similarly prepared; in some cases, for example, the preparation of 4-(pyridin-3-yloxy)-benzenamine from 3-hydroxypyridine and the preparation of 4-[3-(4-morpholin-1-yl)propoxy]-benzenamine from 4-(3-hydroxypropyl)morpholine, less stringent reaction conditions, such as the use of potassium carbonate as the base, were found to be sufficient. 3-[2-(4-Morpholin-1-yl)ethoxy]-benzenamine was prepared using 3-nitrophenol and 4-(2-chloroethyl)morpholine, with cesium carbonate as the base; and other anilines with oxygen-linked sidechains may be similarly prepared.

Preparative Example 12

Preparation of 4-[4-(piperidin-1-yl)piperidin-1-yl]benzenamine, an intermediate to compound 121A by Reaction Scheme 4

A solution of 1-fluoro-4-nitrobenzene (1.3 mL, 12.3 mmol), triethylamine (6.0 mL; 43.0 mmol) and 4-(piperidin-1-yl)piperidine (2.36 g; 14.0 mmol) in dioxane (10 mL) was heated at reflux for 18 hr. After cooling to room temperature the mixture was concentrated under reduced pressure and the residue dissolved in DCM (150 mL). The DCM solution was washed with saturated aqueous sodium bicarbonate and brine, then dried over magnesium sulfate and concentrated under reduced pressure to produce a yellow solid. Hexanes were added and the suspension briefly sonicated. The solid was collected by filtration and washed with hexanes to give 1-(4-nitrophenyl)-4-(piperidin-1-yl)piperidine (3.05 g) as a yellow solid. A solution of 1-(4-nitrophenyl)-4-(piperidin-1-yl)piperidine (3.05 g; 10.5 mmol) in ethanol (20 mL) was hydrogenated at atmospheric pressure with 10% palladium on carbon (0.251 g) at room temperature for 17 hr. The mixture was filtered through diatomaceous earth and concentrated under reduced pressure to give 4-[4-(piperidin-1-yl)piperidin-1-yl]benzenamine (2.01 g) as a purple/pink solid.

4-[4-(Morpholin-4-yl)piperidin-1-yl]benzenamine was similarly prepared from 4-(morpholin-1-yl)piperidine; 4-(4-methylpiperazin-1-yl)benzenamine was similarly prepared from 1-methylpiperazine; and $N^1$-methyl-$N^1$-[2-(piperidine-1-yl)ethyl]benzene-1,4-diamine was similarly prepared from N-methyl-2-(piperidine-1-yl)ethanamine. Other anilines with nitrogen-linked sidechains may be similarly prepared, generally with primary or secondary nitrogens, such as those on the sidechains of compounds 123A and 124A, protected with a group such as tert-butoxycarbonyl after the initial coupling with the 1-fluoro-4-nitrobenzene and the protecting group removed prior to the final hydrolysis step of the synthesis in which the resulting anilines are used.

Preparative Example 13

Preparation of 4-[(1H-imidazol-1-yl)methyl]benzenamine, an intermediate to compound 89A by Reaction Scheme 4

Potassium carbonate (2.00 g; 14.6 mmol) was added to a stirred solution of 1-(bromomethyl)-4-nitrobenzene (3.20 g; 14.8 mmol) and imidazole (1.00 g; 14.7 mmol) in acetonitrile (60 mL). The mixture was stirred at room temperature for 17 hr and then concentrated under reduced pressure. The residue was partitioned between EA and water and the phases separated. The aqueous phase was extracted twice with EA; and the combined organic layers washed with water and brine, dried over magnesium sulfate, and concentrated under reduced pressure to give 1-(4-nitrobenzyl)-1H-imidazole (1.27 g) as a red/brown oil. A solution of 1-(4-nitrobenzyl)-1H-imidazole (2.67 g; 13.1 mmol) in ethanol (100 mL) was hydrogenated at atmospheric pressure with 10% palladium on carbon (0.285 g) at room temperature for 4.5 hr. The mixture was filtered through diatomaceous earth and then concentrated under reduced pressure to give 4-[(1H-imidazol-1-ylmethyl]benzenamine (2.24 g) as a white solid.

4-[(Morpholin-4-ylmethyl]benzenamine was similarly prepared from morpholine, and 4-[(4-methylpiperazin-1-ylmethyl]benzenamine was similarly prepared from 1-methylpiperazine. Other anilines with methylene-linked sidechains may be similarly prepared, generally with primary or secondary nitrogens, such as those on the sidechain of compound 94A, protected with a group such as tert-butoxycarbonyl after the initial coupling with the 1-fluoro-4-nitrobenzene and the protecting group removed prior to the final hydrolysis step of the synthesis in which the resulting anilines are used. Similarly, other anilines with ethylene-linked sidechains, such as the sidechain of compound 95A, may be similarly prepared using starting materials such as 1-(2-bromoethyl)-4-nitrobenzene.

Anilines with other sidechains will be readily prepared by a person having ordinary skill in the art having regard to that skill and this disclosure, and will be usable in the syntheses of Reaction Scheme 4. For example, diethyl (4-nitrobenzyl)phosphonate was reacted in a Wittig reaction with pyridin-3-carboxaldehyde and the resulting 3-(4-nitrostyryl)pyridine hydrogenated to give 4-[2-(pyridin-3-yl)ethyl]benzenamine, used to synthesize compound 99A, and the anilines used to synthesize compounds 97A and 98A were similarly prepared; 4-nitrobenzaldehyde was reacted with glyoxal and ammonia to give 2-(4-nitrophenyl)-1H-imidazole, which was N-methylated with methyl iodide and then reduced with stannous chloride to give 4-(1-methyl-1H-imidazol-2-yl)benzenamine, used to synthesize compound 106A; 2-fluoro-4-nitrobenzoic acid was converted to the corresponding benzoyl chloride with oxalyl chloride, then reacted with 3-(morpholin-4-yl)propan-1-amine and reduced to give 4-amino-2-fluoro-N-[3-(morpholin-4-yl)propyl]benzamide, used to synthesize compound 50A; and 4-nitrobenzenesulfonyl chloride was reacted with 2-(morpholin-4-yl)ethan-1-amine and then reduced with stannous chloride to give 4-amino-N[2-(morpholin-4-yl)ethyl]benzenesulfonamide, used to synthesize compound 128A.

Preparative Example 14

Preparation of (R)—N-(3,4-diaminophenyl)-1-methylpiperidine-2-carboxamide, an intermediate to compound 143A by Reaction Scheme 2

O-(Benzotriazol-1-yl)-N,N,N',N'-tetramethyluronium hexafluorophosphate (HBTU, 4.96 g, 13.1 mmol) was added to a stirred solution of (R)—N-Boc-2-piperidinecarboxylic acid (3.00 g, 13.1 mmol) and DIPEA (9.0 mL, 51.2 mmol) in anhydrous DMF (50 mL). The mixture was stirred at room temperature for 5 min and then 2-nitro-1,4-phenylenediamine (3.00 g, 13.1 mmol) was added. The mixture was stirred for a further 18 hr, then the DMF was removed by evaporation. The residue was partitioned between water (200 mL) and EA (100 mL) and the phases separated. The aqueous phase was extracted with two further portions of EA (100 mL each) and the combined organic extracts washed with water, 1M sodium carbonate solution, water, and brine (100 mL each). The solution was dried over magnesium sulfate and concentrated to give (R)-tert-butyl 2-[(4-amino-3-nitrophenyl)aminocarbonyl]-piperidine-1-carboxylate as a brown solid (4.80 g).

(R)-tert-Butyl 2-[(4-amino-3-nitrophenyl)aminocarbonyl]piperidine-1-carboxylate (4.80 g, 13.2 mmol) was suspended in dioxane (100 mL) and hydrogen chloride (75 mL of a 4M solution in dioxane) was added. The resulting dark colored solution was stirred at room temperature for 3.5 hr resulting in a yellow/brown suspension. The solid was collected by filtration and briefly dried under high vacuum. The solid was suspended in water, the pH was adjusted to pH 8 with 1M sodium carbonate solution and the resulting suspension stirred for 15 minutes. The solid was collected and dried under high vacuum to give (R)—N-(4-amino-3-nitrophenyl)piperidine-2-carboxamide hydrochloride salt as an orange solid (2.08 g). This was treated with 1M sodium carbonate solution (200 mL) and extracted with EA (3×). The combined EA extracts were washed with brine, dried over magnesium sulfate, and concentrated to give (R)—N-(4-amino-3-nitrophenyl)piperidine-2-carboxamide as an orange foam (1.77 g).

(R)—N-(4-Amino-3-nitrophenyl)piperidine-2-carboxamide (2.09 g, 7.9 mmol) was dissolved in MeOH (50 mL), and paraformaldehyde (0.95 g) and sodium cyanoborohydride (0.50 g, 8.0 mmol) were added. The mixture was stirred at room temperature for 70 min, and water added dropwise. The solvent was evaporated and the residue partitioned between water and EA (150 mL each). The phases were separated and the aqueous phase extracted with EA (2×100 mL). The combined EA layers were washed with brine, dried over magnesium sulfate, and concentrated to give (R)—N-(4-amino-3-nitrophenyl)-1-methylpiperidine-2-carboxamide as an orange foam (2.17 g), which was used without purification.

A solution of (R)—N-(4-amino-3-nitrophenyl)-1-methylpiperidine-2-carboxamide (2.17 g, 7.8 mmol) in ethanol (75 mL) was degassed under vacuum and then backfilled with argon. 10% Palladium on carbon (0.44 g) was added and the mixture again degassed under vacuum. Hydrogen was introduced by a balloon and the reaction stirred at room temperature for 23 hr. The mixture was degassed by bubbling argon through it, and was then filtered through a pad of diatomaceous earth. The filtrate was concentrated to give (R)—N-(3,4-diaminophenyl)-1-methylpiperidine-2-carboxamide as a purple solid (1.78 g).

(S)—N-(3,4-diaminophenyl)-1-methylpiperidine-2-carboxamide, an intermediate to compound 142A, was prepared by the same method, starting with (S)—N-Boc-2-piperidinecarboxylic acid.

Preparative Example 15

Preparation of (S)—N-(3,4-diaminophenyl)-N-ethyl-1-methylpyrrolidine-2-carboxamide, an intermediate to compound 145A by Reaction Scheme 2

A solution of 2-nitro-1,4-phenylenediamine (10.0 g, 65.3 mmol), di-tert-butyl dicarbonate (15.7 g, 71.8 mmol) and DIPEA (13.5 mL, 71.8 mmol) in dioxane (150 mL) was heated at gentle reflux for 1 hr and then allowed to cool to room temperature. The solvent was evaporated and the residue partitioned between DCM (500 mL) and water (200 mL) and the phases separated. The aqueous phase was extracted with DCM (2×200 mL) and the combined DCM layers washed with brine, dried over magnesium sulfate, and concentrated to give tert-butyl 4-amino-3-nitrophenylcarbamate as a brown solid (16.6 g).

Sodium hydride (5.24 g of a 60% dispersion in mineral oil, 131 mmol) was added in portions over 25 min to a stirred solution of tert-butyl 4-amino-3-nitrophenylcarbamate (16.6 g, 65.6 mmol) in anhydrous THF (200 mL). The mixture was stirred for a further 10 min and iodoethane (5.2 mL, 65.0 mmol) was added. The mixture was stirred at room temperature for 22 hr and was then quenched by the addition of a little water. The solvent was evaporated and the residue partitioned between EA and brine (300 mL each). The phases were separated and the aqueous phase extracted with EA (2×150 mL). The combined EA layers were washed with brine, dried over magnesium sulfate, and concentrated to give a brown gum (16.0 g), which was purified by column chromatography eluting with 30% EA, 70% hexanes to give tert-butyl 4-amino-3-nitrophenyl(ethyl)carbamate as a brown foam (3.59 g).

The tert-butyl 4-amino-3-nitrophenyl(ethyl)carbamate from the previous step was dissolved in dioxane (35 mL) and hydrogen chloride (35 mL of a 4M solution in dioxane) was added. The mixture was stirred at room temperature for 18 hr and then the solvent was evaporated. The residue was dissolved in water (200 mL) and the solution adjusted to pH10 with 5M sodium hydroxide solution. The solution was extracted with EA (3×100 mL), and the combined EA extracts were washed with brine, dried over magnesium sulfate, and concentrated to give $N^1$-ethyl-3-nitrobenzene-1,4-diamine as a purple solid (1.68 g).

Triethylamine (1.0 mL, 7.33 mmol) was added to a stirred solution of $N^1$-ethyl-3-nitrobenzene-1,4-diamine (440 mg, 2.43 mmol), N-methyl-L-proline (314 mg, 2.43 mmol) and DEPBT (727 mg, 2.43 mmol) in acetonitrile (15 mL). The mixture was stirred at room temperature and further aliquots of N-methyl-L-proline (314 mg, 2.43 mmol), DEPBT (727 mg, 2.43 mmol), and triethylamine (1.0 mL, 7.33 mmol) were added after 1, 2, and 3 days. After stirring for a further 1 day, the mixture was concentrated and the residue taken up in EA (75 mL). The EA solution was extracted with water, and with 1M sodium carbonate solution (2×). The combined water and 1M sodium carbonate solution extracts were back-extracted with EA (4×) and the combined EA extracts washed with brine, dried over magnesium sulfate, and concentrated to give (S)—N-(4-amino-3-nitrophenyl)-N-ethyl-1-methyl-pyrrolidine-2-carboxamide (388 mg) as an orange/brown oil. This was hydrogenated in ethanol, using 10% palladium on carbon (153 mg) as the catalyst. After stirring overnight under a hydrogen atmosphere (balloon), the mixture was filtered through a pad of diatomaceous earth and the filtrate concentrated to give (S)—N-(3,4-diaminophenyl)-N-ethyl-1-methylpyrrolidine-2-carboxamide (335 mg).

Synthesis Example 1

Synthesis of 2-[1H-benzimidazol-2(3H)-ylidene]-2-(4-trifluoromethyl-pyrimidin-2-yl)acetamide, compound 1A, by Reaction Scheme 1

A solution of 2-[1H-benzimidazol-2(3H)-yl]acetonitrile (10 g, 64 mmol), di-tert-butyl dicarbonate (16.6 g, 76 mmol), and triethylamine (8.8 mL, 64 mmol) in THF (180 mL) was stirred at room temperature overnight. The solvent was removed under vacuum, and the crude product was dissolved in chloroform and washed with water, 1N hydrochloric acid, and saturated aqueous sodium bicarbonate. The chloroform phase was dried over magnesium sulfate, and the solvent was removed under vacuum to give 2-[1-(tert-butoxycarbonyl)benzimidazol-2(3H)-yl]acetonitrile (15 g) as a solid.

A solution of 2-[1-(tert-butoxycarbonyl)benzimidazol-2 (3H)-yl]acetonitrile (6 g, 23 mmol) in THF (50 mL) was added to a suspension of 60% sodium hydride in mineral oil (1.38 g, 35 mmol) in tetrahydrofuran (85 mL) at 0° C. over 10 min. The suspension was stirred at 0° C. for 15 min, and 2-chloro-4-trifluoromethylpyrimidin (2.79 mL, 23 mmol) was added. The mixture was allowed to warm to room temperature and stirred overnight, and water (300 mL) and then 1N hydrochloric acid (40 mL) were added. The crude product was extracted into chloroform and washed twice with water (100 mL each). The organic phase was dried over magnesium sulfate, and the solvent was removed under vacuum to give 2-[1-(tert-butoxycarbonyl)benzimidazol-2(3H)-ylidene]-2-(4-trifluoromethylpyrimidin-2-yl)acetonitrile (8.17 g) as a brown oil.

2-[1-(tert-Butoxycarbonyl)benzimidazol-2(3H)-ylidene]-2-(4-trifluoromethylpyrimidin-2-yl)-acetonitrile (8.1 g, 20 mmol) was dissolved in concentrated sulfuric acid (30 mL), and the solution added gradually to ice/water (100 mL), allowed to warm to room temperature, and stirred overnight. The mixture was cooled to 0° C., poured over ice, and neutralized with 50% aqueous sodium hydroxide. Water was added, and the crude product was extracted with 4:1 chloroform/isopropanol. The organic phase was dried over magnesium sulfate, the solvent was removed under vacuum, and the solid was purified by reverse phase preparative HPLC to give 2-[1H-benzimidazol-2(3H)-ylidene]-2-(4-trifluoromethylpyrimidin-2-yl)acetamide (1.18 g, 18% overall yield) as a yellow solid.

Compounds 4A, 132A, 135A, and 138A, for example, were prepared by this general method, using the appropriately substituted starting materials.

Synthesis Example 2

Synthesis of 2-[benzothiazol-2(3H)-ylidene]-2-(pyrimidin-2-yl)acetamide, compound 2A, by Reaction Scheme 1

2-(Benzothiazol-2-yl)acetonitrile (0.69 g, 4 mmol) was added in portions to a suspension of 95% sodium hydride ((0.21 g, 6 mmol) in THF (12 mL). The resulting yellow suspension was stirred at room temperature for 30 min, and 2-chloropyrimidine (0.45 g, 4 mmol) was added. The mixture was stirred for 3 d, and water was added to the dark solution. The mixture was acidified with 1N hydrochloric acid, and the precipitate that formed was collected by filtration, washed with water and acetonitrile, and dried under vacuum to give 2-[benzothiazol-2(3H)-ylidene]-2-(pyrimidin-2-yl)acetonitrile as a brown solid.

2-[Benzothiazol-2(3H)-ylidene]-2-(pyrimidin-2-yl)acetonitrile (0.1 g, 0.39 mmol) was dissolved in concentrated sulfuric acid (2 mL) and stirred at room temperature for 5 hr. The mixture was cooled to 0° C., poured over ice, and neutralized with 50% aqueous sodium hydroxide. The precipitate that formed was collected by filtration and purified by reverse phase preparative HPLC to give 2-[benzothiazol-2(3H)-ylidene]-2-(pyrimidin-2-yl)acetamide (42 mg, 40% yield) as a yellow solid.

Compounds 3A, 16A, 18A, 21A, 22A, and 23A, for example, were prepared by this general method, using the appropriately substituted starting materials. Compound 5A was prepared from the nitrile intermediate to compound 3A by hydrolysis of a methanolic solution of the intermediate with 1M aqueous lithium hydroxide for 2 d at room temperature, neutralization with 1N hydrochloric acid, collection of the precipitate by filtration, washing with water and acetonitrile, and drying to give 2-[benzothiazol-2(3H)-ylidene]-2-(5-carboxy-4-trifluoromethylpyrimidin-2-yl)acetonitrile. This was hydrolyzed with concentrated sulfuric acid and purified to give 2-[benzothiazol-2(3H)-ylidene]-2-(5-carboxy-4-trifluoromethylpyrimidin-2-yl)acetamide, compound 5A. Compound 24A was similarly prepared from the nitrile intermediate to compound 23A.

Synthesis Example 3

Synthesis of 2-[benzothiazol-2(3H)-ylidene]-2-[5-(4-methylpiperazine-1-carbonyl)-4-trifluoromethylpyrimidin-2-yl]acetamide, compound 130A, by Reaction Scheme 1

2-(Benzothiazol-2-yl)acetonitrile (2.05 g, 12 mmol) was added in portions to stirred concentrated sulfuric acid (5 mL) over 10 min. The mixture was stirred for 4 hr, then poured over ice/water. The precipitate that formed was extracted into EA and washed with brine, then the organic phase was dried over magnesium sulfate and the solvent removed under vacuum to give 2-(benzothiazol-2-yl)acetamide (1.02 g) as an orange solid.

Sodium hydride 99% (50.8 mg, 2.1 mmol) was added to a suspension of 2-(benzothiazol-2-yl)acetamide (103 mg, 0.53 mmol) in THF (2 mL), and the resulting yellow suspension was stirred at room temperature for 15 min. The mixture was cooled to 0° C. and (2-chloro-4-trifluoromethyl-pyrimidin-5-yl)(4-methylpiperazin-1-yl)methanone (0.18 g, 0.53 mmol) was added. The mixture was stirred at room temperature overnight and the solvent was then removed under reduced pressure. The residue was suspended in water and the pH adjusted to 7 with 1N hydrochloric acid. The solid was collected by filtration and partitioned between EA and water. The EA phase was separated, washed with brine, dried over magnesium sulfate, and concentrated under vacuum. The resulting material was purified by reverse phase preparative HPLC to give 2-[benzothiazol-2(3H)-ylidene]-2-[5-(4-methylpiperazine-1-carbonyl)-4-trifluoromethylpyrimidin-2-yl]acetamide hydrochloride (87 mg, 33% yield) as a yellow solid.

Compounds 2A, 131A, and 134A, for example, were prepared by this general method using the appropriately substituted starting materials.

Synthesis Example 4

Synthesis of 2-(5-{[3-(4-morpholinyl)propyl]aminocarbonyl}-1H-benzimidazol-2(3H)-ylidene)-2-(4-trifluoromethylpyrimidin-2-yl)acetamide, compound 39A, by Reaction Scheme 2

A mixture of 3,3-bis(methylthio)-2-(4-trifluoromethylpyrimidin-2-yl)acrylonitrile (682 mg, 2.34 mmol), 3,4-diaminobenzoic acid (392 mg, 2.57 mmol, 1.1 eq.), and 4-dimethylaminopyridine (143 mg, 1.17 mmol, 0.5 eq.) in ethanol (3 mL) was heated at 150° C. for 0.5 hr in a microwave. The mixture was cooled to room temperature, concentrated hydrochloric acid (1 mL) was added, and the mixture was allowed to stand for 0.5 hr. The precipitate that formed was collected by filtration, washed with ethanol and acetonitrile, and dried under vacuum to give 2-[5-carboxy-1H-benzimidazol-2(3H)-ylidene]-2-(3-trifluoromethylpyrimidin-2-yl)acetonitrile (450 mg, 1.29 mmol, 55% yield) as a brown solid.

The 2-[5-carboxy-1H-benzimidazol-2(3H)-ylidene]-2-(4-trifluoromethylpyrimidin-2-yl)-acetonitrile (450 mg, 1.29 mmol) from the previous step, dissolved in concentrated sulfuric acid (2 mL), was heated to 50° C. for 6 hr. The mixture was cooled to room temperature and added dropwise to rapidly stirred room-temperature water (500 mL). The precipitate that formed was collected by filtration, washed with water, and dried under vacuum to give 2-[5-carboxy-1H-benzimidazol-2(3H)-ylidene]-2-(4-trifluoromethylpyrimidin-2-yl)acetamide (322 mg, 0.88 mmol, 68% yield) as a dark brown solid.

To a room temperature solution of 2-[5-carboxy-1H-benzimidazol-2(3H)-ylidene]-2-(4-trifluoromethylpyrimidin-2-yl)acetamide (630 mg, 1.73 mmol) in dimethylformamide (20 mL) was added DIPEA (661 µL, 3.79 mmol, 2.2 eq.), HBTU (720 mg, 1.90 mmol, 1.1 eq.). After 5 min, 3-(4-morpholinyl)propan-1-amine (277 µL, 1.90 mmol, 1.1 eq.) was added and the mixture was stirred at room temperature for 3 hr. The mixture was diluted with EA (50 mL) and washed three times with 5% aqueous sodium bicarbonate (50 mL each). The EA fraction was decanted, dried over magnesium sulfate, filtered, and concentrated under vacuum to give a yellow solid. About 2 mL of 4.0 M hydrogen chloride in dioxane was added, and the mixture was stirred for 15 min and then concentrated under vacuum to give 2-(5-{[3-(4-morpholinyl)propyl]aminocarbonyl}-1H-benzimidazol-2(3H)-ylidene)-2-(4-trifluoromethylpyrimidin-2-yl)acetamide hydrochloride (750 mg, 1.52 mmol, 88% yield) as a yellow solid.

Compounds 33A, 34A, 41A, 44A, 45A, 48A, 51A, 53A, 73A, 77A, 79A to 83A, 86A, and 142A to 146A, for example, were prepared by this general method using the appropriately substituted starting materials.

Synthesis Example 5

Synthesis of 2-(6-{[3-(4-morpholinyl)propyl]aminocarbonyl}-benzothiazol-2(3H)-ylidene)-2-(4-trifluoromethylpyrimidin-2-yl)acetamide, compound 40A, by Reaction Scheme 2

A mixture of 4-amino-3-mercaptobenzoic acid (768 mg, 4.5 mmol), 3,3-bis(methylthio)-2-(4-trifluoromethylpyrimidin-2-yl)acrylonitrile (1.45 g, 5.0 mmol, 1.1 eq.), 4-dimethylaminopyridine (550 mg, 4.5 mmol, 1 eq.), and potassium carbonate (622 mg, 4.5 mmol, 1 eq.) in ethanol (20 mL) was heated at 160° C. for 0.4 hr in a microwave. The mixture was cooled to room temperature, diluted with DCM, and washed with 1M hydrochloric acid. The DCM fraction was decanted, filtered, and concentrated under vacuum to give 2-[6-carboxybenzothiazol-2(3H)-ylidene]-2-(4-trifluoromethyl-pyrimidin-2-yl)acetonitrile (729 mg, 40% yield) as a brown solid.

A solution of 2-[6-carboxybenzothiazol-2(3H)-ylidene]-2-(4-trifluoromethylpyrimidin-2-yl)-acetonitrile (620 mg, 1.70 mmol) in concentrated sulfuric acid (5 mL), was heated to 50° C. for 10 hr. The mixture was cooled to room temperature and added dropwise to rapidly stirred room-temperature water (100 mL). The precipitate that formed was collected by filtration, washed with water and hexanes, and dried under vacuum to give 2-[6-carboxybenzothiazol-2(3H)-ylidene]-2-(4-trifluoromethylpyrimidin-2-yl)acetamide (587 mg, 90% yield) as a brown solid.

To a room temperature solution of 2-[6-carboxybenzothiazol-2(3H)-ylidene]-2-(4-trifluoromethylpyrimidin-2-yl)acetamide (350 mg, 0.92 mmol) in acetonitrile (5 mL) was added triethylamine (250 µL, 1.79 mmol, 2 eq.), DEPBT (299 mg, 1.0 mmol, 1.1 eq.), and 3-(4-morpholinyl)-propan-1-amine (134 µL, 0.92 mmol, 1.0 eq.), and the mixture was stirred at room temperature until a yellow-brown precipitate formed. The precipitate was collected by filtration, washed with acetonitrile, and dried under vacuum to give a yellow solid. About 2 mL of 4.0 M hydrogen chloride in dioxane was added, and the mixture was stirred for 15 min and then concentrated under reduced pressure to give 2-(6-{[3-(morpholin-4-yl)propyl]aminocarbonyl}-benzothiazol-2(3H)-ylidene)-2-(4-trifluoromethyl-pyrimidin-2-yl)acetamide hydrochloride (340 mg, 73% yield) as a yellow solid.

Synthesis Example 6

Synthesis of 2-[6-nitrobenzothiazol-2(3H)-ylidene]-2-(4-trifluoromethyl-pyrimidin-2-yl)acetamide, compound 26A, by Reaction Scheme 3

To a solution of 2-(methylthio)-6-nitro-1,3-benzothiazole (226 mg, 1.0 mmol) in ethanol (3.5 mL) was added 2-(4-trifluoromethylpyrimidin-2-yl)acetonitrile (187 mg, 1.0 mmol) and potassium carbonate (207 mg, 1.5 mmol). The orange mixture was heated in the microwave at 160° C. for 15 min, then cooled and poured into EA (60 mL). The organic layer was washed twice with 1N hydrochloric acid (25 mL each), brine (25 mL), and water (5 mL), then dried with magnesium sulfate, filtered, and concentrated under reduced pressure to give 2-(6-nitrobenzothiazol-2(3H)-ylidene)-2-(4-trifluoromethylpyrimidin-2-yl)acetonitrile (349 mg, 96% yield) as a yellow solid.

2-(6-Nitrobenzothiazol-2(3H)-ylidene)-2-(4-trifluoromethylpyrimidin-2-yl)acetonitrile (296 mg, 0.81 mmol) was dissolved in concentrated sulfuric acid (3.0 mL). The reddish mixture was stirred at 50° C. for 8 hr, then poured into cold water (25 mL). The yellow precipitate was collected by filtration, washed with hexanes (30 mL), and dried under vacuum to give 2-[6-nitrobenzothiazol-2(3H)-ylidene]-2-(4-trifluoromethylpyrimidin-2-yl)acetamide (280 mg, 89% yield) as an orange solid.

Compound 32A was prepared from compound 26A as follows. To a solution of 2-[6-nitrobenzothiazol-2(3H)-ylidene]-2-(4-trifluoromethylpyrimidin-2-yl)acetamide (280 mg, 0.73 mmol) in MeOH (25 mL) was added a slurry of 10% palladium on carbon (200 mg) in MeOH (10 mL), and the mixture was stirred under hydrogen at atmospheric pressure for 24 hr. The mixture was filtered and the filtrate concentrated to give crude 2-[6-aminobenzothiazol-2(3H)-ylidene]-2-(4-trifluoromethylpyrimidin-2-yl)acetamide as a red powder. This was purified by flash column chromatography eluting with 19:1 EA/MeOH to give pure 2-[6-aminobenzothiazol-2(3H)-ylidene]-2-(4-trifluoromethylpyrimidin-2-yl)acetamide, compound 32A (160 mg, 62% yield) as a yellow powder.

Compound 76A was prepared from compound 32A as follows. To a solution of N-(tert-butoxycarbonyl)glycine hydrochloride (20 mg) in DMF (5 mL) were added O-(7-azabenzotriazol-1-yl)-N,N,N',N'-tetramethyluronium hexafluorophosphate (190 mg), triethylamine (388 µL, 3.88 mmol), and 2-[6-aminobenzothiazol-2(3H)-ylidene]-2-(4-trifluoromethylpyrimidin-2-yl)acetamide (141 mg). The mixture was stirred at room temperature for 1 hr, then poured into EA (50 mL). The EA layer was washed three times with 10% aqueous sodium bicarbonate (30 mL each), and three times with water (15 mL each), then dried over magnesium sulfate, filtered, and concentrated under reduced pressure to give 2-{6-[(tert-butyloxycarbonylamino)acetylamino]benzothiazol-2(3H)-ylidene}-2-(4-trifluoromethylpyrimidin-2-yl)acetamide as a brown foam. 2-{6-[(Tert-butyloxycarbonylamino)-acetylamino]benzothiazol-2(3H)-ylidene}-2-(4-trifluoromethylpyrimidin-2-yl)acetamide (80 mg, 156 mmol) was dissolved in 4N hydrogen chloride in dioxane (5.0 mL, 20 mmol), and the mixture stirred at room temperature for 2 hr. The mixture was concentrated to give 2-{6-[(2-aminoacetyl)-amino]benzothiazol-2(3H)-ylidene}-2-(4-trifluoromethylpyrimidin-2-yl)acetamide (50 mg) as a beige solid. Other compounds with an amide side-chain may be similarly prepared from compound 32A.

Synthesis Example 7

Synthesis of 2-{6-[2-(1H-imidazol-1-yl)ethoxy]benzothiazol-2(3H)-ylidene}-2-(4-trifluoromethylpyrimidin-2-yl)acetamide, compound 117A, by Reaction Scheme 4

To an ice-cooled stirred biphasic solution of 4-[2-(1H-imidazol-1-yl)ethoxy]benzenamine (1.00 g; 4.92 mmol) and sodium bicarbonate (2.07 g; 24.6 mmol) in chloroform (100 mL) and water (50 mL) was added a solution of thiophosgene (452 µL; 5.90 mmol) in chloroform (10 mL) over 5 min. The mixture was stirred at ice-bath temperature for 20 min, and then the aqueous and organic phases were separated and the aqueous phase extracted with chloroform (50 mL). The combined chloroform layers were washed with brine, then dried over magnesium sulfate and concentrated under reduced pressure to give 1-[2-(4-isothiocyanatophenoxy)ethyl]-1H-imidazole (1.41 g) as a yellow oil.

Sodium hydride (0.531 g of a 60 wt % dispersion in oil, 13.3 mmol) was added in portions to a stirred solution of 2-(4-trifluoromethylpyrimidin-2-yl)acetamide (0.911 g; 4.43 mmol) in THF (20 mL) over 10 min. A solution of 1-[2-(4-isothiocyanatophenoxy)ethyl]-1H-imidazole (1.21 g; 4.92 mmol) in THF (10 mL) was then added over 15 min. The mixture was stirred at room temperature for a further 1 hr, and then water (1 mL) was added and the mixture was concentrated under reduced pressure. Water (75 mL) was added to the residue, the pH adjusted to 7 with 2N hydrochloric acid, and the mixture was extracted three times with EA. The combined EA extracts were washed with brine, dried over magnesium sulfate, and concentrated under reduced pressure to give 3-{4-[2-(1H-imidazol-1-yl)ethoxy]phenylamino}-3-thioxo-2-(4-trifluoromethylpyrimidin-2-yl)propanamide (1.47 g) as an orange semi-solid.

A solution of 3-{4-[2-(1H-imidazol-1-yl)ethoxy]phenylamino}-3-thioxo-2-(4-trifluoromethyl-pyrimidin-2-yl)propanamide (1.47 g, 3.29 mmol) in glacial acetic acid (10 mL) was cooled in a cold water bath and a solution of bromine (126 µL, 2.46 mmol) in glacial acetic acid (1 mL) added dropwise over 10 min. The mixture was allowed to warm to room temperature with stirring for a further 35 min, and the acetic acid was decanted. The residue was dried under vacuum, then dissolved in acetonitrile/water and purified by reverse phase preparative HPLC to give produce 2-{6-[2-(1H-imidazol-1-yl)ethoxy]-benzothiazol-2(3H)-ylidene}-2-(4-trifluoromethylpyrimidin-2-yl)acetamide hydrochloride (0.406 g) as an orange solid.

Compounds 50A, 52A, 89A, 91A, 93A to 95A, 97A to 101A, 103A, 104A, 106A, 108A, 110A to 116A, 118A, and 120A to 129A, for example, were prepared by this general method using the appropriately substituted starting materials.

Synthesis Example 8

Synthesis of 2-[benzothiazol-2(3H)-ylidene-2-[4-tert-butyl-6-(trifluoromethyl)pyrimidin-2-yl]acetamide, compound 7A, by Reaction Scheme 5

To a stirred solution of 2-chlorobenzothiazole (1.0 mL, 8.1 mmol) and malononitrile (534 mg; 8.1 mmol) in acetonitrile (4 mL) was added sodium ethoxide (3.0 mL of 21 wt % solution in ethanol, 8.0 mmol). The mixture was stirred at room temperature for 4 d, then acidified with 2M hydrochloric acid. The solid was collected by filtration, washed with acetonitrile, and dried under vacuum to give 2-(benzothiazol-2(3H)-ylidene)malononitrile (770 mg) as a white solid.

A suspension of 2-(benzothiazol-2(3H)-ylidene)malononitrile (0.45 g, 2.25 mmol) in dioxane (10 mL) and ethanol (10 mL) was cooled to 0° C. and hydrogen chloride gas was bubbled into the mixture for 10 min. The mixture was allowed to warm to room temperature, then heated to 50° C. overnight. The resulting precipitate was collected by filtration, washed with acetonitrile, and dried under vacuum to give 2-[benzothiazol-2(3H)-ylidene]-2-cyanoacetimidate (0.43 g) as a white solid.

A suspension of 2-[benzothiazol-2(3H)-ylidene]-2-cyanoacetimidate (0.4 g, 1.6 mmol) in ethanol (5 mL) was placed in a pressure tube, cooled to −78° C., and gaseous ammonia was bubbled into the tube. The mixture was allowed to warm to room temperature and stirred for 3 d. The solvent was removed under vacuum to give 2-[benzothiazol-2(3H)-ylidene]-2-cyanoacetamidine as a beige solid.

2-[Benzothiazol-2(3H)-ylidene]-2-cyanoacetamidine (0.2 g, 0.92 mmol) was dissolved in dimethylsulfoxide (1 mL), and 1,1,1-trifluoro-5,5,-dimethyl-2,4-hexanedione (320 µL, 1.84 mmol) and sodium ethoxide (0.6 mL of 21 wt % solution in ethanol, 1.84 mmol) were added. The solution was heated to 180° C. under microwave irradiation for 20 min, dissolved in EA, and washed with 1N hydrochloric acid and then water. Removal of the solvent gave 2-[benzothiazol-2(3H)-ylidene]-2-[4-tert-butyl-6-(trifluoromethyl)pyrimidin-2-yl]acetonitrile as a beige solid.

2-[Benzothiazol-2(3H)-ylidene]-2-[4-tert-butyl-6-(trifluoromethyl)pyrimidin-2-yl]acetonitrile (150 mg, 0.39 mmol) was dissolved in concentrated sulfuric acid (1.5 mL) and stirred at room temperature overnight. The mixture was cooled to 0° C., poured over ice, and neutralized with 50% aqueous sodium hydroxide. The product was partially extracted into chloroform, and dried to a brown solid (57 mg), which was purified by reverse phase preparative HPLC to give 2-[benzothiazol-2(3H)-ylidene]-2-[4-tert-butyl-6-(trifluoromethyl)pyrimidin-2-yl]acetamide (13 mg) as a yellow solid.

Synthesis Example 9

Synthesis of 2-{5-[(S)-(1-methylpyrrolidin-2-yl)carbonylamino]-1H-benzimidazol-2(3H)-ylidene}-2-[4-methyl-6-(trifluoromethyl)pyrimidin-2-yl]acetamide, compound 144A A solution of 1,1,1-trifluoro-2,4-pentanedione (5.00 g; 32.4 mmol) and S-methylisothiourea hemisulfate (4.06 g; 29.2 mmol) in pyridine (3.75 mL) and water (62 mL) was heated at reflux for 1 day. The mixture was cooled to room temperature, extracted with chloroform, and the chloroform extract washed with water to give 4-methyl-2-(methylthio)-6-(trifluoromethyl)pyrimidine as an off-white solid (4.60 g, 22.1 mmol). This was dissolved in MeOH (60 mL), and a solution of OXONE® (27.1 g, 44.2 mmol) in water (100 mL) was added over 10 min. The mixture was stirred at room temperature for 4 hr and then extracted with EA. The EA was washed with water, dried, and concentrated to give 4-methyl-2-(methylsulfonyl)-6-(trifluoromethyl)pyrimidine (4.8 g) as a white solid. Sodium hydride (0.16 g of a 60% dispersion in mineral oil; 4.0 mmol) was added to a stirred solution of ethyl cyanoacetate (0.21 mL; 2.0 mmol) in THF (8 mL), and the resulting suspension stirred at room temperature for 15 min. 4-Methyl-2-(methylsulfonyl)-6-(trifluoromethyl)pyrimidine (0.48 g; 2.0 mmol) was then added, and the mixture stirred overnight. Water was added, followed by 1M hydrochloric acid to adjust to pH 3-4. The solid that formed solid was filtered, washed with water, and dried under high vacuum to give ethyl 2-cyano-2-[4-methyl-6-(trifluoromethyl)pyrimidin-2-yl]acetate hydrochloride salt (0.43 g) as a pale yellow solid.

4-Nitro-1,2-phenylenediamine (50 mg; 0.32 mmol) and ethyl 2-cyano-2-[4-methyl-6-(trifluoromethyl)pyrimidin-2-yl]acetate hydrochloride salt (101 mg; 0.32 mmol) were heated at 198° C. in a microwave for 3 min. Acetic acid (1.5 mL) was added to the crude material and the mixture heated at 100° C. for 6 hr. The solid was collected by filtration, washed with acetonitrile, and dried under high vacuum to give 2-[4-methyl-6-(trifluoromethyl)pyrimidin-2-yl]-2-(5-nitro-1H-benzimidazol-2(3H)-ylidene)acetonitrile (59 mg) as a yellow solid. 2-[4-Methyl-6-(trifluoromethyl)pyrimidin-2-yl]-2-(5-nitro-1H-benzimidazol-2(3H)-ylidene)acetonitrile (55 mg; 0.15 mmol) in DMF (3 mL) was hydrogenated over 10% palladium on carbon (11 mg). The mixture was filtered through diatomaceous earth, washing with methanol, and the filtrate was concentrated to give 2-(5-amino-1H-benzimidazol-2(3H)-ylidene)-2-[4-methyl-6-(trifluoromethyl)pyrimidin-2-yl]acetonitrile, which was dissolved in DMF (1 mL) and added to a solution of N-methyl-L-proline (19.3 mg; 0.16 mmol), HBTU (56.8 mg; 0.15 mmol), and DIPEA (104.5 µL; 0.60 mmol) in DMF (1 mL). The mixture was stirred for 5 hr and then partitioned between EA and water. The EA phase was dried and concentrated to give 2-{5-[(S)-(1-methylpyrrolidin-2-yl)carbonylamino]-1H-benzimidazol-2 (3H)-ylidene}-2-[4-methyl-6-(trifluoromethyl)pyrimidin-2-yl]acetonitrile (65 mg) as a brown oil. 2-{5-[(S)-(1-Methylpyrrolidin-2-yl)-carbonylamino]-1H-benzimidazol-2 (3H)-ylidene}-2-[4-methyl-6-(trifluoromethyl)pyrimidin-2-yl]-acetonitrile (65 mg) was dissolved in concentrated sulfuric acid and stirred at room temperature overnight. The mixture was diluted with ice-water and acetonitrile and, after coming to room temperature, was purified by reverse phase preparative HPLC using a Peeke Ultro 120, 7 µm, C18Q, 250×30 mm column at a flow rate of 42 mL/min and mobile phases of 95% water, 5% acetonitrile (with 0.01% hydrochloric acid) and 5% water, 95% acetonitrile (with 0.01% hydrochloric acid) to give 2-{5-[(S)-(1-methylpyrrolidin-2-yl)carbonylamino]-1H-benzimidazol-2 (3H)-ylidene}-2-[4-methyl-6-(trifluoromethyl)pyrimidin-2-yl]acetamide hydrochloride salt (18 mg) as a yellow solid.

The compounds of formula A as shown in the table below were prepared by one or more of the above methods, or similar methods not described in detail here. All of the compounds of formula A were analyzed to confirm identity and purity, using HPLC for purity, and one or more of mass spectrometry (using either positive or negative ionization) and NMR ($^1$H and/or $^{13}$C) for identity, and were confirmed to be the expected product in good purity. Other compounds of formula A may be similarly prepared.

Representative compounds of formula A include ("exact mass" is of the parent compound; mass spectra were with positive ionization and mass M+H, unless the mass was noted otherwise):

| Compound | Structure | Exact mass, M | MS (m/z) |
|---|---|---|---|
| 1A | 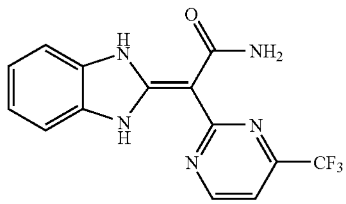 | 321 | 322 |
| 2A | 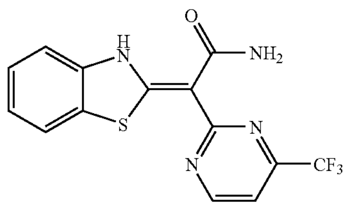 | 338 | 339 |
| 3A | 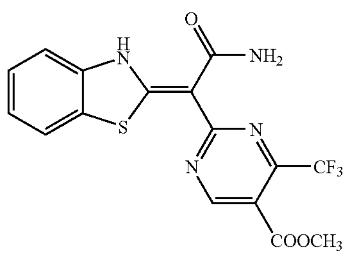 | 396 | 397 |
| 4A | 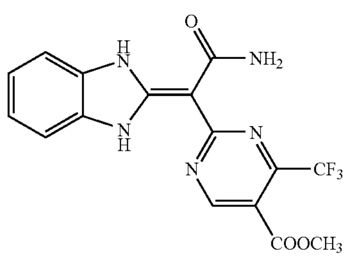 | 379 | 380 |
| 5A | 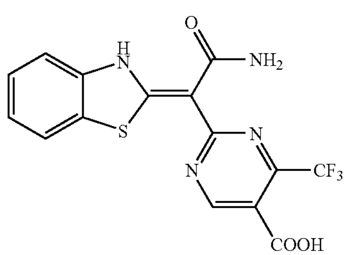 | 382 | 383 |
| 6A | 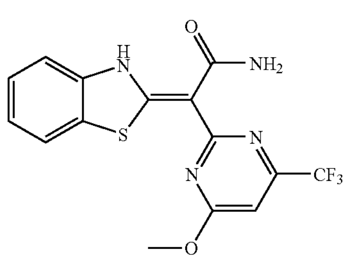 | 368 | 369 |

-continued

| Compound | Structure | Exact mass, M | MS (m/z) |
|---|---|---|---|
| 7A | 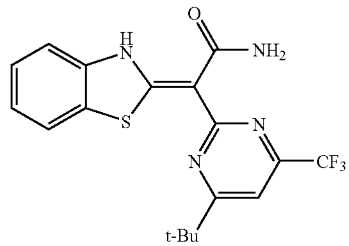 | 394 | 395 |
| 8A | 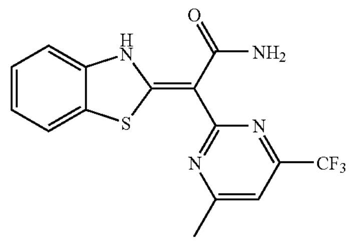 | 352 | 353 |
| 9A | 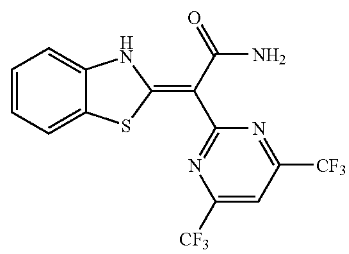 | 406 | 407 |
| 10A | 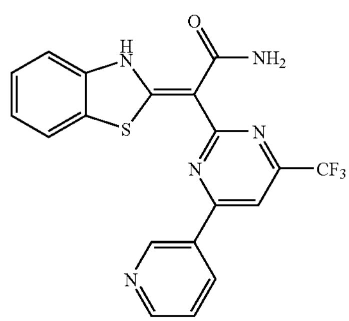 | 415 | 414 (M − H) |
| 11A | 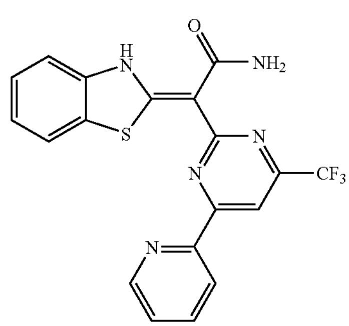 | 415 | 414 (M − H) |

-continued

| Compound | Structure | Exact mass, M | MS (m/z) |
|---|---|---|---|
| 12A | 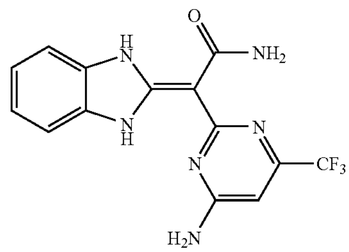 | 336 | 337 |
| 13A | 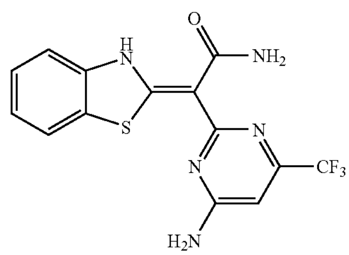 | 353 | 354 |
| 14A | 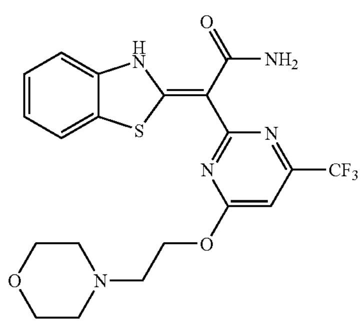 | 467 | 468 |
| 15A | 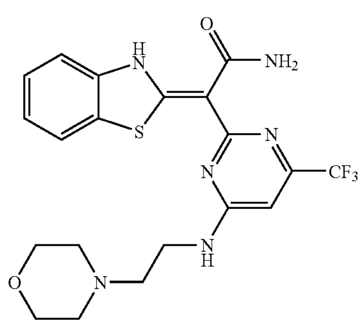 | 466 | 467 |
| 16A | 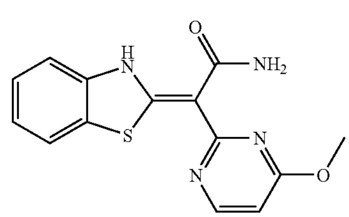 | 300 | 301 |
| 17A | 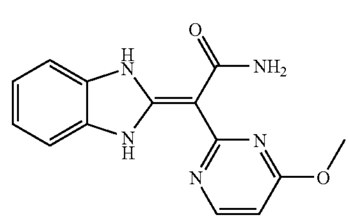 | 283 | 284 |

-continued

| Compound | Structure | Exact mass, M | MS (m/z) |
|---|---|---|---|
| 18A | 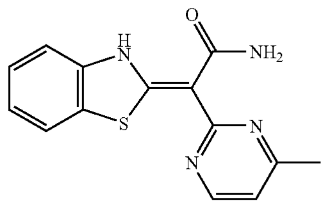 | 284 | 285 |
| 19A | 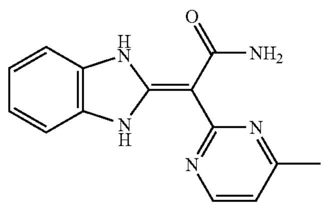 | 267 | 268 |
| 20A | 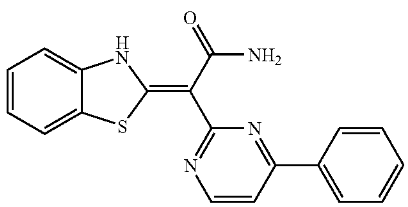 | 346 | 347 |
| 21A | 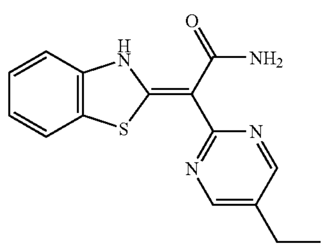 | 298 | 299 |
| 22A | 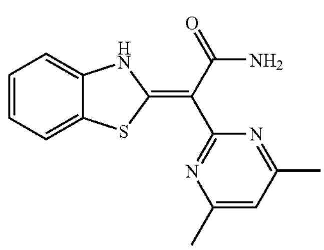 | 298 | 299 |
| 23A | 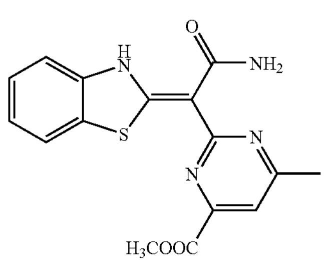 | 342 | 343 |

-continued

| Compound | Structure | Exact mass, M | MS (m/z) |
|---|---|---|---|
| 24A | 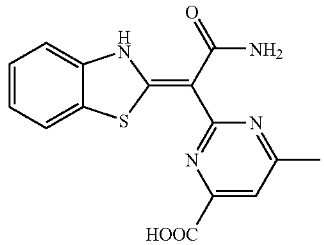 | 328 | 327 (M − H) |
| 25A | 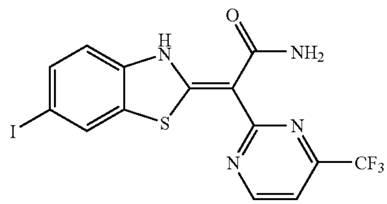 | 464 | 463 (M − H) |
| 26A | 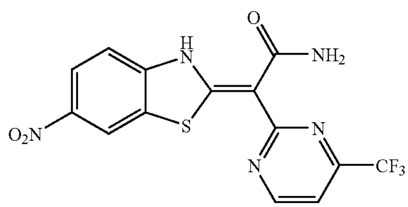 | 383 | 384 |
| 27A | 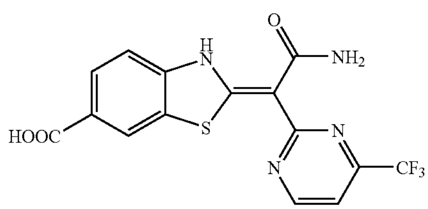 | 382 | 383 |
| 28A | 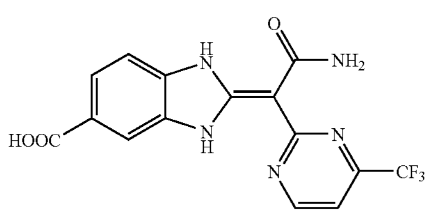 | 365 | 366 |
| 29A | 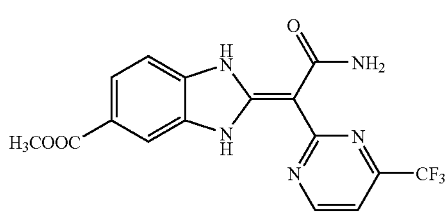 | 379 | 380 |
| 30A | 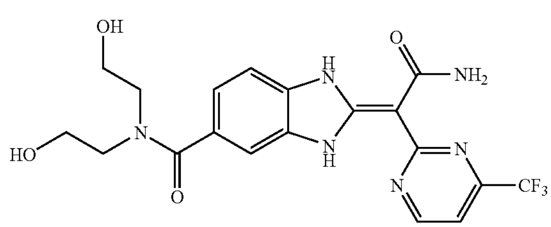 | 452 | 453 |

-continued

| Compound | Structure | Exact mass, M | MS (m/z) |
|---|---|---|---|
| 31A | 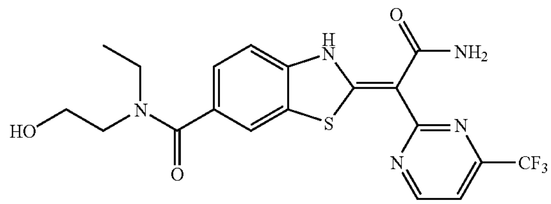 | 453 | 454 |
| 32A | 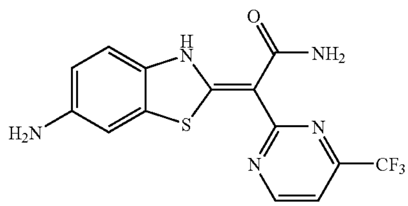 | 353 | 354 |
| 33A | 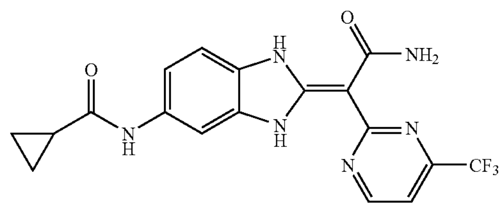 | 404 | 405 |
| 34A | 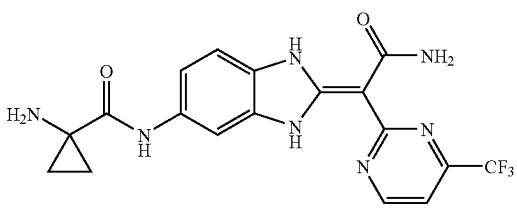 | 419 | 420 |
| 35A | 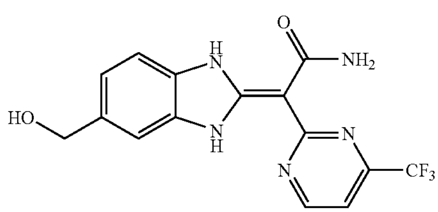 | 351 | 352 |
| 36A | 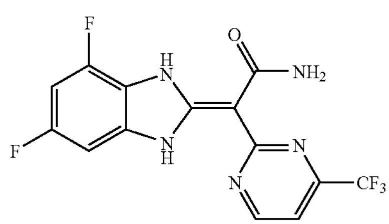 | 357 | 358 |
| 37A | 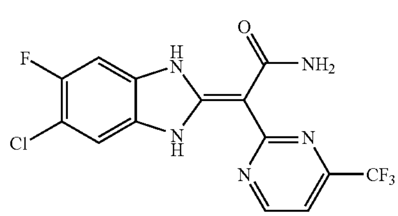 | 373 | 374 |

-continued

| Compound | Structure | Exact mass, M | MS (m/z) |
|---|---|---|---|
| 38A | 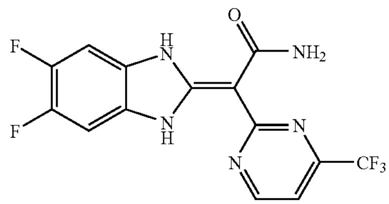 | 357 | 358 |
| 39A | 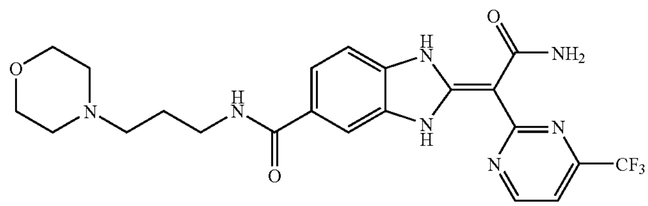 | 491 | 492 |
| 40A | 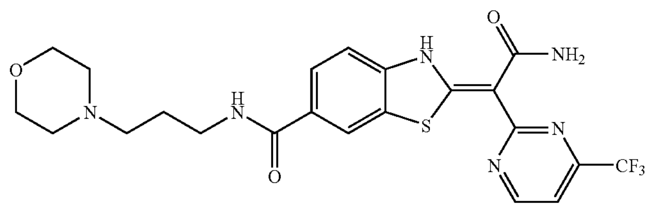 | 508 | 509 |
| 41A | 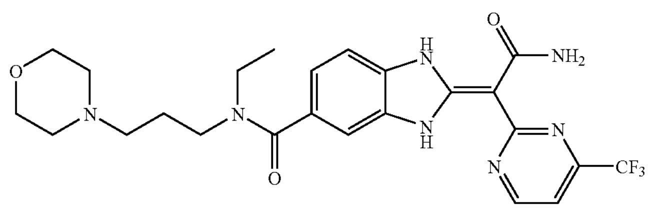 | 519 | 520 |
| 42A | 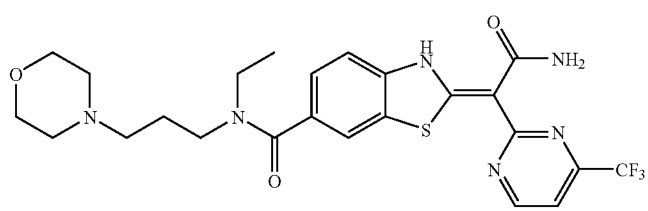 | 536 | 537 |
| 43A | 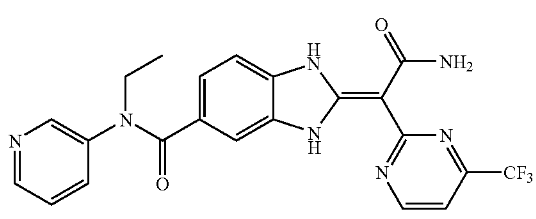 | 469 | 470 |
| 44A | 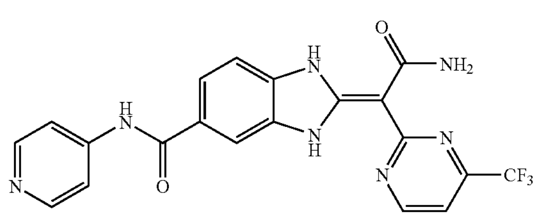 | 441 | 443 (M + 2) |

-continued

| Compound | Structure | Exact mass, M | MS (m/z) |
|---|---|---|---|
| 45A | 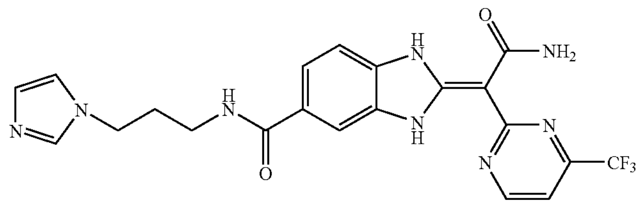 | 472 | 473 |
| 46A | 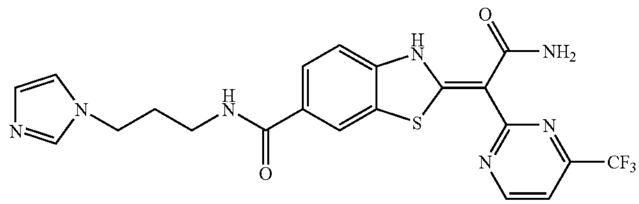 | 489 | 490 |
| 47A | 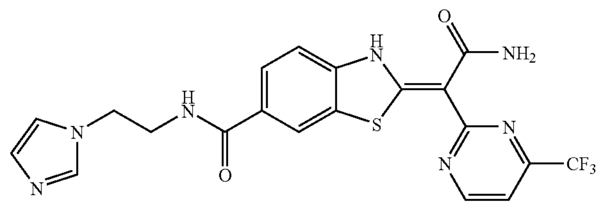 | 475 | 474 (M − H) |
| 48A | 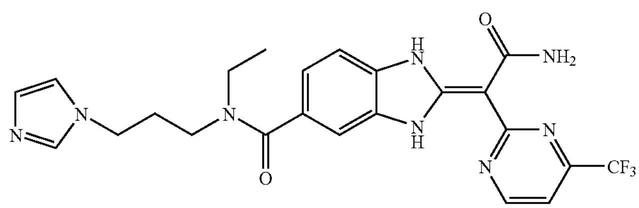 | 500 | 501 |
| 49A | 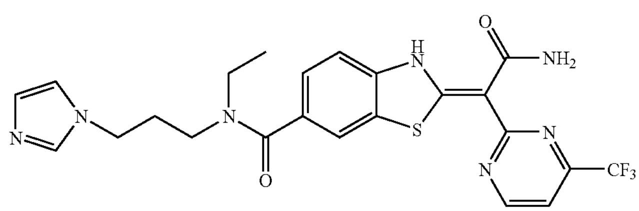 | 517 | 518 |
| 50A | 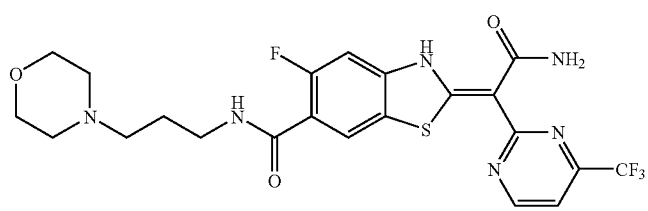 | 526 | 527 |
| 51A | 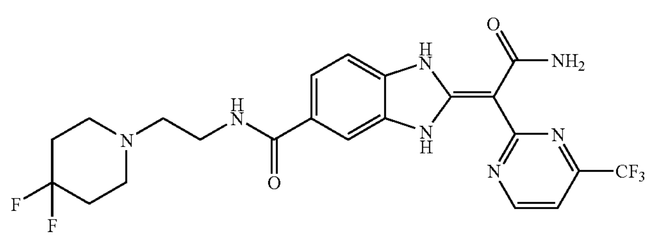 | 511 | 512 |

| Compound | Structure | Exact mass, M | MS (m/z) |
|---|---|---|---|
| 52A | 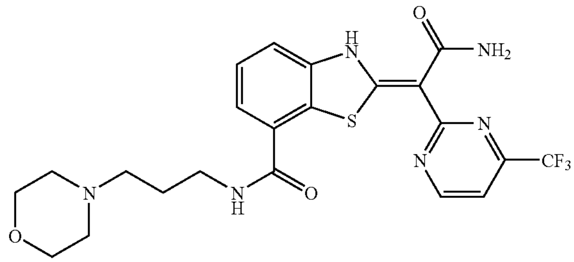 | 508 | 509 |
| 53A | 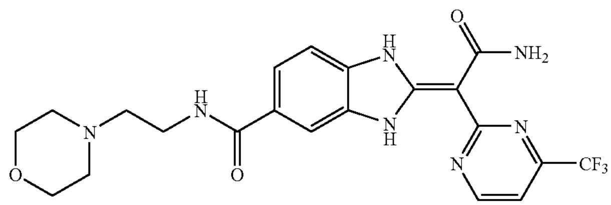 | 477 | 478 |
| 54A | 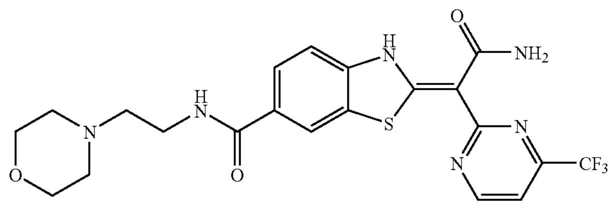 | 494 | 495 |
| 55A | 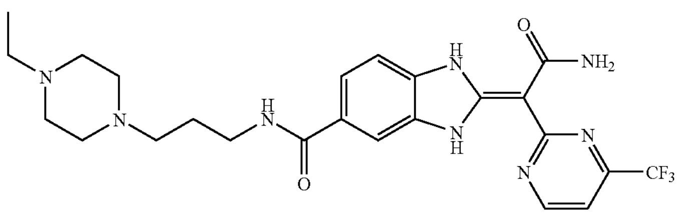 | 518 | 519 |
| 56A | 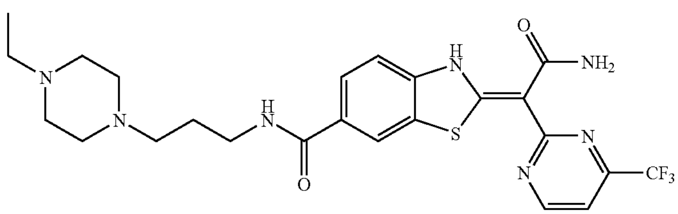 | 535 | 536 |
| 57A | 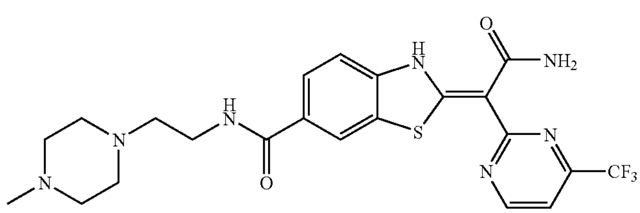 | 507 | 508 |
| 58A | 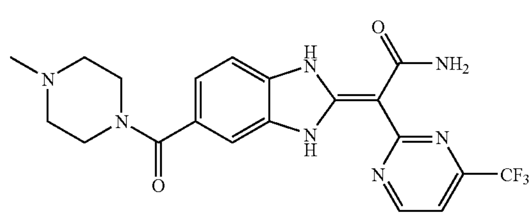 | 447 | 448 |

-continued

| Compound | Structure | Exact mass, M | MS (m/z) |
|---|---|---|---|
| 59A | 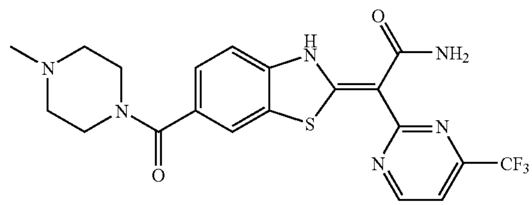 | 464 | 465 |
| 60A | 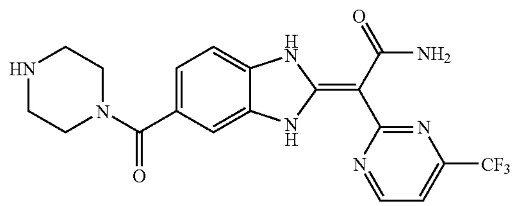 | 433 | 434 |
| 61A | 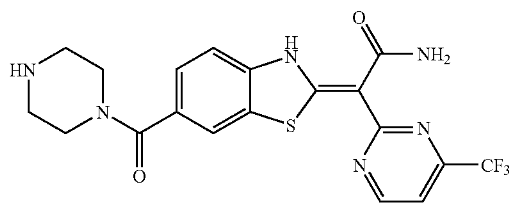 | 450 | 451 |
| 62A | 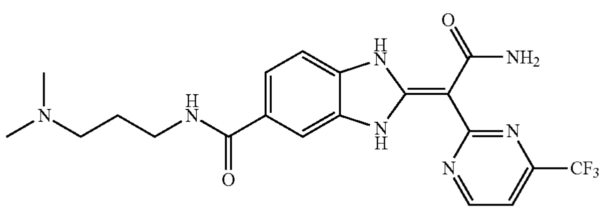 | 449 | 451 |
| 63A | 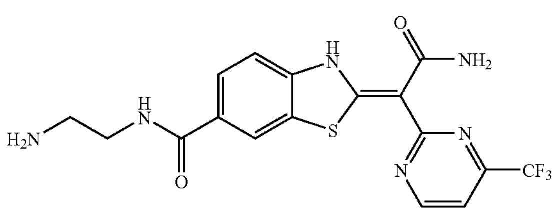 | 424 | 425 |
| 64A | 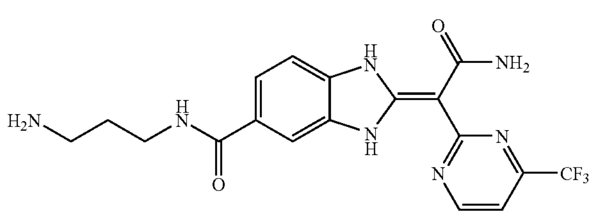 | 421 | 422 |
| 65A | 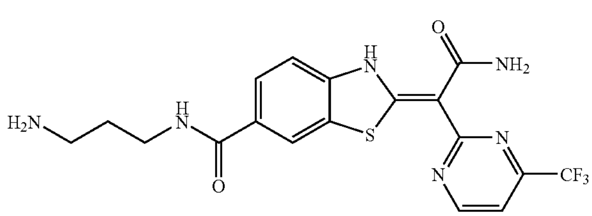 | 438 | 439 |

-continued

| Compound | Structure | Exact mass, M | MS (m/z) |
|---|---|---|---|
| 66A | 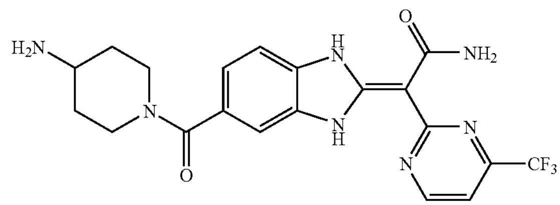 | 447 | 448 |
| 67A | 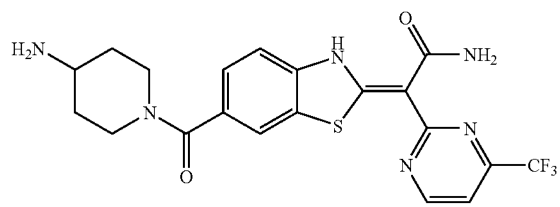 | 464 | 465 |
| 68A | 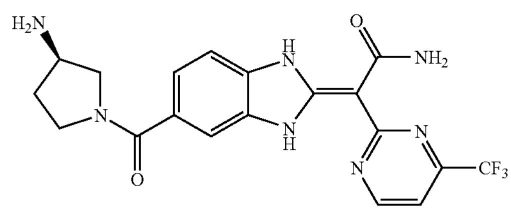 | 433 | 434 |
| 69A | 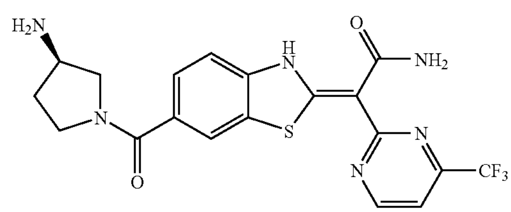 | 450 | 451 |
| 70A | 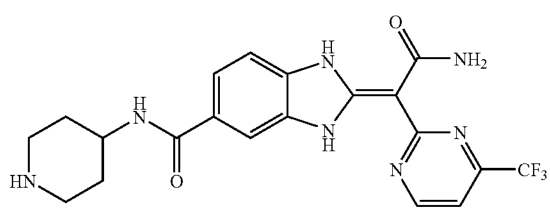 | 447 | 448 |
| 71A | 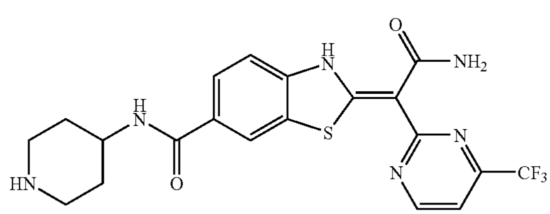 | 464 | 465 |
| 72A | 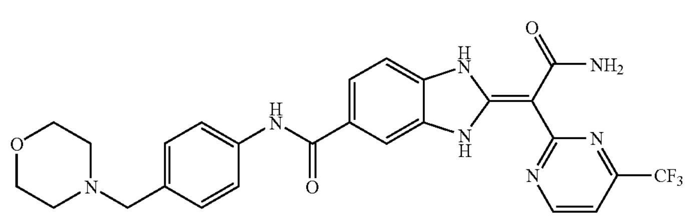 | 540 | 540 |

-continued

| Compound | Structure | Exact mass, M | MS (m/z) |
|---|---|---|---|
| 73A | 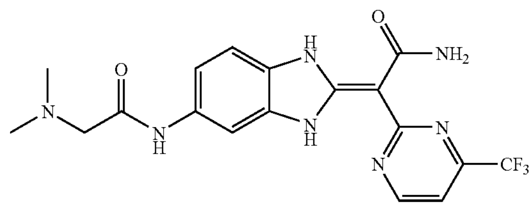 | 421 | 422 |
| 74A | 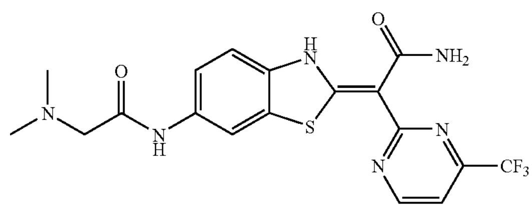 | 438 | 439 |
| 75A | 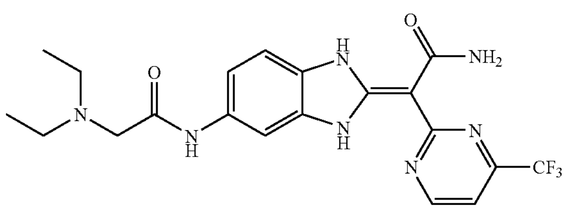 | 449 | 450 |
| 76A | 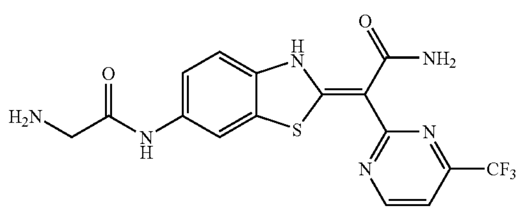 | 410 | 411 |
| 77A | 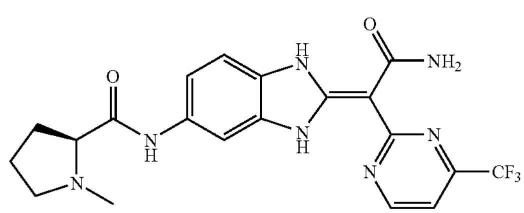 | 447 | 448 |
| 78A | 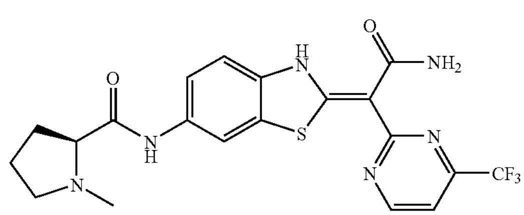 | 464 | 465 |
| 79A | 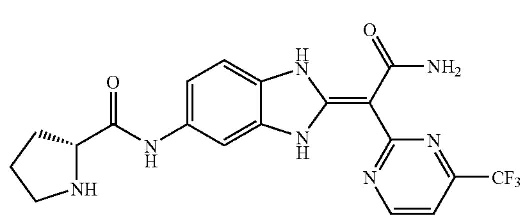 | 433 | 434 |

-continued

| Compound | Structure | Exact mass, M | MS (m/z) |
|---|---|---|---|
| 80A | 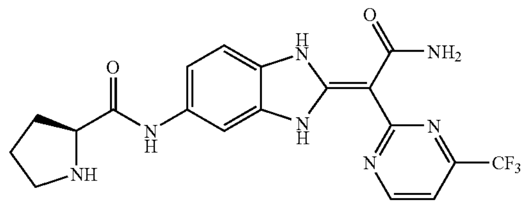 | 433 | 434 |
| 81A | 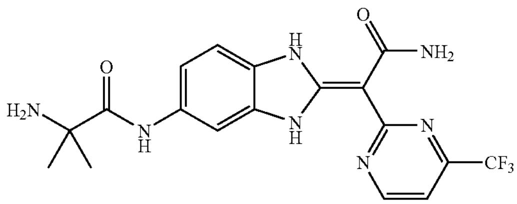 | 421 | 422 |
| 82A | 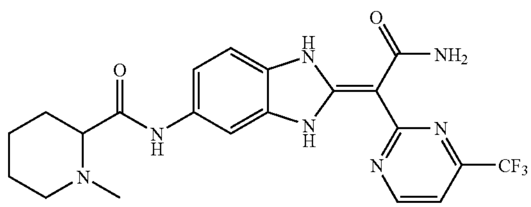 | 461 | 462 |
| 83A | 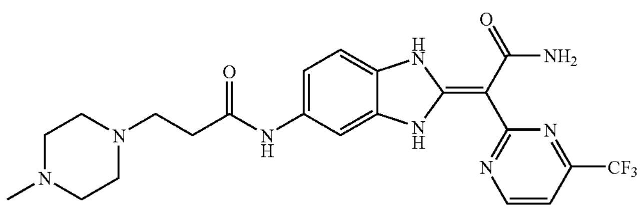 | 490 | 491 |
| 84A | 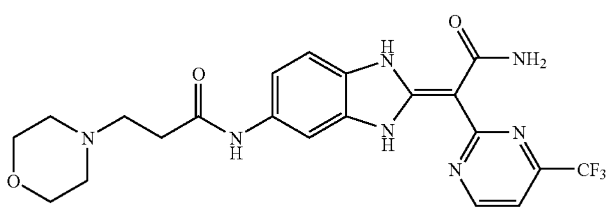 | 477 | 478 |
| 85A | 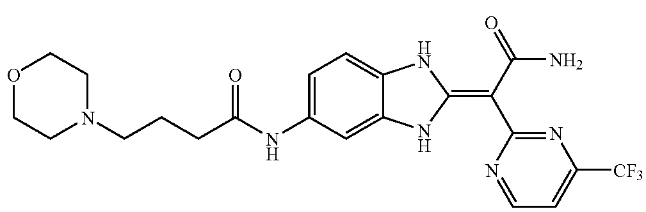 | 491 | 492 |
| 86A | 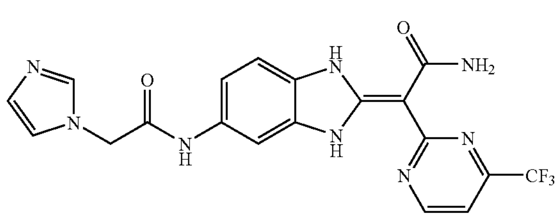 | 444 | 445 |

-continued

| Compound | Structure | Exact mass, M | MS (m/z) |
|---|---|---|---|
| 87A | 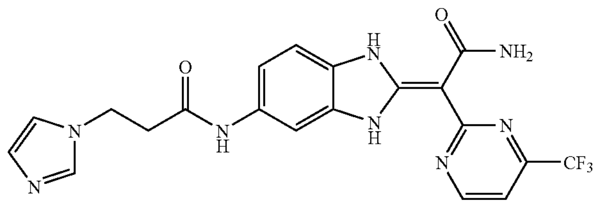 | 458 | 459 |
| 88A | 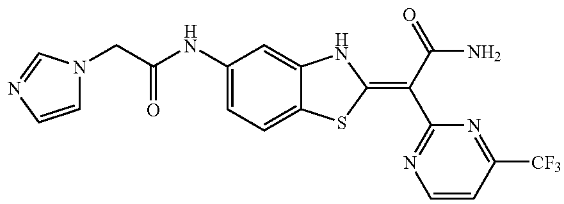 | 461 | 462 |
| 89A | 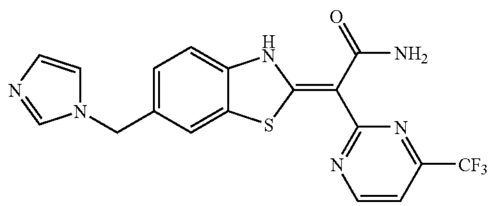 | 418 | 419 |
| 90A | 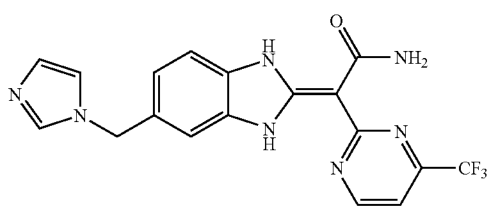 | 401 | 402 |
| 91A | 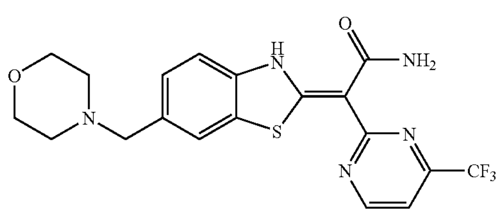 | 437 | 438 |
| 92A | 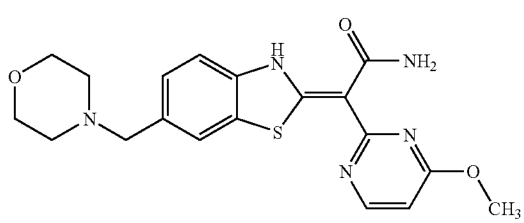 | 399 | 400 |
| 93A | 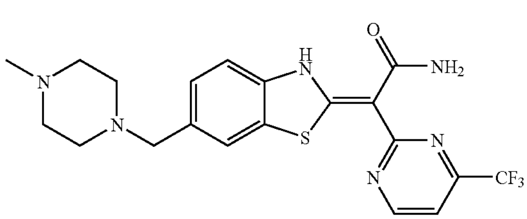 | 450 | 451 |

-continued

| Compound | Structure | Exact mass, M | MS (m/z) |
|---|---|---|---|
| 94A | 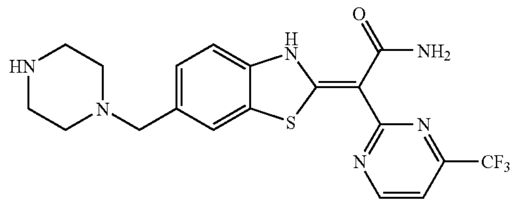 | 436 | 437 |
| 95A | 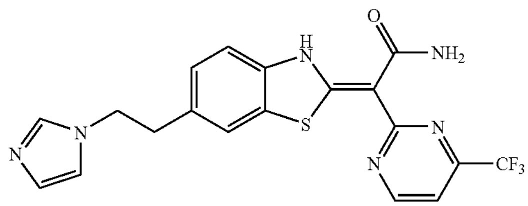 | 432 | 433 |
| 96A | 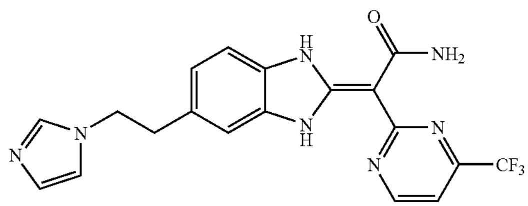 | 415 | 416 |
| 97A | 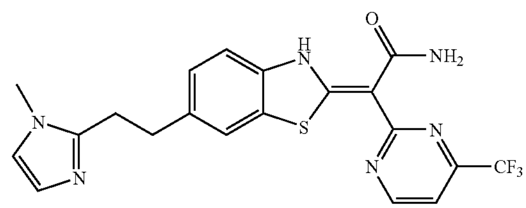 | 446 | 447 |
| 98A | 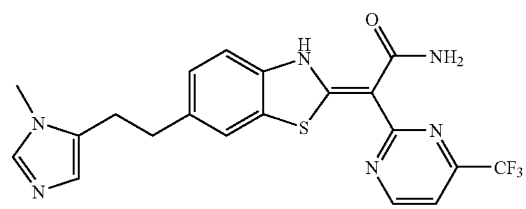 | 446 | 447 |
| 99A | 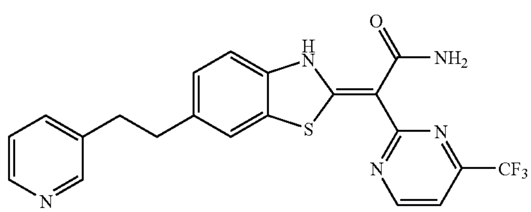 | 443 | 444 |
| 100A | 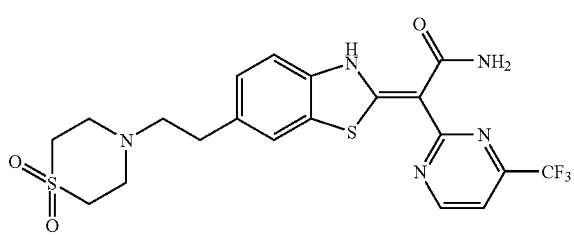 | 499 | 500 |

-continued

| Compound | Structure | Exact mass, M | MS (m/z) |
|---|---|---|---|
| 101A | 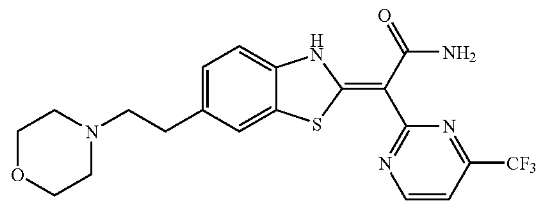 | 451 | 452 |
| 102A | 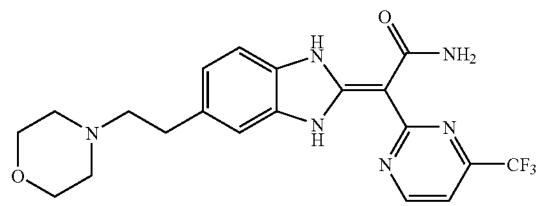 | 434 | 435 |
| 103A | 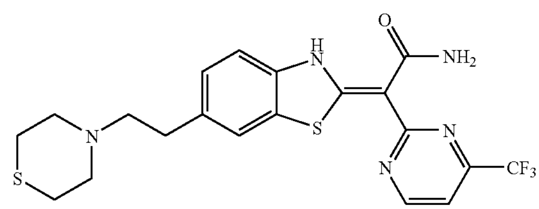 | 467 | 468 |
| 104A | 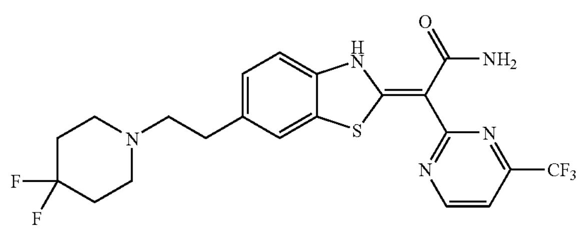 | 485 | 486 |
| 105A | 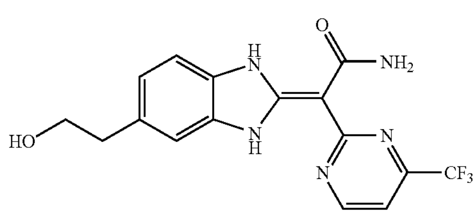 | 365 | 366 |
| 106A | 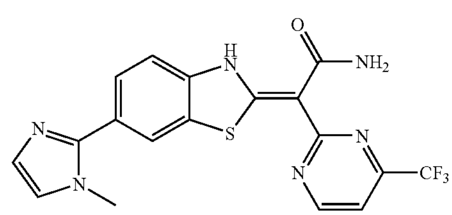 | 418 | 419 |
| 107A | 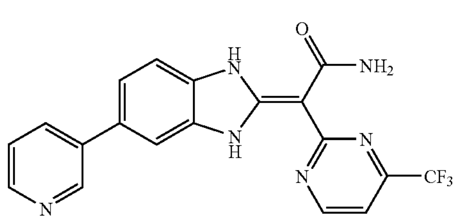 | 398 | 399 |

-continued

| Compound | Structure | Exact mass, M | MS (m/z) |
|---|---|---|---|
| 108A | 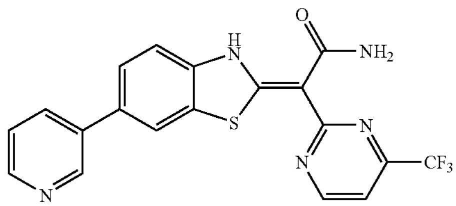 | 415 | 416 |
| 109A | 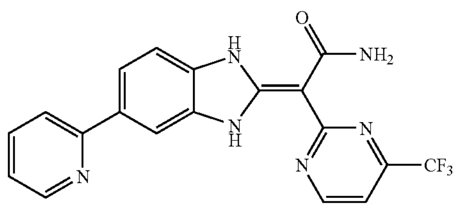 | 398 | 399 |
| 110A | 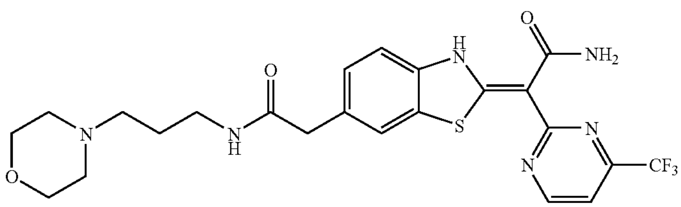 | 522 | 523 |
| 111A | 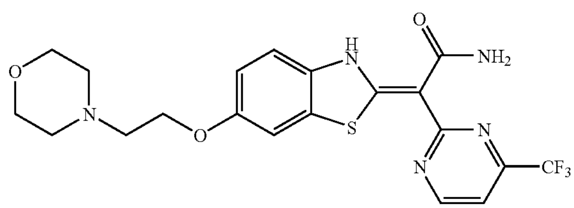 | 467 | 468 |
| 112A | 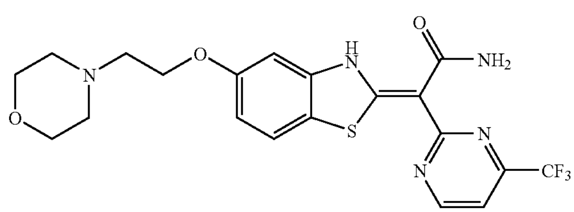 | 467 | 468 |
| 113A | 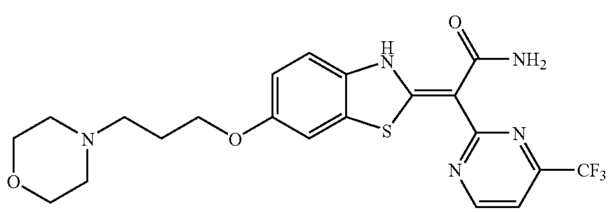 | 481 | 482 |
| 114A | 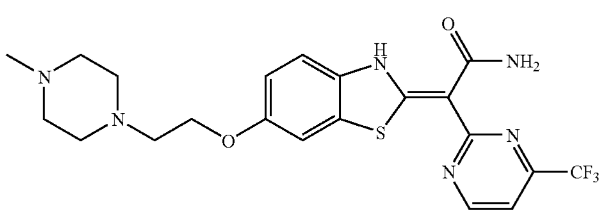 | 480 | 481 |

-continued

| Compound | Structure | Exact mass, M | MS (m/z) |
|---|---|---|---|
| 115A | 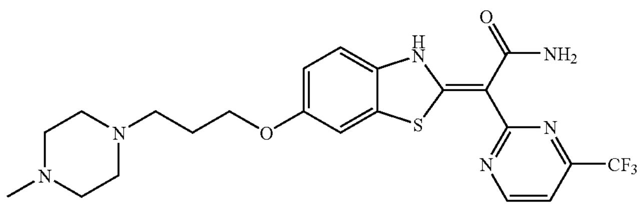 | 494 | 495 |
| 116A | 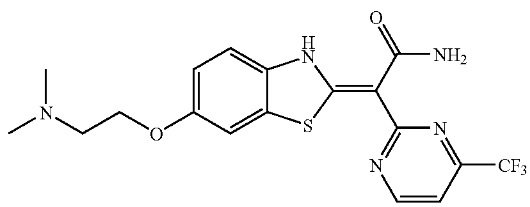 | 425 | 426 |
| 117A | 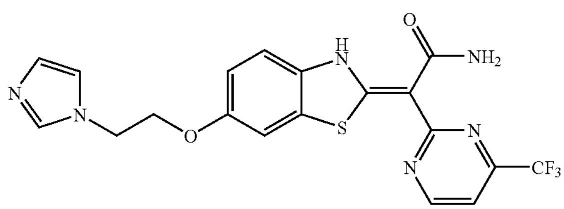 | 448 | 449 |
| 118A | 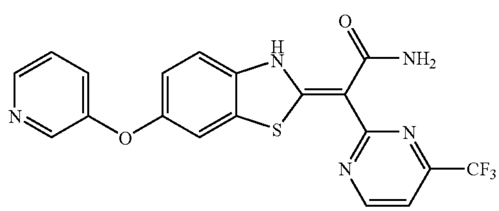 | 431 | 432 |
| 119A | 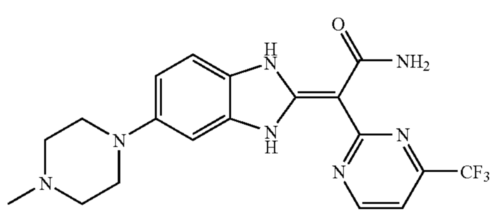 | 419 | 420 |
| 120A | 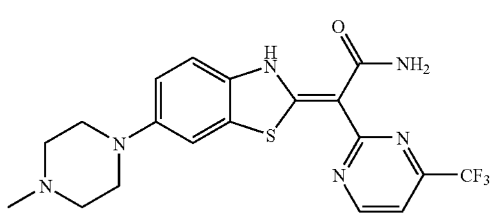 | 436 | 437 |
| 121A | 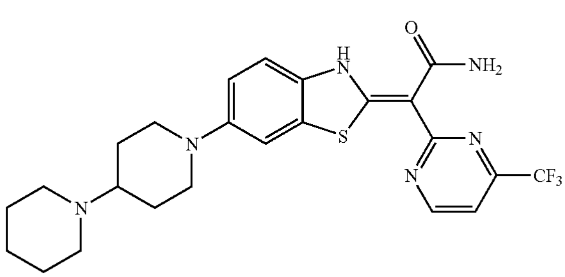 | 504 | 505 |

-continued

| Compound | Structure | Exact mass, M | MS (m/z) |
|---|---|---|---|
| 122A | 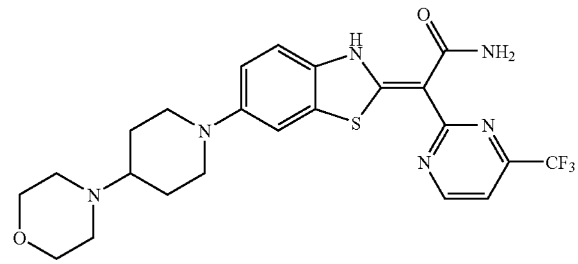 | 506 | 507 |
| 123A | 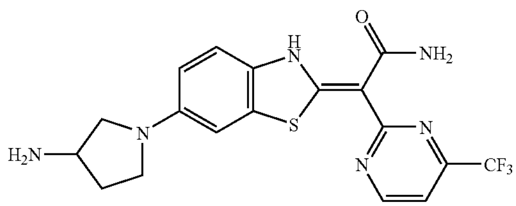 | 422 | 423 |
| 124A | 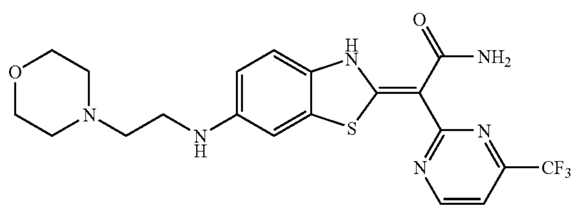 | 466 | 467 |
| 125A | 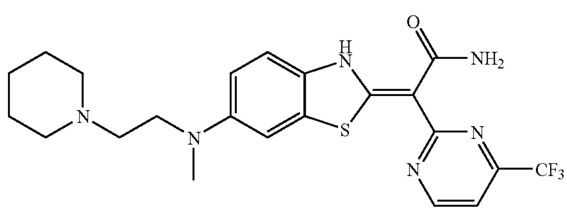 | 478 | 479 |
| 126A | 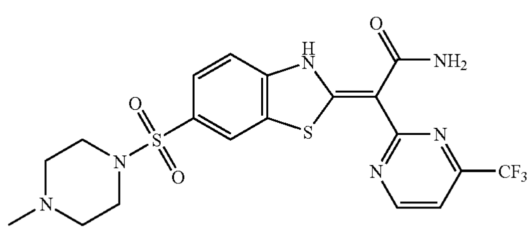 | 500 | 501 |
| 127A | 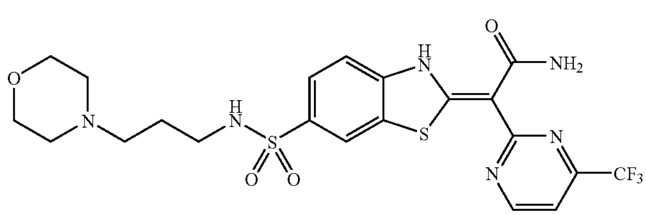 | 544 | 545 |
| 128A | 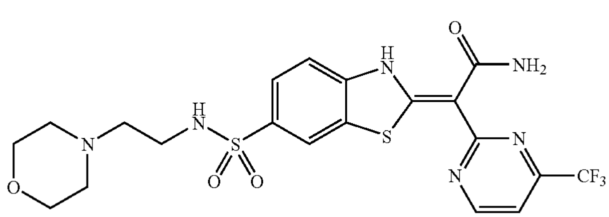 | 530 | 531 |

| Compound | Structure | Exact mass, M | MS (m/z) |
|---|---|---|---|
| 129A | 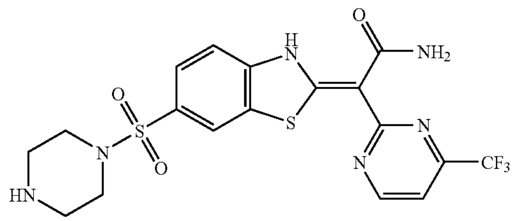 | 486 | 487 |
| 130A | 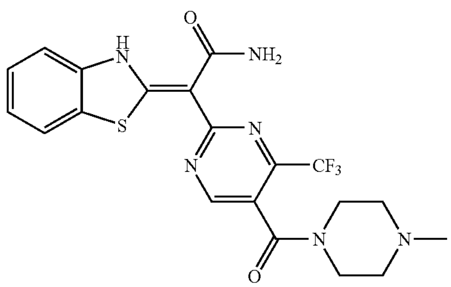 | 464 | 465 |
| 131A | 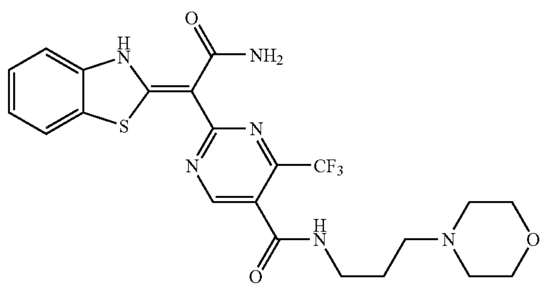 | 508 | 509 |
| 132A | 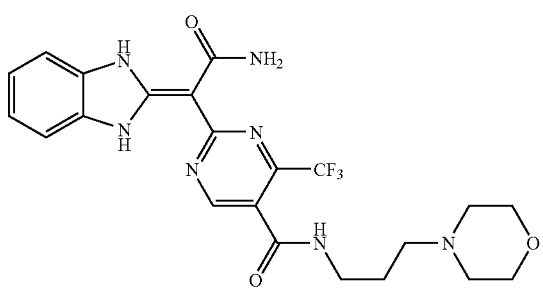 | 491 | 492 |
| 133A | 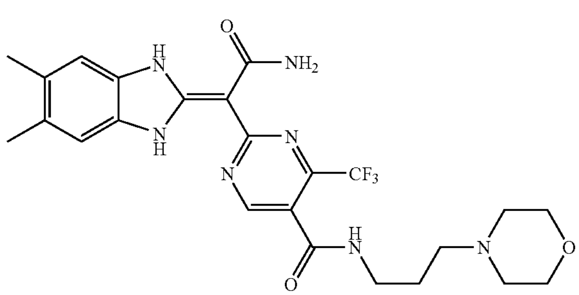 | 519 | 520 |

-continued

| Compound | Structure | Exact mass, M | MS (m/z) |
|---|---|---|---|
| 134A | 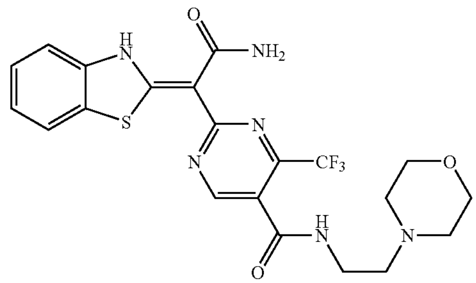 | 494 | 495 |
| 135A | 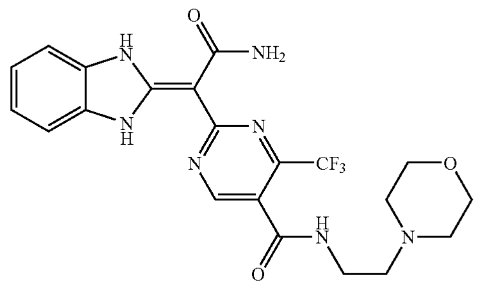 | 477 | 478 |
| 136A | 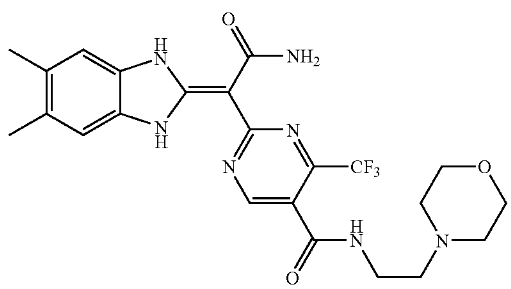 | 505 | 506 |
| 137A | 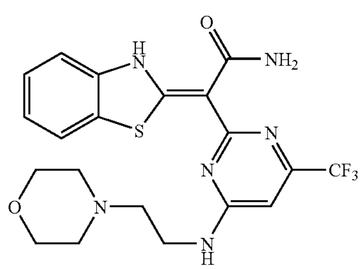 | 466 | 467 |
| 138A | 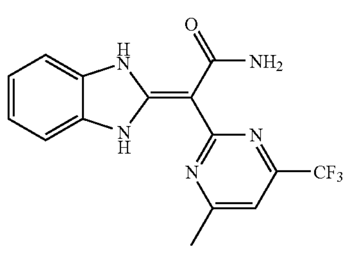 | 335 | 336 |
| 139A | 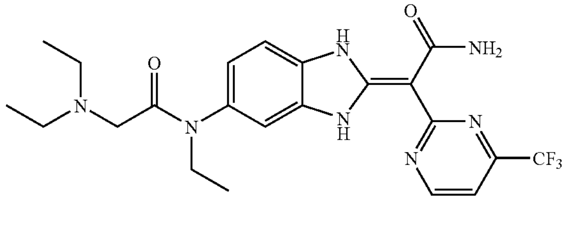 | 477 | 478 |

| Compound | Structure | Exact mass, M | MS (m/z) |
|---|---|---|---|
| 140A | | 461 | 462 |
| 141A | 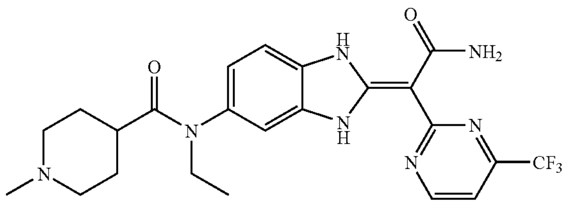 | 489 | 490 |
| 142A | 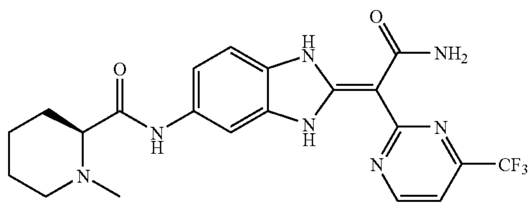 | 461 | 462 |
| 143A | 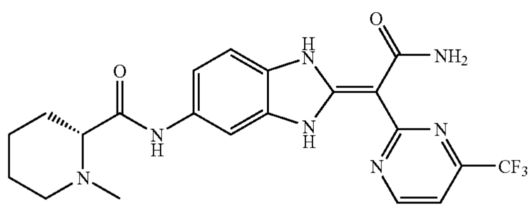 | 461 | 462 |
| 144A | 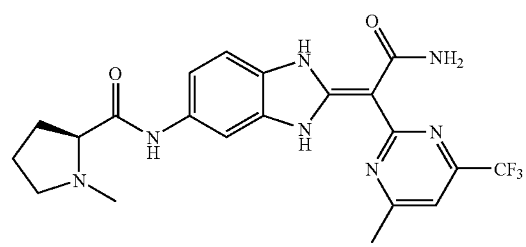 | 461 | 462 |
| 145A | 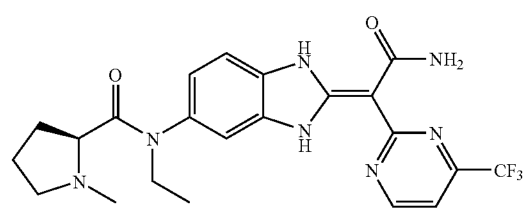 | 475 | 476 |
| 146A | 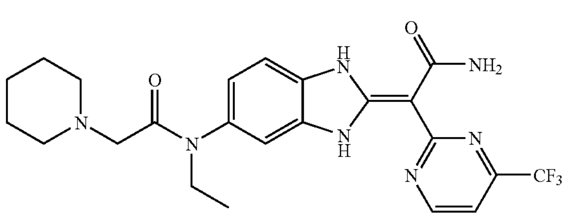 | 489 | 490 |

Other compounds of the invention may be similarly prepared using methods well known to a person of ordinary skill in the art having regard to that skill and this disclosure.

IN VITRO EXAMPLES

The following examples illustrate the inhibition of cancer-related kinases (Aurora A and B and VEGFR2 kinases) by compounds of the first aspect of this invention and the cytotoxic/cytostatic effect of the compounds against human cancer cell lines in vitro. These results are considered predictive of efficacy in human cancer chemotherapy, as other anticancer agents tested in these assays have shown anticancer activity in humans.

The cell lines HL60 (human promyelocytic leukemia) and HCT116 (human colon carcinoma) were obtained from the American Type Culture Collection, Manassas, Va., U.S.A., and HUVEC-2 (human umbilical vein endothelial cells) from BD Biosciences, Bedford, Mass., U.S.A. Aurora A kinase was obtained from Upstate Biotech, Billerica, Mass., U.S.A.; Aurora B kinase from BPS Bioscience, San Diego, Calif., U.S.A.; and VEGFR2 kinase from Cell Signaling Technology, Danvers, Mass., U.S.A. The IMAP FP Screening Express kit was obtained from Molecular Devices, Sunnyvale, Calif., U.S.A.; the CellTiter-Glo assay kit from Promega Corporation, Madison, Wis., U.S.A.; and the Cellular DNA Cytometric Analysis Reagent Kit and BrdU labeling and detection kit from Roche Diagnostics Corporation, Indianapolis, Ind., U.S.A. All products were used in accordance with manufacturer's directions. Kinase inhibition assays and the histone phosphorylation (p-H3) assay were conducted in duplicate, and the cytotoxicity and HUVEC proliferation assays were conducted in triplicate, in each case with solvent control.

In Vitro Example 1

Aurora A and B Kinase Assays

Aurora A kinase assay: the test compounds were diluted in dimethylsulfoxide (DMSO, eight concentrations with serial 3-fold dilutions) and incubated (final DMSO concentration 2.5%) with Aurora A kinase at room temperature for 5 min in kinase reaction buffer with 1 mM dithiothreitol (IMAP FP Screening Express). The kinase reaction was initiated by adding 100 nM fluorescein labeled PKAtide and 10 µM adenosine triphosphate (ATP), and allowed to continue for 45 min at room temperature, after which it was stopped by adding binding reagent (1:400 dilution in binding buffer A). After 30 min of room temperature incubation with shaking, the fluorescence polarization was measured on a LJL plate reader. Aurora B kinase assay: performed as for the Aurora A kinase assay, but using Aurora B kinase instead of Aurora A kinase.

In Vitro Example 2

VEGFR2 Kinase Assay

This assay was performed as for the Aurora A kinase assay, using VEGFR2 kinase, CSKtide as the substrate with 6 µM ATP and 1 mM $MnCl_2$, a kinase reaction time of 1 hr, and dilution of the binding reagent 1:1200 in binding buffer A/binding buffer B (1:1).

In Vitro Example 3

Histone Phosphorylation (p-H3) Assay

Log phase HCT116 cells were seeded at $2.5 \times 10^4$ cells/well in a 96-well plate and allowed to attach overnight. The test compounds were diluted in DMSO (8 concentrations with serial 3-fold dilutions) and added to the cells (0.5% DMSO final concentration), and the cells incubated for 4 hr. The cells were then washed three times with cold phosphate-buffered saline (PBS), and lysis buffer was added. After 30 min shaking at 4° C. and centrifugation, the supernatants were transferred to a nitrocellulose membrane by a "dot-blot" apparatus. After washing the wells, the membrane was processed for Western blot. Detection of p-H3 and β-actin was performed on the same membrane with primary rabbit anti-p-H3 and mouse anti-β-actin antibodies followed by secondary goat anti-rabbit IRDye800 and goat anti-mouse AlexaFluor 680 antibodies. The membranes were scanned on an Odyssey scanner.

In Vitro Example 4

HL60 and HCT116 Cytotoxicity Assays

Log-phase cells were trypsinized, collected by centrifugation, and resuspended in a small volume of fresh medium, and the density of viable cells was determined following Trypan Blue staining. Cells were diluted in fresh media ($1 \times 10^4$ cells/mL for HL60 and $4 \times 10^4$ cells/mL for HCT116 cells), the test compounds (concentrations between 0.1 µM and 200 µM, dissolved in DMSO, 50 µL) added immediately after dilution to achieve a final DMSO concentration of 0.5%, then the suspensions added at 150 µL/well to 96-well plates, and incubated overnight to allow attachment in the case of adherent cells. The cells were cultured for three days (about three doubling times). The cells were then collected by centrifugation, and 100 µL of the culture supernatant was replaced by the CellTiter-Glo reagent. After incubation for 15 minutes at room temperature, the plate was read with a luminometer.

In Vitro Example 5

HUVEC VEGF-Dependent Proliferation Assay

HUVEC-2 cells were seeded at $10^4$ cells/well in a 96-well plate coated with 0.1% gelatin in complete medium. After incubation at 37° C. overnight, the cells were washed twice with PBS, Medium 199 with 0.1% fetal bovine serum was added, and the cells were incubated for one day. The compounds were serially diluted in DMSO, and added to the cells at 0.5% DMSO final concentration. After 2 hr, VEGF (25 ng/mL) was added; and after a further day, 5-bromo-2-deoxyuridine (BrdU, 10 µM) was added to label proliferating cells, and the cells incubated for another day. The plates were then processed using the Roche BrdU labeling and detection kit, and the VEGF-dependent antiproliferative activity of the compounds determined.

Compounds of formula A showed the following activity in these in vitro assays. All numbers are rounded to 1 significant figure; numbers ">x" indicate that the result was greater than the maximum limit of quantitation of the assay.

| Cpd. | Aur-A IC$_{50}$, nM | Aur-B IC$_{50}$, nM | VEGFR2 IC$_{50}$, nM | p-H3 IC$_{50}$, μM | HCT116 IC$_{50}$, μM | HL60 IC$_{50}$, μM | HUVEC IC$_{50}$, μM |
|---|---|---|---|---|---|---|---|
| 1A | 10 | 5 | 10 | 0.2 | 0.3 | 1 | 0.07 |
| 2A | 30 | 6 | 90 | 2 | 2 | 3 | 0.05 |
| 3A | 20 | 10 | 90 | 20 | 3 | | |
| 4A | 4 | 10 | 30 | >40 | 2 | | |
| 5A | 20 | 8 | 20 | 3 | 10 | >10 | |
| 6A | 20 | 10 | 200 | 2 | 4 | 2 | |
| 7A | 7 | 20 | 30 | >5 | 6 | 0.08 | |
| 8A | 10 | 8 | 60 | 1 | 2 | 0.2 | |
| 9A | 10 | 7 | 60 | >5 | >20 | >20 | |
| 10A | 10 | 10 | 40 | 5 | 1 | 2 | |
| 11A | 40 | 10 | | >5 | 4 | 3 | |
| 12A | 7 | 6 | 40 | 0.1 | 0.4 | 0.2 | |
| 13A | 10 | 3 | | 0.8 | 0.7 | 1 | |
| 14A | 50 | 30 | 80 | >50 | 8 | | |
| 15A | 80 | 30 | 40 | 2 | 2 | | |
| 16A | 100 | 20 | 300 | 2 | 2 | | 2 |
| 17A | 300 | 30 | 1 | 0.6 | 5 | 5 | |
| 18A | 200 | 40 | 500 | 2 | 20 | | |
| 19A | 400 | 30 | | >50 | 20 | | |
| 20A | 90 | 20 | 200 | >5 | 8 | 0.6 | |
| 21A | 200 | 100 | 1000 | | 20 | | |
| 22A | 80 | 10 | 200 | 2 | 10 | | |
| 23A | 70 | 6 | 100 | 8 | 50 | | |
| 24A | 900 | 1000 | 400 | | >50 | | |
| 25A | 200 | 100 | 400 | >50 | 10 | | |
| 26A | 200 | 100 | 1000 | >50 | 20 | | |
| 27A | 3 | 9 | 10 | 1 | 7 | | |
| 28A | 5 | 5 | 10 | 4 | 4 | | 0.04 |
| 29A | 30 | 10 | 100 | >5 | 0.2 | | |
| 30A | 10 | 10 | 8 | 1 | | | |
| 31A | 4 | 9 | 3 | 0.1 | 0.2 | 1 | |
| 32A | 10 | 10 | 40 | 0.4 | 5 | 3 | |
| 33A | 2 | 10 | 9 | 0.5 | 0.3 | 0.3 | |
| 34A | 5 | 6 | 10 | 0.4 | 0.6 | 0.2 | |
| 35A | 9 | 5 | 20 | 0.6 | 0.2 | | |
| 36A | 30 | 40 | 200 | >5 | 4 | | |
| 37A | 30 | 20 | 400 | 0.5 | 2 | 4 | |
| 38A | 40 | 10 | 200 | 0.3 | 0.8 | 1 | 0.1 |
| 39A | 10 | 5 | 7 | 0.9 | 0.3 | 0.5 | 0.06 |
| 40A | 3 | 7 | 3 | 0.5 | 0.2 | 7 | 0.03 |
| 41A | 6 | 4 | 4 | 0.1 | 0.7 | 0.1 | 0.2 |
| 42A | 10 | 6 | 20 | 0.3 | 0.5 | 0.03 | 0.04 |
| 43A | 6 | 10 | | | | | |
| 44A | 10 | 10 | 10 | 0.2 | 0.2 | | 0.08 |
| 45A | 20 | 7 | 20 | 0.9 | 0.5 | 0.1 | 0.01 |
| 46A | 6 | 10 | 40 | 0.2 | 0.4 | 0.2 | |
| 47A | 4 | 6 | 20 | 0.2 | 0.3 | 0.3 | 0.004 |
| 48A | 10 | 1 | 10 | 0.3 | 0.6 | 0.1 | 0.04 |
| 49A | 3 | 5 | | 0.1 | 0.4 | 1 | |
| 50A | 20 | 10 | 20 | 0.4 | 0.3 | | 0.09 |
| 51A | 7 | 6 | 20 | 0.3 | 0.5 | 0.05 | 0.03 |
| 52A | 60 | 60 | 100 | >50 | 1 | | |
| 53A | 3 | 10 | 20 | 0.2 | 0.3 | 0.2 | 0.03 |
| 54A | 6 | 10 | 10 | 0.4 | 0.4 | 0.3 | 0.03 |
| 55A | 20 | 20 | 20 | 0.7 | 0.3 | | 0.05 |
| 56A | 20 | 20 | 20 | 0.7 | 0.04 | | 0.04 |
| 57A | 20 | 20 | 10 | 0.1 | 0.1 | | 0.02 |
| 58A | 9 | 5 | 9 | 0.5 | 0.4 | | 0.06 |
| 59A | 8 | 20 | 6 | 0.09 | 0.4 | | 0.05 |
| 60A | 10 | 7 | 5 | 0.2 | 0.2 | | 0.08 |
| 61A | 20 | 10 | 4 | 0.03 | 0.1 | 0.2 | 0.02 |
| 62A | 70 | 10 | 6 | 0.4 | 0.06 | | 0.06 |
| 63A | 30 | 30 | 5 | 0.4 | 0.2 | | 0.06 |
| 64A | 50 | 20 | 10 | 0.9 | 2 | | |
| 65A | 30 | 20 | 7 | 0.4 | 0.2 | | |
| 66A | 20 | 10 | 2 | 0.2 | 0.2 | | 0.05 |
| 67A | 10 | 40 | 4 | 0.04 | 0.2 | | 0.02 |
| 68A | 10 | 10 | 3 | 0.06 | 0.1 | | 0.06 |
| 69A | 20 | 30 | 2 | 0.1 | 0.09 | | 0.02 |
| 70A | 60 | 10 | 4 | 1 | 0.6 | | |
| 71A | 20 | 40 | 4 | 0.2 | 0.2 | | 0.09 |
| 72A | 20 | 20 | 20 | 0.3 | 0.2 | | 0.08 |
| 73A | 10 | 5 | 6 | 0.1 | 0.2 | 0.2 | 0.1 |
| 74A | 20 | 10 | 20 | 0.2 | 0.3 | 0.04 | 0.08 |
| 75A | 60 | 10 | 50 | 0.4 | 1 | | 0.2 |
| 76A | 50 | 5 | 80 | 0.2 | 0.7 | | 0.1 |
| 77A | 8 | 7 | 9 | 0.1 | 0.2 | 0.3 | 0.09 |

-continued

| Cpd. | Aur-A IC$_{50}$, nM | Aur-B IC$_{50}$, nM | VEGFR2 IC$_{50}$, nM | p-H3 IC$_{50}$, µM | HCT116 IC$_{50}$, µM | HL60 IC$_{50}$, µM | HUVEC IC$_{50}$, µM |
|---|---|---|---|---|---|---|---|
| 78A | 60 | 40 | 50 | 0.6 | 2 | 1 | 0.4 |
| 79A | 20 | 20 | 10 | 0.4 | 0.1 | 0.3 | 0.04 |
| 80A | 10 | 4 | 50 | 0.09 | 0.5 | | 0.1 |
| 81A | 6 | 7 | 9 | 0.09 | 0.3 | 0.2 | 0.08 |
| 82A | 8 | 7 | 10 | 0.4 | 0.08 | | 0.03 |
| 83A | 6 | 10 | 60 | 0.2 | 0.2 | | 0.2 |
| 84A | 7 | 9 | 20 | 0.1 | 0.2 | 0.1 | 0.06 |
| 85A | 5 | 4 | 20 | 0.05 | 0.3 | 0.06 | 0.02 |
| 86A | 4 | 8 | 30 | 0.2 | 0.4 | 0.8 | 0.03 |
| 87A | 8 | 9 | 10 | 0.2 | 0.2 | 0.1 | 0.09 |
| 88A | 4 | 8 | 20 | 0.06 | 0.3 | 0.1 | 0.3 |
| 89A | 5 | 5 | 6 | 0.1 | 0.5 | 0.7 | 0.08 |
| 90A | 4 | 9 | 4 | 0.07 | 0.2 | 0.1 | 0.09 |
| 91A | 2 | 20 | 10 | 0.1 | 0.3 | | 0.04 |
| 92A | 70 | 30 | 400 | 0.5 | 5 | | 0.06 |
| 93A | 20 | 20 | 10 | 0.1 | 0.3 | | 0.03 |
| 94A | 7 | 7 | 10 | 0.08 | 0.2 | 0.1 | 0.05 |
| 95A | 20 | 4 | 20 | 0.05 | 2 | 2 | 0.05 |
| 96A | 2 | 3 | 6 | 0.04 | 0.3 | 0.1 | |
| 97A | 20 | 7 | | 0.1 | 0.6 | 1 | |
| 98A | 6 | 8 | | | | | |
| 99A | 20 | 7 | 100 | 1 | 3 | 2 | |
| 100A | 5 | 9 | 10 | 0.3 | 0.4 | 0.09 | 0.02 |
| 101A | 7 | 9 | 20 | 1 | 1 | 2 | 0.05 |
| 102A | 4 | 7 | | 0.05 | | | |
| 103A | 20 | 10 | 20 | 2 | 2 | 0.1 | 0.1 |
| 104A | 30 | 10 | 60 | 2 | 3 | 1 | |
| 105A | 5 | 7 | | 0.1 | | | |
| 106A | 3 | 20 | 30 | 0.9 | 2 | | 0.08 |
| 107A | 8 | 20 | 40 | >5 | 5 | 1 | |
| 108A | 10 | 10 | 60 | 3 | 2 | 2 | |
| 109A | 20 | 9 | 50 | >5 | 3 | 0.5 | |
| 110A | 50 | 20 | 20 | 0.2 | 0.2 | 0.8 | 0.08 |
| 111A | 20 | 9 | 100 | 0.4 | 2 | | 0.3 |
| 112A | 20 | 20 | 200 | 0.9 | 2 | | 0.2 |
| 113A | 30 | 20 | 40 | 0.4 | 0.6 | | 0.2 |
| 114A | 40 | 20 | 40 | 0.05 | 0.6 | | 0.04 |
| 115A | 40 | 30 | 20 | 0.2 | 0.1 | | 0.1 |
| 116A | 40 | 8 | 9 | 0.08 | 0.4 | | 0.1 |
| 117A | 10 | 8 | 20 | 0.3 | 0.8 | | 0.06 |
| 118A | 40 | 10 | 100 | 4 | 2 | 0.3 | 0.2 |
| 119A | 9 | 6 | 6 | 0.2 | 1 | | 0.2 |
| 120A | 30 | 9 | 2 | 0.5 | 2 | | 2 |
| 121A | 30 | 8 | 20 | 0.09 | 1 | | 0.9 |
| 122A | 20 | 9 | 20 | 0.4 | 4 | | 7 |
| 123A | 100 | 40 | 90 | 2 | 4 | | |
| 124A | 30 | 30 | 100 | | >20 | | 3 |
| 125A | 30 | 10 | 20 | 0.2 | 3 | | 0.6 |
| 126A | 20 | 20 | 70 | 2 | 2 | | 0.03 |
| 127A | 20 | 6 | 20 | 0.2 | 0.6 | 0.5 | 0.04 |
| 128A | 10 | 20 | 60 | 0.6 | 0.9 | | 0.06 |
| 129A | 30 | 10 | 100 | 1 | 1 | | 0.3 |
| 130A | 100 | 9 | 20 | 0.3 | 2 | | 0.4 |
| 131A | 90 | 60 | 200 | 0.9 | 2 | | 0.8 |
| 132A | 60 | 20 | 100 | 2 | 1 | | 0.6 |
| 133A | 40 | 10 | 60 | 0.3 | 0.8 | | 0.2 |
| 134A | 50 | 10 | 80 | 0.4 | 4 | | 0.6 |
| 135A | 30 | 20 | 100 | 0.5 | 4 | | 0.6 |
| 136A | 20 | | 30 | 0.2 | 0.8 | 0.2 | 0.2 |
| 137A | 80 | 30 | 40 | 2 | 2 | | |
| 138A | 8 | 8 | 40 | 0.5 | 1 | 0.4 | |
| 139A | 20 | 2 | 30 | 0.09 | 0.03 | 0.04 | |
| 140A | 6 | 9 | 20 | 0.4 | 0.4 | 0.3 | 0.02 |
| 141A | 4 | 6 | 40 | 0.3 | 0.9 | 1 | 0.02 |
| 142A | 2 | 4 | 10 | 0.3 | 0.3 | 0.2 | 0.09 |
| 143A | 4 | 6 | 30 | 0.2 | 0.3 | 0.3 | 0.08 |
| 144A | 5 | 6 | | 0.1 | 0.4 | 0.5 | |
| 145A | 20 | 4 | 10 | 0.08 | 0.2 | 0.4 | |
| 146A | 20 | 5 | | 0.2 | 0.4 | 0.8 | |

In Vitro Example 6

Cell Cycle Analysis in HL60 and HCT116 Cells

Log-phase cells were seeded in a 75-mL flask overnight to allow cell attachment, with the seeding density chosen so that the cell culture would be less than 80% confluent on the day of harvest. The test compounds were added (dissolved in DMSO) at about $IC_{80}$ to achieve a final DMSO concentration of 0.1%, and the cells then incubated further for one, two, or three days. Following incubation, the cells were harvested, washed with cold PBS, fixed in 75% aqueous ethanol, and stored at −20° C. until further analysis. To determine the cellular DNA content, which reflects the cell cycle status, the fixed cells were washed twice with phosphate-buffered saline and then treated with RNase for 30 minutes at 37° C. They were then stained with propidium iodide, followed by FACS analysis on a Becton Dickinson FACSCalibur system. All compounds tested induced polyploidy followed by apoptosis in HL60 cells, and polyploidy in HCT116 cells, indicative of Aurora kinase B inhibition.

IN VIVO EXAMPLES

In Vivo Example 1

HL60 Xenograft Assay, Oral Administration

Male athymic nu/nu mice, 6-8 weeks old (about 20 g), were implanted subcutaneously in the right fore flank with about $1 \times 10^7$ cells of the HL60 (human promyelocytic leukemia) line that had been grown in antibiotic-free medium for at least two passages. About 6 days after tumor implantation, when the tumor weight was about 50-250 mg, the mice were assigned to treatment groups. Test compounds were solubilized at 15 mg/mL in 25 wt. % aqueous hydroxypropyl 3-cyclodextrin. Groups of mice were treated with compounds 39A, 41A, 75A, 77A, 85A, 95A, and 101A at 150 mg/Kg by gavage once/day on days 1-5 and 8-10 from the start of treatment, with vehicle control. Tumor growth inhibition was measured 1-2 days after the last day of treatment. All compounds tested were active in this assay, with compound 39A causing 47% inhibition of tumor growth compared to vehicle, compound 41A causing 81% inhibition, compound 75A causing 72% inhibition, compound 77A causing 75% inhibition, compound 85A causing 45% inhibition, compound 95A causing 59% inhibition, and compound 101A causing 38% inhibition. Similar studies with compounds 139A, 141A, 142A, and 143A dissolved at 4, 10, 10 and 10 mg/mL in 0.1M sodium acetate at pH5, dosing at 40, 100, 100, and 100 mg/mL, showed tumor inhibition of 65%, 49%, 89% and 65% relative to vehicle.

In Vivo Example 2

HCT116 Xenograft Assay, Oral Administration

Male athymic nu/nu mice, 6-8 weeks old (about 20 g), were implanted subcutaneously in the right fore flank with about $1 \times 10^7$ cells of the HCT116 (human colon carcinoma) line that had been grown in antibiotic-free medium for at least two passages. About 14-21 days after tumor transplantation, when the tumor weight was about 50-250 mg, the mice were assigned to treatment groups. Test compounds were solubilized at 15 mg/mL in 25 wt. % aqueous hydroxypropyl 3-cyclodextrin. Groups of mice were treated with compounds 39A, 40A, 60A, 75A, 95A, and 117A at 150 mg/Kg by gavage once/day on days 1-5 and 8-12 from the start of treatment, with vehicle control. Tumor growth inhibition was measured 9 days after the last day of treatment. All compounds tested were active in this assay, with compound 39A causing 56% inhibition of tumor growth compared to vehicle, compound 40A causing 18% inhibition, compound 60A causing 37% inhibition, compound 75A causing 60% inhibition, compound 95A causing 61% inhibition, and compound 117A causing 42% inhibition. A similar study with compound 139A dissolved at 4 mg/mL in 0.1M sodium acetate at pH5, dosing at 40 mg/mL, showed tumor inhibition of 46% relative to vehicle.

FORMULATION EXAMPLES

Formulation Example 1

Formulation for Oral Administration

A solid formulation for oral administration is prepared by combining the following:

| | |
|---|---|
| Compound of this invention | 25.0% w/w |
| Magnesium stearate | 0.5% w/w |
| Starch | 2.0% w/w |
| Hydroxypropylmethylcellulose | 1.0% w/w |
| Microcrystalline cellulose | 71.5% w/w | and the mixture is compressed to form tablets or filled into hard gelatin capsules containing, for example, 100 mg of the compound of this invention. Tablets may be coated, if desired, by applying a suspension of a film-forming agent (for example, hydroxypropylmethylcellulose), pigment (for example, titanium dioxide), and plasticizer (for example, diethyl phthalate), and drying the film by evaporation of the solvent.

Formulation Example 2

Formulation for IV Administration

A formulation for IV administration is prepared by dissolving a compound of this invention, for example as a pharmaceutically acceptable salt, to a concentration of 1% w/v in phosphate-buffered saline; and the solution is sterilized, for example by sterile filtration, and sealed in sterile containers containing, for example, 100 mg of a compound of this invention.

Alternatively, a lyophilized formulation is prepared by dissolving a compound of this invention, again for example as a pharmaceutically acceptable salt, in a suitable buffer, for example the phosphate buffer of the phosphate-buffered saline mentioned above, sterilizing the solution and dispensing it into suitable sterile vials, lyophilizing the solution to remove the water, and sealing the vials. The lyophilized formulation is reconstituted by the addition of sterile water, and the reconstituted solution may be further diluted for administration with a solution such as 0.9% sodium chloride intravenous infusion or 5% dextrose intravenous infusion.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

We claim:
1. A compound of the formula,

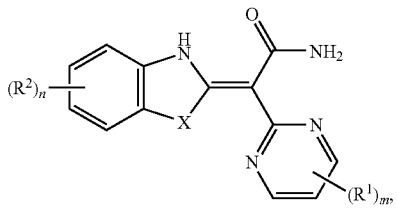

or a salt thereof,
where:
X is NH or S;
m is 0, 1, 2, or 3;
n is 0, 1, 2, 3, or 4;
$R^1$ is alkyl, substituted alkyl, heteroalkyl, substituted heteroalkyl, aryl, substituted aryl, heteroaryl, substituted heteroaryl, aralkyl, substituted aralkyl, heteroaralkyl, substituted heteroaralkyl, halo, nitro, or cyano, or is —OR, —SR, —C(O)R, —OC(O)R, —C(O)OR, —NR$_2$, —SO$_2$OR, —OSO$_2$R, —SO$_2$NR$_2$, —NR$^3$SO$_2$R, —CONR$_2$, —NR$^3$COR, or —NR$^3$C(O)OR, where each R independently is hydrogen, alkyl, substituted alkyl, heteroalkyl, substituted heteroalkyl, aryl, substituted aryl, heteroaryl, substituted heteroaryl, aralkyl, substituted aralkyl, heteroaralkyl, or substituted heteroaralkyl, and $R^3$ is hydrogen or $C_1$-$C_3$ alkyl; and
$R^2$ is alkyl, substituted alkyl, heteroalkyl, substituted heteroalkyl, aryl, substituted aryl, heteroaryl, substituted heteroaryl, aralkyl, substituted aralkyl, heteroaralkyl, substituted heteroaralkyl, halo, nitro, or cyano, or is —OR, —SR, —C(O)R, —OC(O)R, —C(O)OR, —NR$_2$, —SO$_2$OR, —OSO$_2$R, —SO$_2$NR$_2$, —NR$^3$SO$_2$R, —CONR$_2$, —NR$^3$COR, or —NR$^3$C(O)OR, where each R independently is hydrogen, alkyl, substituted alkyl, heteroalkyl, substituted heteroalkyl, aryl, substituted aryl, heteroaryl, substituted heteroaryl, aralkyl, substituted aralkyl, heteroaralkyl, or substituted heteroaralkyl, and $R^3$ is hydrogen or $C_1$-$C_3$ alkyl.

2. A compound of claim 1 where X is NH.
3. A compound of claim 1 where X is S.
4. A compound of claim 1 where m is at least 1.
5. A compound of claim 1 where m is 1.
6. A compound of claim 5 where $R^1$ is on the 4-position of the pyrimidine, and is methyl, methoxy, or trifluoromethyl.
7. A compound of claim 1 where m is 2.
8. A compound of claim 7 where one $R^1$ is on the 4-position of the pyrimidine, and is methyl, methoxy, or trifluoromethyl.
9. A compound of claim 8 where the other $R^1$ is a group selected from the —OR, —SR, —C(O)R, —OC(O)R, —C(O)OR, —OSO$_2$R, —SO$_2$NR$_2$, —NR$^3$SO$_2$R, —CONR$_2$, —NR$^3$COR, and —NR$^3$C(O)OR.
10. A compound of claim 1 where n is 0.
11. A compound of claim 1 where n is at least 1.
12. A compound of claim 1 where n is 1.
13. A compound of claim 12 where $R^2$ is a group selected from —OR, —SR, —C(O)R, —OC(O)R, —C(O)OR, —NR$_2$, —SO$_2$OR, —OSO$_2$R, —SO$_2$NR$_2$, —NR$^3$SO$_2$R, —CONR$_2$, —NR$^3$COR, and —NR$^3$C(O)OR.
14. A compound of claim 1 where n is 2.
15. A compound of claim 14 where one $R^2$ is a group selected from —OR, —SR, —C(O)R, —OC(O)R, —C(O)OR, —NR$_2$, —SO$_2$OR, —OSO$_2$R, —SO$_2$NR$_2$, —NR$^3$SO$_2$R, —CONR$_2$, —NR$^3$COR, and —NR$^3$C(O)OR.
16. A compound of claim 1 selected from:
2-(5-{[3-(4-morpholinyl)propyl]aminocarbonyl}-1H-benzimidazol-2(3H)-ylidene)-2-(4-trifluoromethylpyrimidin-2-yl)acetamide,
2-(6-{[3-(4-morpholinyl)propyl]aminocarbonyl}-benzothiazol-2(3H)-ylidene)-2-(4-trifluoromethylpyrimidin-2-yl)acetamide,
2-(5-{[3-(4-morpholinyl)propyl](ethyl)aminocarbonyl}-1H-benzimidazol-2(3H)-ylidene)-2-(4-trifluoromethylpyrimidin-2-yl)acetamide,
2-[5-(piperazine-1-carbonyl)-1H-benzimidazol-2(3H)-ylidene]-2-(4-trifluoromethylpyrimidin-2-yl)acetamide,
2-{5-[(diethylaminomethyl)carbonylamino]-1H-benzimidazol-2(3H)-ylidene}-2-(4-trifluoromethylpyrimidin-2-yl)acetamide,
2-{5-[(S)-(1-methylpyrrolidin-2-yl)carbonylamino]-1H-benzimidazol-2(3H)-ylidene}-2-(4-trifluoromethylpyrimidin-2-yl)acetamide,
2-{5-[(1-amino-1-methylethyl)carbonylamino]-1H-benzimidazol-2(3H)-ylidene}-2-(4-trifluoromethylpyrimidin-2-yl)acetamide,
2-{5-[(RS)-(1-methylpiperidin-2-yl)carbonylamino]-1H-benzimidazol-2(3H)-ylidene}-2-(4-trifluoromethylpyrimidin-2-yl)acetamide,
2-({5-[2-(4-methylpiperazin-1-yl)ethyl]carbonylamino}-1H-benzimidazol-2(3H)-ylidene)-2-(4-trifluoromethylpyrimidin-2-yl)acetamide,
2-(6-{[2-(imidazol-1-yl)ethyl]benzothiazol-2(3H)-ylidene})-2-(4-trifluoromethylpyrimidin-2-yl)acetamide,
2-(6-{[2-(1,1-dioxothiomorpholin-4-yl)ethyl]benzothiazol-2(3H)-ylidene})-2-(4-trifluoromethylpyrimidin-2-yl)acetamide,
2-(6-{[2-(morpholin-4-yl)ethyl]benzothiazol-2(3H)-ylidene})-2-(4-trifluoromethylpyrimidin-2-yl)acetamide,
2-(6-{[2-(imidazol-1-yl)ethyloxy]benzothiazol-2(3H)-ylidene})-2-(4-trifluoromethylpyrimidin-2-yl)acetamide,
2-(1H-benzimidazol-2(3H)-ylidene)-2-[4-methyl-6-(trifluoromethyl)pyrimidin-2-yl]acetamide,
2-(5-{[(diethylaminomethyl)carbonyl](ethyl)amino}-1H-benzimidazol-2(3H)-ylidene)-2-(4-trifluoromethylpyrimidin-2-yl)acetamide,
2-{5-[(S)-(1-methylpiperidin-2-yl)carbonylamino]-1H-benzimidazol-2(3H)-ylidene}-2-(4-trifluoromethylpyrimidin-2-yl)acetamide,
2-{5-[(R)-(1-methylpiperidin-2-yl)carbonylamino]-1H-benzimidazol-2(3H)-ylidene}-2-(4-trifluoromethylpyrimidin-2-yl)acetamide,
2-{5-[(S)-(1-methylpyrrolidin-2-yl)carbonylamino]-1H-benzimidazol-2(3H)-ylidene}-2-[4-methyl-6-(trifluoromethyl)pyrimidin-2-yl]acetamide,
2-(5-{[(S)-(1-methylpyrrolidin-2-yl)carbonyl](ethyl)amino}-1H-benzimidazol-2(3H)-ylidene)-2-(4-trifluoromethylpyrimidin-2-yl)acetamide, and
2-(5-{[(piperidin-1-ylmethyl)carbonyl](ethyl)amino}-1H-benzimidazol-2(3H)-ylidene)-2-(4-trifluoromethylpyrimidin-2-yl)acetamide,
or a salt thereof.
17. A compound of claim 16 selected from:
2-(5-{[3-(4-morpholinyl)propyl](ethyl)aminocarbonyl}-1H-benzimidazol-2(3H)-ylidene)-2-(4-trifluoromethylpyrimidin-2-yl)acetamide, 2-{5-[(diethyl aminomethyl)carbonyl amino]-1H-benzimidazol-2(3H)-ylidene}-2-(4-trifluoromethylpyrimidin-2-yl)acetamide, 2-({5-[2-(4-methylpiperazin-1-yl)ethyl]carbonylamino}-1H-benzimidazol-2(3H)-ylidene)-2-(4-trifluoromethylpyrimidin-2-yl)acetamide, 2-(5-{[(diethylaminomethyl)carbonyl](ethyl)amino}-1H-benzimidazol-2(3H)-ylidene)-2-(4-trifluoromethylpyrimidin-2-yl)acetamide, 2-{5-[(S)-(1-methylpiperidin-2-yl)carbonylamino]-1H-benzimidazol-2(3H)-ylidene}-2-(4-trifluoromethylpyrimidin-2-yl)acetamide, 2-{5-[(R)-(1-methylpiperidin-2-yl)carbonylamino]-1H-benzimidazol-2(3H)-ylidene}-2-(4-trifluoromethylpyrimidin-2-yl)acetamide, and 2-(5-{[(S)-(1-methylpyrrolidin-2-yl)carbonyl](ethyl)amino}-1H-benzimidazol-2(3H)-ylidene)-2-(4-trifluoromethylpyrimidin-2-yl)acetamide, or a salt thereof.

18. A pharmaceutical composition comprising a therapeutically effective amount of a compound of claim 1, in combination with an excipient.

19. A method of treatment of colon cancer comprising administration of a compound of claim 1 to a subject in need thereof.

20. A method of treatment of promyelocytic leukemia comprising administration of a compound of claim 1 to a subject in need thereof.

21. A method for inhibiting an aurora kinase or a VEGFR2 kinase which method comprises contacting the kinase with an inhibitory amount of a compound of claim 1.

* * * * *